United States Patent
Terstiege et al.

(10) Patent No.: US 12,240,832 B2
(45) Date of Patent: Mar. 4, 2025

(54) IRAK4 INHIBITORS

(71) Applicant: ASTRAZENECA AB, Sodertalje (SE)

(72) Inventors: Ina Terstiege, Sodertalje (SE); Stefan Schiesser, Sodertalje (SE)

(73) Assignee: ASTRAZENECA AB, Sodertalje (SE)

( * ) Notice: Subject to any disclaimer, the term of this patent is extended or adjusted under 35 U.S.C. 154(b) by 0 days.

(21) Appl. No.: 18/612,156

(22) Filed: Mar. 21, 2024

(65) Prior Publication Data
US 2024/0300923 A1    Sep. 12, 2024

Related U.S. Application Data

(63) Continuation of application No. PCT/EP2023/053416, filed on Feb. 13, 2023.

(60) Provisional application No. 63/267,956, filed on Feb. 14, 2022.

(51) Int. Cl.
| | | |
|---|---|---|
| *C07D 401/14* | (2006.01) | |
| *A61K 31/4439* | (2006.01) | |
| *A61K 31/444* | (2006.01) | |
| *A61K 31/501* | (2006.01) | |
| *C07D 401/12* | (2006.01) | |
| *C07D 405/14* | (2006.01) | |
| *C07D 413/14* | (2006.01) | |

(52) U.S. Cl.
CPC ........ *C07D 401/14* (2013.01); *A61K 31/4439* (2013.01); *A61K 31/444* (2013.01); *A61K 31/501* (2013.01); *C07D 401/12* (2013.01); *C07D 405/14* (2013.01); *C07D 413/14* (2013.01)

(58) Field of Classification Search
None
See application file for complete search history.

(56) References Cited

U.S. PATENT DOCUMENTS

2022/0298139 A1    9/2022    Ye et al.

FOREIGN PATENT DOCUMENTS

| WO | 2016174183 A1 | 11/2016 | |
|---|---|---|---|
| WO | 2020263967 A1 | 12/2020 | |
| WO | 2022122876 A1 | 6/2022 | |
| WO | 2022140425 A1 | 6/2022 | |
| WO | WO-2022140415 A1 * | 6/2022 | ......... A61K 31/4439 |
| WO | WO-2023283610 A1 * | 1/2023 | ......... A61K 31/4545 |

OTHER PUBLICATIONS

International Search Report and Written Opinion for International Application No. PCT/EP2023/053416, mailed Apr. 18, 2023, 14 Pages.

* cited by examiner

*Primary Examiner* — Jeffrey S Lundgren
*Assistant Examiner* — Eric Tran

(57) ABSTRACT

The present application relates to chemical compounds of Formula (I), and pharmaceutically acceptable salts thereof, that inhibit IRAK4 and consequently have potential utility in medicine.

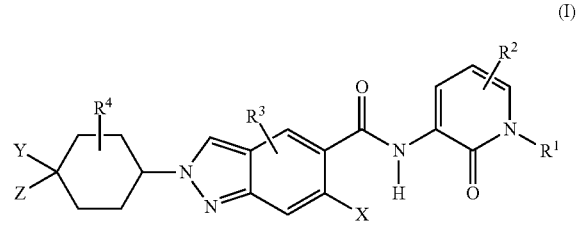

4 Claims, No Drawings

IRAK4 INHIBITORS

CROSS-REFERENCE TO RELATED APPLICATIONS

This application is a continuation of International Application No. PCT/EP2023/053416, filed on Feb. 13, 2023, which claims benefit under 35 U.S.C. § 119(e) of the U.S. Provisional Application No. 63/267,956, filed Feb. 14, 2022. Each of the above listed applications is incorporated by reference herein in its entirety for all purposes.

The specification relates to chemical compounds, and pharmaceutically acceptable salts thereof, that inhibit IRAK4 and consequently have potential utility in medicine. The specification also relates to the use of these IRAK4 inhibitors in the treatment of respiratory diseases such as asthma and chronic obstructive pulmonary disease (COPD), of cancer, of inflammatory diseases and of autoinflammatory/autoimmune diseases such as systemic lupus erythematosus, rheumatoid arthritis, myositis, Sjögren's syndrome, systemic sclerosis, gout, endometriosis, atopic dermatitis and psoriasis. The specification also relates to processes and intermediate compounds involved in the preparation of said IRAK4 inhibitors and to pharmaceutical compositions containing them.

Interleukin-1 receptor (IL-1R)-associated kinase 4 (IRAK4) is a key regulator of immune signaling. IRAK4 is expressed by multiple cell types and mediates signal transduction from Toll-like receptors (TLRs) and receptors of the interleukin-1 (IL-1) family, including IL-1R, IL-18R and the IL-33 receptor ST2. TLRs recognize and respond to ligands derived from microbes, such as lipopolysaccharide (LPS) or microbial RNA or DNA, while receptors of the IL-1 family can be activated by endogenous ligands produced by TLR-activated cells (IL-1β and IL-18) or by tissue damage (IL-1α and IL-33). Upon activation of TLRs or IL-1 receptors by their ligands, the adaptor protein myeloid differentiation primary response 88 (MyD88) is recruited to the receptor and forms a multimeric protein complex, called the "Myddosome", together with proteins of the IRAK family (IRAK1, IRAK2 and IRAK4). The Myddosome serves as a signaling platform to induce nuclear factor κB (NF-κB) and mitogen-activated protein kinase (MAPK) signal transduction pathways, culminating in the activation of transcription factors NF-κB, activator protein 1 (AP1), c-AMP response element-binding protein (CREB) and interferon regulatory factor 5 (IRF5), driving transcription of inflammatory cytokines and chemokines. Mice lacking IRAK4 are viable but lack inflammatory cytokine response to IL-1β, IL-18 and LPS. Humans presenting loss-of-function mutations in IRAK4 display an immunocompromised phenotype and their immune cells show an abrogated cytokine response to TLR agonists and IL-1 receptor ligands.

IRAK4 is characterized by an N-terminal death domain that mediates the interaction with MyD88 and a centrally located kinase domain. Myddosome formation promotes IRAK4 auto-phosphorylation which modulates the stability and downstream signaling of the Myddosome. The kinase activity of IRAK4 is required for cytokine induction by TLRs and IL-1R, as shown by studies in knock-in mice expressing a kinase-dead IRAK4, as well as in studies using small molecule IRAK4 kinase inhibitors.

Given its critical role in eliciting an inflammatory response, IRAK4 constitutes a target for drugs that exert an anti-inflammatory effect. Asthma and COPD (chronic obstructive pulmonary disease) are chronic lung diseases constituting a major unmet medical need around the world. Asthma and COPD are characterized by chronic airway inflammation, involving abnormal cytokine release, dysregulated immune cell activation and airway remodeling. In asthma, insults to the airways such as allergenic, viral and bacterial insults activate the TLR receptors via pathogen associated molecular patterns (PAMPs), and the IL-1R and ST2 receptors via the release of alarmins, including IL-33 and IL-1α, as well as by IL-1β released upon inflammasome activation. TLRs and receptors of the IL-1 family are present in multiple cell types in the airways, including macrophages, dendritic cells, mast cells, monocytes and epithelial cells, and respond to their ligands by releasing inflammatory cytokines (TNF-α, IL-6, IL-8, GM-CSF, IL-5) leading to airway inflammation, recruitment of inflammatory cells such as neutrophils and eosinophils, airway hyperresponsiveness and mucus production. IRAK4 inhibition has the potential to suppress these inflammatory pathways in the airways. Gene expression analysis of lung samples from asthma and COPD patients, have revealed an upregulated expression of genes associated with the IL-1R and TLR2/4 inflammatory pathways in subsets of severe patients. Although IRAK4 inhibitors have not, to the best of our knowledge, been explored in the clinic for the treatment of respiratory diseases, preclinical data from several research groups indicates that interfering with IRAK4-regulated pathways attenuates airway inflammation in animal models of both asthma and COPD. For instance, mice lacking MyD88, the central component of the Myddosome, are protected against airway inflammation induced by allergens or IL-33, as are mice treated with a small molecule mimetics blocking the interaction between IRAK2 and IRAK4. Blocking IL-1β with a monoclonal antibody has also been found to suppress airway inflammation induced by allergens and bacteria in a steroid-resistant mouse model of asthma. Moreover, the treatment of mice with the IL-1R antagonist anakinra at the time of allergen challenge ameliorates asthma-like symptoms in a mouse model of allergic asthma. Chronic exposure to cigarette smoke is a major contributing factor to the development of COPD. In mice exposed to cigarette smoke, IL-1 signaling is central in mediating neutrophilic airway inflammation, and blocking IL-1 signaling with antibodies against IL-1α, IL-1β or the IL-1R can ameliorate the neutrophilic inflammation in the lung and reduce bacteria- or virus-induced exacerbations in cigarette smoke-exposed mice. Taken together, IRAK4 inhibition has potential to provide a broad anti-inflammatory effect in inflammatory respiratory diseases by simultaneously blocking several disease-relevant signaling pathways.

As a central regulator of the Myddosome, IRAK4 is also a promising therapeutic target in other inflammatory diseases driven by IL-1R-, TLR- or ST2-mediated mechanisms. As previously disclosed, IRAK4 plays a role in autoimmune disorders such as rheumatoid arthritis and systemic lupus erythematosus (SLE) (see e.g. WO2017207386 & WO2015150995). In SLE, immunocomplexes composed by autoantibodies and self-antigens, can drive TLR-dependent pathological signaling. In SLE pathogenesis, IRAK4 inhibition reportedly blocks the release of type I interferons and pro-inflammatory cytokines mediated by TLR7 and TLR9 activation in plasmacytoid dendritic cells. Mice expressing a kinase-dead mutant of IRAK4 or treated with IRAK4 kinase inhibitor compounds, are resistant to experimentally induced arthritis and lupus (see e.g. WO2017207386). The approved use of anakinra (an IL-1 receptor antagonist) for the treatment of rheumatoid arthritis, also support the role of pathogenic IL-1R signaling in this disease. In Sjögren's syndrome, TLRs are upregulated in PBMCs (peripheral blood mononuclear cells) and salivary glands and TLR activation can stimulate release of interferon and other inflammatory cytokines, suggested to be implicated in Sjögren's pathogenesis. MyD88 knockout mice also display reduced disease manifestations in an experimental mouse model of Sjögren's syndrome. Systemic sclerosis is a severe autoimmune disorder where IL-1R, TLR4, TLR8 and ST2-signaling can drive pathogenic mechanisms, including microvascular damage and fibrosis. Inhibition of IRAK4 as a treatment in systemic sclerosis would thus block multiple disease-relevant pathways simultaneously. In myositis, elevated levels of IL-1α and IL-1β can contribute to muscle tissue inflammation. Myositis patients have also been characterized with high type I interferon gene signature, that may be partly driven by TLR7/9 activation, and the relevance of IL-1R signaling was supported by an improved clinical outcome in myositis patients treated with anakinra in a smaller mechanistic clinical trial. As a central regulator of the IL-1R pathway, IRAK4 is also a promising target in the treatment of gout. Monosodium urate crystals, characteristically formed in gout sufferers, can trigger the activation of the inflammasome and release of IL-1β. The use of both canakinumab, an anti IL-1β monoclonal antibody or anakinra has demonstrated clinical efficacy in the treatment of gout flares. Elevated levels of IL-1β and IL-33 have also been found in patients with endometriosis. The importance of IRAK4 in the disease process of endometriosis was shown in a mouse model where oral administration of an IRAK4 inhibitor suppressed lesion formation. MyD88 knockout mice were also protected against the development of endometriosis in the same mouse model. IL-33/ST2 signaling is a key mechanism in atopic dermatitis, involved in the regulation of skin inflammation, epithelial barrier integrity and eosinophil recruitment. IL-33 can trigger eczema and dermatitis in mice in a MyD88-dependent manner. As a regulator of ST2 signaling and a central component of the Myddosome, IRAK4 inhibition has the potential to inhibit pathogenic IL-33/ST2 signaling in atopic dermatitis. Both TLR7 and IL-1R mediated mechanisms have been suggested to be involved in psoriasis. Imiquimod (TLR/8 agonist) can induce psoriasis-like disease in mice in a MyD88-dependent manner. IL-1β is upregulated in psoriatic skin lesions and the IL-1β/IL-1R axis has been suggested to contribute to skin inflammation and regulate the production of IL-17, a critical cytokine released from TH17 cells in psoriasis pathogenesis. IRAK4 kinase activity has further been shown to be required for the regulation of TH17 differentiation and TH17-mediated diseases in vivo.

A number of IRAK4 kinase inhibitors are known and have been developed principally for use in oncology or inflammatory disease (see e.g. WO2015150995, WO2017207386, WO2017009806, WO2016174183, WO2018234342, WO2020263967, WO2020263980). Of the known IRAK4 kinase inhibitors PF-06650833 has recently completed a phase II clinical trial for the treatment of rheumatoid arthritis (see clinicaltrials.gov entry for NCT02996500).

Taken together, IRAK4 inhibitors have potential for the treatment of a number of diseases and conditions albeit to date no such inhibitor has been approved for clinical use. It is an object of the present specification to provide new IRAK4 inhibitors with physicochemical and selectivity profiles that render them suitable for clinical use, for example in the treatment of inflammatory diseases associated with activation of IRAK4-mediated pathways, such as cancer, asthma, COPD and chronic autoimmune/autoinflammatory diseases.

In a first aspect, the present specification provides a compound of Formula (I), or a pharmaceutically acceptable salt thereof,

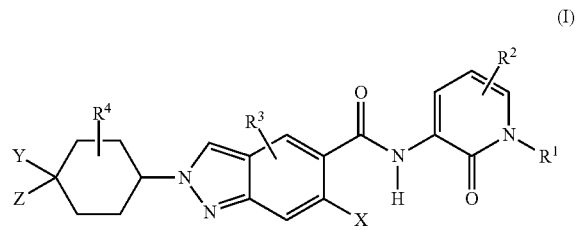

wherein:
  $R^1$ is selected from i) H, Me, Et, Pr, i-Pr, cyclopropyl, $CH_2CN$, $CH_2F$ and oxetane, or ii) a $C_1$-$C_6$ alkyl group, a $C_3$-$C_6$ cycloalkyl group or a 5-membered N-heterocycle in each case optionally substituted with one or more substituents selected from Me, F, Cl, CN, OMe and $C_1$-$C_3$ alkyl;
  $R^2$ is selected from H, F, Cl, D and Me;
  $R^3$ and $R^4$ are each independently selected from H, Me, Et, F, Cl, optionally substituted $C_1$-$C_3$ alkyl and $C_1$-$C_3$ haloalkyl;
  Y is $N(Me)COMe$, $N(R^5)COMe$, $N(Me)COR^6$, $N(Me)COCH(OH)Me$, $N(Me)COCH(OR^5)R^6$, $N(R^5)COR^6$, $CONMe_2$, $CONR^5R^6$, a 5-membered N-heterocycle such as 1,2,3-triazole, 1,2,4-triazole, 1,3,4-oxadiazole, 2-pyrrolidinone, 2-imidazolidinone, imidazole or pyrazole, or a 6-membered N-heterocycle such as 1-pyridone or pyridazine, wherein the 5- or 6-membered N-heterocycle is optionally substituted with a group $R^5$ at N or with a group $R^6$ at C, and Z is H, Me, Et or optionally substituted $C_1$-$C_6$ alkyl; or
  Y and Z combine to form an optionally substituted 4-, 5- or 6-membered ring;
  X is selected from $OR^7$ and $NR^8R^9$;
  $R^5$ is selected from H, Me, optionally substituted $C_1$-$C_6$ alkyl and optionally substituted $C_3$-$C_6$ cycloalkyl;
  $R^6$ is selected from Me, optionally substituted $C_1$-$C_6$ alkyl and optionally substituted $C_3$-$C_6$ cycloalkyl;
  $R^7$ is Me, Et, i-propyl, n-propyl, cyclopropyl, cyclobutyl, an optionally substituted $C_1$-$C_6$ alkyl, $C_3$-$C_6$ cycloalkyl, —$CH_2$($C_3$-$C_6$ cycloalkyl) or a 4-, 5- or 6-membered ring containing an heteroatom selected from O and N;
  $R^8$ and $R^9$ are independently selected from H, Me and optionally substituted $C_1$-$C_6$ alkyl or together form an optionally substituted $C_3$-$C_6$ cycloalkyl or an optionally substituted 4-, 5- or 6-membered ring containing a further heteroatom selected from O and N;
  wherein the optional substituents of Z, $R^3$, $R^4$, $R^5$, $R^6$, $R^7$, $R^8$ and $R^9$, when present, are independently selected from OH, $C_1$-$C_3$ alkyl, $C_1$-$C_3$ alkoxy, C(O)Me, amino, NHMe, $NMe_2$, F or Cl.

The specification also describes a pharmaceutical composition that comprises a compound of Formula (I), or a pharmaceutically acceptable salt thereof, and at least one pharmaceutically acceptable excipient.

The specification also describes a compound of Formula (I), or a pharmaceutically acceptable salt thereof, for use as a medicament.

The specification also describes a compound of Formula (I), or a pharmaceutically acceptable salt thereof, for use in the treatment of respiratory diseases such as asthma and chronic obstructive pulmonary disease (COPD).

The specification also describes a compound of Formula (I), or a pharmaceutically acceptable salt thereof, for use in the treatment of inflammatory diseases.

The specification also describes a compound of Formula (I), or a pharmaceutically acceptable salt thereof, for use in the treatment of autoinflammatory/autoimmune diseases such as systemic lupus erythematosus, rheumatoid arthritis, myositis, Sjögren's syndrome, systemic sclerosis, gout, endometriosis, atopic dermatitis and psoriasis.

The specification also describes a compound of Formula (I), or a pharmaceutically acceptable salt thereof, for use in the treatment of cancer, for example for use in combination with a BTK inhibitor.

The specification also describes a compound of Formula (I), or a pharmaceutically acceptable salt thereof, for use in the treatment of cancer. In such uses the compound of Formula (I) may be used as a monotherapy, or in combination with a further therapeutic agent, for example for the treatment of a haematologic malignancy. The haematologic malignancy to be treated may be selected from Waldenstrom's macroglobulinemia (WM), non-Hodgkin lymphoma (NHL), diffuse large B-cell lymphoma (DLBCL), primary central nervous system lymphoma (PCNSL), Splenic Marginal Zone Lymphoma (SMZL), small lymphocytic lymphoma (SLL), leukaemias (chronic lymphocytic leukaemia (CLL)) and monoclonal gammopathy of undetermined significance (MGUS-IgM+). Furthermore, the use may be for the treatment of haematologic malignancies that has MYD88 mutation, B-cell receptor (BCR) mutation or both MYD88 and BCR mutations. When the compound is used in combination with a further therapeutic agent the second agent may be selected from group comprising BCR inhibitors such as BTK inhibitors (examples include ibrutinib, acalabrutinib, zanubrutinib or tirabrutinib), PI3Kδ inhibitors and SYK inhibitors or immunotherapies.

The specification also describes the use of a compound of Formula (I) for the manufacture of a medicament, for example wherein the medicament is for use in the treatment of respiratory diseases such as asthma and chronic obstructive pulmonary disease (COPD) or for use in the treatment of cancer or for use in the treatment of autoinflammatory/ autoimmune diseases such as systemic lupus erythematosus, rheumatoid arthritis, myositis, Sjögren's syndrome, systemic sclerosis, gout, endometriosis, atopic dermatitis and psoriasis or for use in the treatment of inflammatory disease.

The specification also describes methods of treatment comprising administration of an effective amount of a compound of Formula (I) to a patient in need thereof, wherein the patient in need has a respiratory diseases such as asthma and chronic obstructive pulmonary disease (COPD), cancer, an autoinflammatory/autoimmune disease such as systemic lupus erythematosus, rheumatoid arthritis, myositis, Sjögren's syndrome, systemic sclerosis, gout, endometriosis, atopic dermatitis and psoriasis or an inflammatory disease.

The present specification also relates to processes for the manufacture of a compound of Formula (I).

Further aspects of the specification will be apparent to one skilled in the art from reading this specification.

As noted above, it has been found that compounds of Formula (I), or pharmaceutically acceptable salts thereof, are potent inhibitors of IRAK4 kinase. In addition, preferred compounds of Formula (I) exhibit excellent selectivity over other kinases thus providing a profile that avoids off target effects and toxicities. This desirable combination of IRAK4 inhibitory activity and lack of detrimental off target effect indicates the suitability of compounds of the specification for use in medicine.

Unless defined otherwise, all technical and scientific terms used herein have the same meaning as that commonly understood by one of ordinary skill in the art to which this disclosure is related. For example, the *Concise Dictionary of Biomedicine and Molecular Biology*, Juo, Pei-Show, 2nd ed., 2002, CRC Press; *The Dictionary of Cell and Molecular Biology*, 3rd ed., 1999, Academic Press; and the *Oxford Dictionary of Biochemistry and Molecular Biology*, Revised, 2000, Oxford University Press, provide one of skill with a general dictionary of many of the terms used in this disclosure.

So that the present specification may be more readily understood, certain terms are explicitly defined below. In addition, definitions are set forth as appropriate throughout the detailed description.

Units, prefixes, and symbols are denoted in their Système International de Unites (SI) accepted form. Numeric ranges are inclusive of the numbers defining the range.

The term "pharmaceutical composition" refers to a preparation which is in such form as to permit the biological activity of the active ingredient, and which contains no additional components which are unacceptably toxic to a subject to which the composition would be administered. Such compositions can be sterile. A pharmaceutical composition according to the present specification will comprise a compound of Formula (I), or a pharmaceutical acceptable salt thereof, and at least one pharmaceutically acceptable excipient.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have or develop the disorder; and those in whom the disorder is to be prevented. In certain aspects, a subject is successfully "treated" for respiratory disease according to the methods of the present disclosure if the patient shows, e.g., total, partial, or transient relief from the symptoms of that respiratory disease.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein the symbol * is used to indicate the site of connection of a component of the compound of Formula (I) to other components of the compound.

As used herein the term "alkyl" refers to both straight and branched chain saturated hydrocarbon radicals having the specified number of carbon atoms. As used herein the term deuteroalkyl refers to alkyl groups in which one or more, optionally all, hydrogens are replaced with deuterium atoms. The term cycloalkyl refers to a saturated cyclic hydrocarbon. As used in the term haloalkyl refers to alkyl groups in which one or more, optionally all, hydrogens are replaced with a halogen atom, for example wherein the halogen atom is a fluorine atom or a chlorine atom. Embodiments of haloalkyl groups include those that are fully fluorinated such as $CF_3$, $CF_2CF_3$, or that have a fluorine or chlorine replacing one or more hydrogens connected to the same carbon atom of the alkyl group such as $CH_2F$, $CH_2Cl$, $CF_2CH_3$, $CH_2CF_3$, $CH_2CH_2F$, and $CH_2CH_2Cl$.

In this specification the prefix "$C_x$-$C_y$", as used in terms such as $C_x$-$C_y$ alkyl and the like where x and y are integers, indicates the numerical range of carbon atoms that are present in the group. For example, $C_1$-$C_4$ alkyl includes methyl, ethyl, n-propyl, i-propyl, n-butyl, s-butyl, i-butyl and t-butyl, while examples of $C_1$-$C_3$ alkyl groups include methyl, ethyl, n-propyl, and i-propyl. $C_1$-$C_4$ alkoxy groups include methoxy, ethoxy, n-propoxy, i-propoxy, n-butoxy, s-butoxy and t-butoxy. Examples of $C_1$-$C_3$ alkoxy groups include methoxy, ethoxy, n-propoxy and i-propoxy.

Unless specifically stated, the bonding of an atom or group may be any suitable atom of that group; for example, propyl includes prop-1-yl and prop-2-yl.

As used herein the term "cycloalkyl" refers to cyclic saturated hydrocarbon radicals having the specified number of carbon atoms. Thus $C_3$-$C_6$ cycloalkyl refers to cyclopropyl, cyclobutyl, cyclopentyl and cyclohexyl groups.

As used herein the term "alkoxy" refers to a group with an oxygen atom connected to an alkyl chain wherein, as defined above the alkyl chain is a straight and branched chain saturated hydrocarbon radicals having the specified number of carbon atoms. Thus $C_1$-$C_3$ alkoxy refers to methoxy, ethoxy, $O^nPr$ and $O^iPr$ groups.

As described herein the group $R^1$ may be a 5-membered N-heterocycle that is optional substituted with one or more substituents selected from Me, F, Cl, CN, OMe and $C_1$-$C_3$ alkyl. In embodiments, the 5-membered N-heterocycle can be an aromatic heterocycle containing 1, 2 or 3 ring nitrogens, for example a pyrrole, imidazole, pyrazole, 1,2,3-triazole or 1,2,4-triazole. In embodiments a ring nitrogen of the 5-membered N-heterocycle is substituted with a $C_1$-$C_3$ alkyl group, for example a methyl group.

As described herein and above the cyclohexyl group may be substituted with a group $R^4$. In such cases the group $R^4$ may be attached to any available ring carbon. In embodiments $R^4$ is attached to the carbon atom adjacent the carbon atom attached to the indazole ring as shown below.

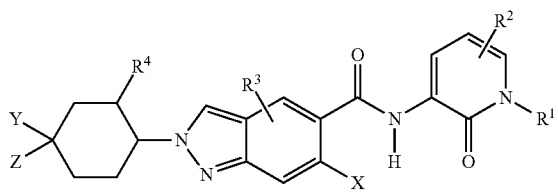

As used herein and above the term "acetyl" refers to a group of formula —C(O)Me. Reference to a N-acylated group herein is used to refer to amides with a small alkyl side chain i.e. an optionally substituted $C_1$-$C_6$ alkyl side chain or an optionally substituted $C_3$-$C_6$ cycloalkyl, in each instance the optional substituents are selected from OH, $C_1$-$C_3$ alkoxy, C(O)Me, amino, NHMe, $NMe_2$, F or Cl. In embodiments the N-acylated group is an N-acetyl group i.e. a group —NRC(O)Me.

As described herein and above the compounds of Formula (I) comprise a cyclohexyl ring substituted with two groups Y and Z that may combine to form a 4-, 5- or 6-membered ring. In such cases the 4-, 5- or 6-membered ring is a saturated hydrocarbon ring system optionally wherein one or two ring carbons are replaced with a heteroatom selected from O and N. In the case wherein two ring carbons are replaced with heteroatoms, the heteroatoms are not directly bound, i.e. the heteroatoms replace non-adjacent ring carbons, nor are they separated in the ring by a $CH_2$ group but may for example be joined by a carbonyl group to deliver e.g. a carbonate or carbamate motif. The hydrocarbon ring may incorporate a carbonyl group as is the case when Y and Z combine to form a cyclic amide. In embodiments, the 4-, 5- or 6-membered ring is a cyclic amide or carbamate such as a pyrrolidin-2-one, oxazolidin-2-one, piperidin-2-one and 1,3-oxazinan-2-one. Alternatively, the groups Y and Z may combine to form an azetidine substituted with an acyl group at nitrogen. In addition, the 4-, 5- or 6-membered ring may be substituted with a group selected from OH, $C_1$-$C_3$ alkyl, $C_1$-$C_3$ alkoxy, C(O)Me, amino, NHMe, $NMe_2$, F or Cl. These optional substituents may advantageously be used to modulate physicochemical properties of the molecule, such as solubility, or further optimize the interaction with IRAK4 kinase, for example relative to other kinases, thus delivering more potent and selective IRAK4 kinase inhibitors.

As described herein compounds of Formula (I) may comprise a group Y that is selected from N(Me)COMe, $N(R^5)COMe$, $N(Me)COR^6$, N(Me)COCH(OH)Me, N(Me)COCH($OR^5$)$R^6$, $N(R^5)COR^6$, $CONMe_2$, $CONR^5R^6$, a 5-membered N-heterocycle such as 1,2,3-triazole, 1,2,4-triazole, 1,3,4-oxadiazole, 2-pyrrolidinone, 2-imidazolidinone, imidazole or pyrazole, or a 6-membered N-heterocycle such as 1-pyridone or pyridazine, wherein the 5- or 6-membered N-heterocycle is optionally substituted with a group $R^5$ at N or with a group $R^6$ at C. In such cases the group Z is selected from H, Me, Et or optionally substituted $C_1$-$C_6$ alkyl. Other 5- and 6-membered N-heterocycles include pyrrole, pyridine, pyrimidine and pyrazine. In cases wherein the group Y is an optionally substituted 5- or 6-membered N-heterocycle embodiments include those in which a single $R^5$ group and/or a single $R^6$ group is present and the group $R^5$ or $R^6$ are selected from methyl, $C_1$-$C_3$ alkyl, $C_1$-$C_3$-hydroxyl alkyl, —CH(OH)$Me_2$, —C(OH)$Me_2$ or —$CH_2$CH(OH)Me. In embodiments, the $R^5$ and $R^6$ groups are selected from methyl, $C_1$-$C_3$ alkyl, $C_1$-$C_3$ hydroxyl alkyl, —CH(OH)$Me_2$, —C(OH)$Me_2$ and —$CH_2$CH(OH)Me. For example when Y is $N(Me)COR^6$, $R^6$ may be CH(OH)Me as shown below.

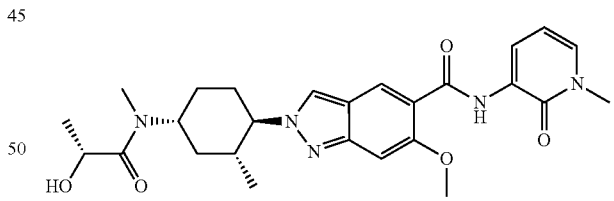

As described herein and above the group $R^7$ may be an optionally substituted 4-, 5- or 6-membered ring containing a heteroatom selected from O and N. For the avoidance of doubt "containing an heteroatom" means that one of the atoms of the ring will be a heteroatom selected from O or N. In embodiments the 4-, 5- or 6-membered ring containing a heteroatom selected from O and N is saturated. In embodiments the 4-, 5- or 6-membered rings containing a heteroatom selected from O and N is selected from azetidine, oxetane, tetrahydrofuran, pyrrolidine, tetrahydropyran and piperidine. As described herein and above the substituents $R^8$ and $R^9$ may combine to form an optionally substituted 4-, 5- or 6-membered ring containing a further heteroatom selected from O and N. In the case wherein a further heteroatom is present, the heteroatom is not directly bound to N, i.e. the heteroatoms in the ring are non-adjacent, nor are they separated by a $CH_2$ group. In embodiments the resultant ring is saturated, for example the resultant ring may be a morpholine or piperazine ring.

As will be apparent to the skilled reader, the compounds of Formula (I) and in particular the cyclohexyl group substituted with $R^4$, Y and Z etc can exist in various stereochemical forms. It will be understood that the claims encompass all stereochemical forms of the compounds of Formula (I), albeit the compounds with highest activity as inhibitors of IRAK4 are preferred. It will be recognised that the compounds of Formula (I), may be prepared, isolated and/or supplied with or without the presence, of one or more of the other possible stereoisomeric forms of the compound of Formula (I) in any relative proportions. The preparation of stereoenriched or stereopure compounds may be carried out by standard techniques of organic chemistry that are well known in the art, for example by synthesis from stereoenriched or stereopure starting materials, use of an appropriate stereoenriched or stereopure catalysts during synthesis, and/or by resolution of a racemic or partially enriched mixture of stereoisomers, for example via chiral chromatography. For example, the compounds according to the specification may be provided as mixtures in which >90%, >95% or >99% of the compound is present as a single enantiomer or diastereoisomer.

As described herein and above, certain components of the compounds of Formula (I) are optionally substituted. As used herein the term optionally substituted means that the structural element of the compound may or may not be substituted with one or more of the specified optional substituents. In instances wherein an optional substituent is present in one or more of the groups Z, $R^3$, $R^4$, $R^5$, $R^6$, $R^7$, $R^8$ and $R^9$, zero, one, two or three substituents are present per each substituted group, for example zero or one substituent is present. In the case wherein the two hydroxyl substituents are present, it will be understood that the two hydroxyl groups are not attached to the same carbon atom. In the case where the optional substituent is F, one, two or three F substituents may be present and, in addition, where two or three F substituents are present they are generally directly bound to the same carbon atom. In embodiments wherein the group $R^1$ is substituted with a $C_1$-$C_3$ alkyl group, one substituent, for example a methyl group, may be present. These optional substituents may be used to modulate physicochemical properties of the molecule, such as solubility, modulate metabolism, or further optimize the interaction with IRAK4 kinase, for example relative to other kinases, thus delivering more potent and selective IRAK4 kinase inhibitors. In embodiments wherein an optional substituent of Z, $R^3$, $R^4$, $R^5$, $R^6$, $R^7$, $R^8$ and $R^9$ is selected from OH, $C_1$-$C_3$ alkyl, $C_1$-$C_3$ alkoxy, C(O)Me, amino, NHMe and $NMe_2$, zero or one independently selected substituent per group is present (i.e. zero or one substituent independently selected from OH, $C_1$-$C_3$ alkyl, $C_1$-$C_3$ alkoxy, C(O)Me, amino, NHMe and $NMe_2$ may be present on each Z, $R^3$, $R^4$, $R^5$, $R^6$, $R^7$, $R^8$ or $R^9$ group). In embodiments wherein an optional substituent of Z, $R^3$, $R^4$, $R^5$, $R^6$, $R^7$, $R^8$ and $R^9$ is independently selected from F or Cl, zero, one, two or three independently selected substituent(s) per group can be present (i.e. zero, one, two or three independently selected substituents selected from F or Cl may be present on each Z, $R^3$, $R^4$, $R^5$, $R^6$, $R^7$, $R^8$ and $R^9$ group). In embodiments the groups Z, $R^3$, $R^4$, $R^5$, $R^6$, $R^7$, $R^8$ and $R^9$, in each case where present, are unsubstituted.

As noted above, in a first embodiment the specification provides a compound of Formula (I), or a pharmaceutically acceptable salt thereof,

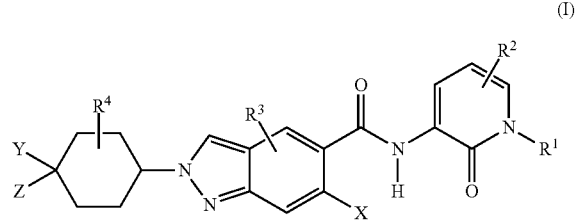

(I)

wherein:
$R^1$ is selected from i) H, Me, Et, Pr, i-Pr, cyclopropyl, $CH_2CN$, $CH_2F$ and oxetane, or ii) a $C_1$-$C_6$ alkyl group, a $C_3$-$C_6$ cycloalkyl group or a 5-membered N-heterocycle in each case optionally substituted with one or more substituents selected from Me, F, Cl, CN, OMe and $C_1$-$C_3$ alkyl;
$R^2$ is selected from H, F, Cl, D and Me;
$R^3$ and $R^4$ are each independently selected from H, Me, Et, F, Cl, optionally substituted $C_1$-$C_3$ alkyl and $C_1$-$C_3$ haloalkyl;
Y is $N(Me)COMe$, $N(R^5)COMe$, $N(Me)COR^6$, $N(Me)COCH(OH)Me$, $N(Me)COCH(OR^5)R^6$, $N(R^5)COR^6$, $CONMe_2$, $CONR^5R^6$, a 5-membered N-heterocycle such as 1,2,3-triazole, 1,2,4-triazole, 1,3,4-oxadiazole, 2-pyrrolidinone, 2-imidazolidinone, imidazole or pyrazole, or a 6-membered N-heterocycle such as 1-pyridone or pyridazine, wherein the 5- or 6-membered N-heterocycle is optionally substituted with a group $R^5$ at N or with a group $R^6$ at C, and Z is H, Me, Et or optionally substituted $C_1$-$C_6$ alkyl; or
Y and Z combine to form an optionally substituted 4-, 5- or 6-membered ring;
X is selected from $OR^7$ and $NR^8R^9$;
$R^6$ is selected from H, Me, optionally substituted $C_1$-$C_6$ alkyl and optionally substituted $C_3$-$C_6$ cycloalkyl;
$R^6$ is selected from Me, optionally substituted $C_1$-$C_6$ alkyl and optionally substituted $C_3$-$C_6$ cycloalkyl;
$R^7$ is Me, Et, i-propyl, n-propyl, cyclopropyl, cyclobutyl, an optionally substituted $C_1$-$C_6$ alkyl, $C_3$-$C_6$ cycloalkyl, —$CH_2(C_3$-$C_6$ cycloalkyl) or a 4-, 5- or 6-membered ring containing an heteroatom selected from O and N;
$R^8$ and $R^9$ are independently selected from H, Me and optionally substituted $C_1$-$C_6$ alkyl, or together form an optionally substituted $C_3$-$C_6$ cycloalkyl or an optionally substituted 4-, 5- or 6-membered ring containing a further heteroatom selected from O and N;
wherein the optional substituents of Z, $R^3$, $R^4$, $R^5$, $R^6$, $R^7$, $R^8$ and $R^9$, when present, are independently selected from OH, $C_1$-$C_3$ alkyl, $C_1$-$C_3$ alkoxy, C(O)Me, amino, NHMe, $NMe_2$, F or Cl.

In embodiments the compound of Formula (I) is a compound of Formula (Ia) in which the group $R^1$ is selected from

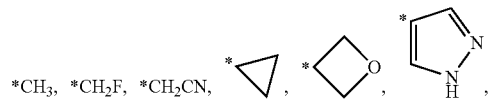

*$CH_3$, *$CH_2F$, *$CH_2CN$,

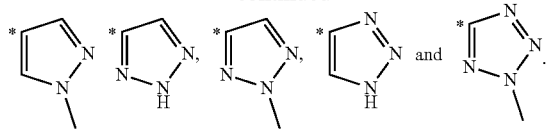

For clarity, as used herein the symbol "*" indicates the atom through which the group is connected to the rest of the molecule via a single bond, in this case the nitrogen atom of the pyridone.

In embodiments the compound of Formula (I) is a compound of Formula (Ib) in which the group $R^1$ is selected from methyl, fluoromethyl and cyanomethyl.

In embodiments the compound of Formula (I) is a compound of Formula (Ic) in which the group $R^1$ is cyclopropyl.

(Ic)
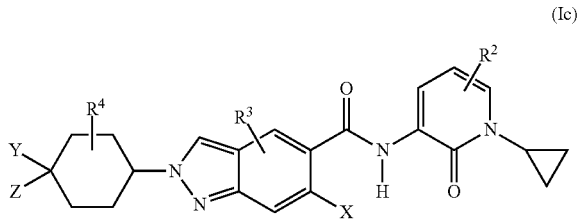

In embodiments the compound of Formula (I), (Ia), (Ib), (Ic) is a compound of Formula (Id) in which the group $R^2$ is H.

(Id)
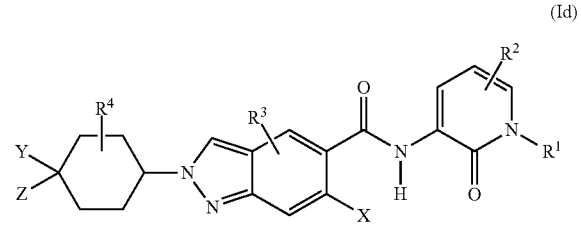

In embodiments the compound of Formula (I), (Ia), (Ib), (Ic) or (Id) is a compound of Formula (Ie) in which X is $OR^7$.

(Ie)
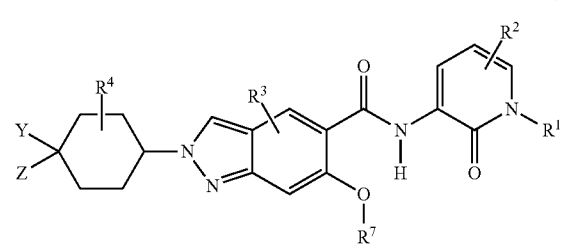

In embodiments the compound of Formula (Ie) is a compound of Formula (If) in which $R^7$ is Me.

(If)
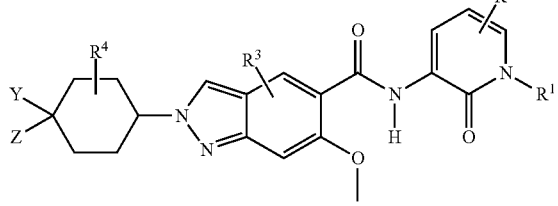

In embodiments the compound of Formula (I), (Ia), (Ib), (Ic), (Id), (Ie) or (If) is a compound of Formula (Ig) in which the group $R^3$ is H.

In embodiments the compound of Formula (I), (Ia), (Ib), (Ic), (Id), (Ie), (If) or (Ig) is a compound of Formula (Ih) in which $R^4$ is methyl.

In embodiments the compound of Formula (I), (Ia), (Ib), (Ic), (Id), (Ie), (If) or (Ig) is a compound of Formula (Ii) in which $R^4$ is H.

In embodiments the compound of Formula (I), (Ia), (Ib), (Ic), (Id), (Ie), (If), (Ig), (Ih) or (Ii) is a compound of Formula (Ij) in which Y is N(Me)COMe, N($R^5$)COMe, N(Me)$COR^6$, N(Me)COCH(OH)Me, N(Me)COCH($OR^5$)$R^6$, N($R^5$)$COR^6$, $CONMe_2$, $CONR^5R^6$, a 5-membered N-heterocycle such as 1,2,3-triazole, 1,2,4-triazole, 1,3,4-oxadiazole, 2-pyrrolidinone, 2-imidazolidinone, imidazole or pyrazole or a 6-membered N-heterocycle such as 1-pyridone or pyridazine and Z is H, Me, Et or optionally substituted $C_1$-$C_6$ alkyl.

In embodiments the compound of Formula (I), (Ia), (Ib), (Ic), (Id), (Ie), (If), (Ig), (Ih) or (Ii) is a compound of Formula (Ik) in which Y is selected from N(Me)COMe, N($R^5$)COMe, N(Me)$COR^6$, N(Me)COCH(OH)Me, N(Me)COCH($OR^5$)$R^6$, N($R^5$)$COR^6$, $CONMe_2$, $CONR^5R^6$, a 5-membered N-heterocycle such as 1,2,3-triazole, 1,2,4-triazole, 1,3,4-oxadiazole, 2-pyrrolidinone, 2-imidazolidinone, imidazole or pyrazole or a 6-membered N-heterocycle such as 1-pyridone or pyridazine and Z is H.

In embodiments the compound of Formula (I), (Ia), (Ib), (Ic), (Id), (Ie), (If), (Ig), (Ih) or (Ii) is a compound of Formula (II) in which Y is N(Me)COMe, N(Me)COCH(OH)Me, $CONMe_2$, or a 1,2,3-triazole, a 1,2,4-triazole, a 1,3,4-oxadiazole, a 2-pyrrolidinone, a 2-imidazolidinone, an imidazole, a pyrazole, a 1-pyridone or a pyridazine that is optionally substituted with a group $R^5$ at N or with a group $R^6$ at C and Z is H.

In embodiments the compound of Formula (I), (Ia), (Ib), (Ic), (Id), (Ie), (If), (Ig), (Ih) or (Ii) is a compound of Formula (Im) in which Y is a 5- or 6-membered N-heterocycle selected from

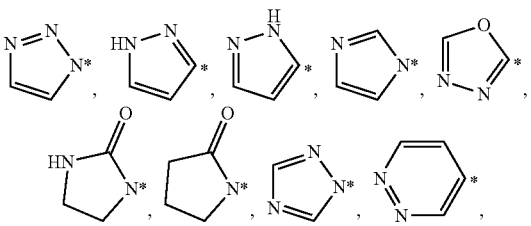

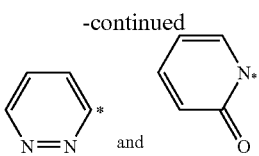

that is optionally substituted with a group R⁵ at N or with a group R⁶ at C, and Z is H.

In embodiments the compound of Formula (I), (Ia), (Ib), (Ic), (Id), (Ie), (If), (Ig), (Ih) or (Ii) is a compound of Formula (In) in which Y and Z combine to form an optionally substituted 4-, 5- or 6-membered ring.

In embodiments the compound of Formula (In) is a compound of Formula (Io) in which Y and Z combine with the carbon atom to which they are attached to form an oxazolidinone, for example N-methyl oxazolidinone,

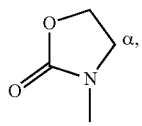

wherein the carbon atom to which Y and Z is bound is indicated by the symbol α.

In embodiments the compound of Formula (I), (Ia), (Ib), (Ic), (Id), (Ie), (If), (Ig), (Ih) or (Ii) is a compound of Formula (Io) in which Y is

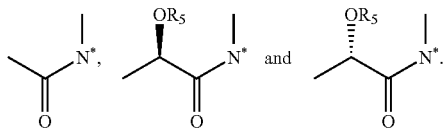

In embodiments the compound of Formula (I), (Ia), (Ib), (Ic), (Id), (Ie), (If), (Ig), (Ih) or (Ii) is a compound of Formula (Ip) in which Y is

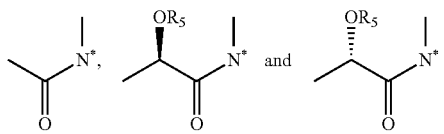

and Z is H.

In embodiments the compound of Formula (I), (Ia), (Ib), (Ic), (Id), (Ie), (If), (Ig), (Ih) or (Ii) is a compound of Formula (Iq) in which Y is

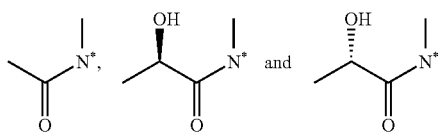

and Z is H.

In embodiments the compound of Formula (I) selected from:

6-Methoxy-N-(1-methyl-2-oxo-1,2-dihydropyridin-3-yl)-2-((1r,4r)-4-(N-methylacetamido)cyclohexyl)-2H-indazole-5-carboxamide;

6-Methoxy-N-(1-methyl-2-oxo-1,2-dihydropyridin-3-yl)-2-((1R,2R)-2-methyl-4-(N-methylacetamido)cyclohexyl)-2H-indazole-5-carboxamide;

6-Methoxy-N-(1-methyl-2-oxo-1,2-dihydropyridin-3-yl)-2-((1R,2S,4R)-2-methyl-4-(N-methylacetamido)cyclohexyl)-2H-indazole-5-carboxamide;

6-Methoxy-N-(1-methyl-2-oxo-1,2-dihydropyridin-3-yl)-2-((1S,2R,4S)-2-methyl-4-(N-methylacetamido)cyclohexyl)-2H-indazole-5-carboxamide;

rel-6-Methoxy-N-(1-methyl-2-oxo-1,2-dihydropyridin-3-yl)-2-((1R,2S,4S)-2-methyl-4-(N-methylacetamido)cyclohexyl)-2H-indazole-5-carboxamide;

2-((1R,4r)-4-((R)-2-Hydroxy-N-methylpropanamido)cyclohexyl)-6-methoxy-N-(1-methyl-2-oxo-1,2-dihydropyridin-3-yl)-2H-indazole-5-carboxamide;

N-(1-(fluoromethyl)-2-oxo-1,2-dihydropyridin-3-yl)-2-((1R,4r)-4-((R)-2-hydroxy-N-methylpropanamido)cyclohexyl)-6-methoxy-2H-indazole-5-carboxamide;

N-(1-(Cyanomethyl)-2-oxo-1,2-dihydropyridin-3-yl)-2-((1R,4r)-4-((R)-2-hydroxy-N-methylpropanamido)cyclohexyl)-6-methoxy-2H-indazole-5-carboxamide;

N-(1-Cyclopropyl-2-oxo-1,2-dihydropyridin-3-yl)-2-((1S,4r)-4-((S)-2-hydroxy-N-methylpropanamido)cyclohexyl)-6-methoxy-2H-indazole-5-carboxamide;

N-(1-Cyclopropyl-2-oxo-1,2-dihydropyridin-3-yl)-2-((1R,4r)-4-((R)-2-hydroxy-N-methylpropanamido)cyclohexyl)-6-methoxy-2H-indazole-5-carboxamide;

2-((1R,4r)-4-((R)-2-Hydroxy-N-methylpropanamido)cyclohexyl)-6-methoxy-N-(1-(oxetan-3-yl)-2-oxo-1,2-dihydropyridin-3-yl)-2H-indazole-5-carboxamide;

2-((1R,4r)-4-((R)-2-Hydroxy-N-methylpropanamido)cyclohexyl)-6-methoxy-N-(2-oxo-1-(1H-pyrazol-4-yl)-1,2-dihydropyridin-3-yl)-2H-indazole-5-carboxamide;

2-((1R,4r)-4-((R)-2-Hydroxy-N-methylpropanamido)cyclohexyl)-6-methoxy-N-(1-(1-methyl-1H-pyrazol-4-yl)-2-oxo-1,2-dihydropyridin-3-yl)-2H-indazole-5-carboxamide;

2-((1R,4r)-4-((R)-2-Hydroxy-N-methylpropanamido)cyclohexyl)-6-methoxy-N-(1-(1-methyl-1H-1,2,3-triazol-4-yl)-2-oxo-1,2-dihydropyridin-3-yl)-2H-indazole-5-carboxamide;

2-((1R,4r)-4-((R)-2-Hydroxy-N-methylpropanamido)cyclohexyl)-6-methoxy-N-(1-(2-methyl-2H-1,2,3-triazol-4-yl)-2-oxo-1,2-dihydropyridin-3-yl)-2H-indazole-5-carboxamide;

6-Methoxy-N-(1-methyl-2-oxo-1,2-dihydropyridin-3-yl)-2-((1r,4r)-4-(2-oxopyrrolidin-1-yl)cyclohexyl)-2H-indazole-5-carboxamide;

6-Methoxy-N-(1-methyl-2-oxo-1,2-dihydropyridin-3-yl)-2-((1r,4r)-4-(3-methyl-2-oxoimidazolidin-1-yl)cyclohexyl)-2H-indazole-5-carboxamide;

6-Methoxy-N-(1-methyl-2-oxo-1,2-dihydropyridin-3-yl)-2-((5s,8s)-1-methyl-2-oxo-3-oxa-1-azaspiro[4.5]decan-8-yl)-2H-indazole-5-carboxamide;

6-Methoxy-N-(1-methyl-2-oxo-1,2-dihydropyridin-3-yl)-2-((5r,8r)-1-methyl-2-oxo-3-oxa-1-azaspiro[4.5]decan-8-yl)-2H-indazole-5-carboxamide;

6-Methoxy-N-(1-methyl-2-oxo-1,2-dihydropyridin-3-yl)-2-((1r,4r)-4-(2-oxopyridin-1(2H)-yl)cyclohexyl)-2H-indazole-5-carboxamide;

6-Methoxy-N-(1-methyl-2-oxo-1,2-dihydropyridin-3-yl)-2-(4-(pyridazin-3-yl)cyclohexyl)-2H-indazole-5-carboxamide;

2-((1r,4r)-4-(1,3,4-Oxadiazol-2-yl)cyclohexyl)-6-methoxy-N-(1-methyl-2-oxo-1,2-dihydropyridin-3-yl)-2H-indazole-5-carboxamide;

2-((1r,4r)-4-(1H-1,2,4-Triazol-1-yl)cyclohexyl)-6-methoxy-N-(1-methyl-2-oxo-1,2-dihydropyridin-3-yl)-2H-indazole-5-carboxamide;

2-((1r,4r)-4-(1H-1,2,3-Triazol-1-yl)cyclohexyl)-6-methoxy-N-(1-methyl-2-oxo-1,2-dihydropyridin-3-yl)-2H-indazole-5-carboxamide;

2-((1r,4r)-4-(2-(1-hydroxyethyl)-1H-imidazol-1-yl)cyclohexyl)-6-methoxy-N-(1-methyl-2-oxo-1,2-dihydropyridin-3-yl)-2H-indazole-5-carboxamide and 2-((1r,4r)-4-(4-(2-Hydroxypropan-2-yl)-1H-1,2,3-triazol-1-yl)cyclohexyl)-6-methoxy-N-(1-methyl-2-oxo-1,2-dihydropyridin-3-yl)-2H-indazole-5-carboxamide;

or a pharmaceutically acceptable salt thereof.

The IRAK4 inhibitors of the present specification can be prepared from readily available starting materials, either available from commercial suppliers, such as Merck KGaA or by methods comprised in the common general knowledge of those skilled in the art. The reaction schemes below describe a variety of methods for the synthesis of the IRAK4 inhibitors. Typical or preferred reaction conditions might be given for the synthesis but those skilled in the art will be able to suggest modifications of these conditions to obtain analogues not described herein. Schemes presented below are therefore representative methods for the synthesis of the compounds of this specification and they should not be construed as constraining the scope of the specification in any way. In addition, the order of reactions can be modified to change the overall synthesis to allow for variations at different positions of the molecule at different stages of the synthesis.

The informed reader will recognize that the compounds described in the schemes below might in some cases be obtained as mixtures of regioisomers and stereoisomers, which can be separated at different stages of the synthesis using techniques such as silica/C18 chromatography, HPLC, SFC, crystallization etc. that are well known to those skilled in the art.

General Synthetic Approach to Compounds of Formula (I):

Scheme 1: General synthesis of building block I-2 alongside structure of group $R^a$ (in which $R^4$, Y and Z as defined above for a compound of Formula (I), or a suitably protected precursor thereof) as described below.

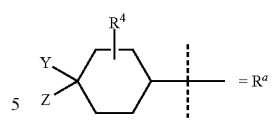

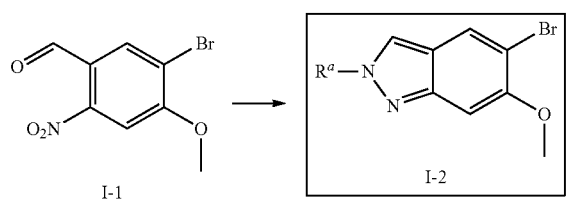

Scheme 1 describes the regioselective synthesis of the N-2 indazole building block I-2. Treatment of the commercially available starting material 1-1 with an amine $R^a$—$NH_2$ in a suitable solvent (e.g. i-PrOH) at elevated temperature, followed by addition of tri-n-butylphosphine results in the formation of I-2.

In instances in which the target molecule contains a functional group that is sensitive to, or incompatible with, the condensation reaction conditions, the reagent $R^a$—$NH_2$ may contain a suitably protected precursor of e.g. a component of the group Y of the final target compound that can be unmasked later in the synthesis. For example if the group Y of the final product contains an amine or amide, the reaction shown in Scheme 1 can be performed with a reagent $R^a$—$NH_2$ comprising a protected amine (e.g. a Boc protected amine), and the protecting group can be cleaved after the indazole core of I-2 is elaborated. Subsequently, the amine can be alkylated or converted into an amide as applicable. Likewise, if the group Y of the target molecule contains an alcohol functionality, the corresponding functionality of the precursor $R^a$—$NH_2$ can be protected with a suitable alcohol protection group, which withstands the reaction conditions of the reaction shown in Scheme 1 and that can be cleaved at a later stage in the synthesis of the target compound. Protecting groups are well known in the art (see e.g. Greene's Protective Groups in Organic Synthesis, Ed P. G. M. Wuts, Wiley, NY 2014, $5^{th}$ Edition). Alternatively, the agent $R^a$—$NH_2$ can contain a precursor of the amine/amide/alcohol functionality in form of a suitable protected carbonyl functionality which can be deprotected and converted to the desired amine/amide/alcohol functionality of the target compound in a later stage in the synthesis by synthetic methods known to those skilled in the art.

General Synthesis of Compounds of Formula (I):

Scheme 2: General synthesis of compounds of Formula (I), Method 1:

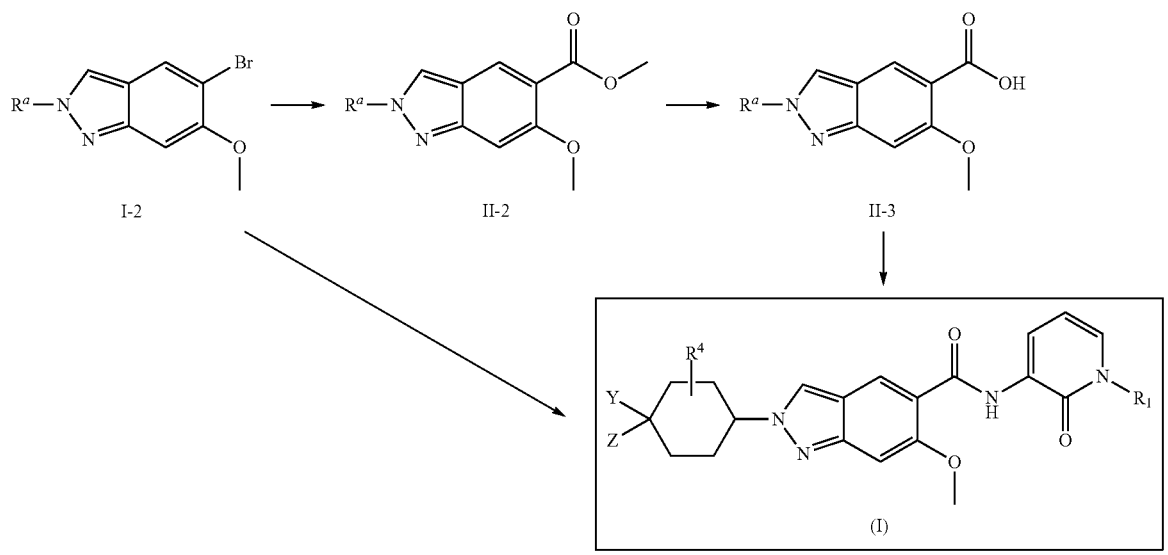

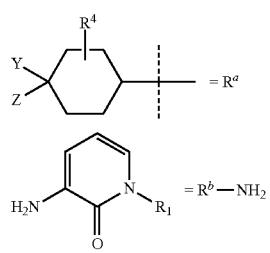

A method to prepare compounds of Formula (I) is shown in Scheme 2. A suitable starting material for this route is indazole I-2 (in which $R^4$, Y and Z are as defined in the claims for a compound of Formula (I), or a suitably protected precursor thereof) as described under Scheme 1. Bromide I-2 can be obtained as described in Scheme 1 and can be first treated with a Pd-catalyst (e.g. Pd(dppf)Cl$_2$) under an atmosphere of CO (at elevated pressure) in the presence of an alcohol as the solvent to yield ester II-2 (if MeOH is used as the solvent the Me-ester II-2 is formed). Subsequent cleavage of the ester by e.g. lithium hydroxide or potassium hydroxide in a suitable solvent (e.g. water) yields the carboxylic acid II-3. Amide formation from reaction of this acid II-3 with an amine $R^b$—NH$_2$ ($R^1$ as defined in the claims) can be performed with a variety of amide coupling reagents (e.g. HATU, T3P) to yield the desired compound of Formula (I).

The conversion of bromide I-2 into the compound of Formula (I) can also be performed in a one pot aminocarbonylation protocol. Stirring I-2 with a Pd-source (e.g. Pd(OAc)$_2$) and a suitable ligand (e.g. 1,3-bis(diphenylphosphino)propane or di(adamantan-1-yl)butylphosphane) in a solvent (e.g. MeCN) in the presence of a base (e.g. TEA) and the coupling amine $R^b$—NH$_2$ under an atmosphere of CO (at elevated pressure) yields the compound of Formula (I) in one step.

In instances where the reaction sequence shown in Scheme 2 starts with compound I-2 in which $R^a$ contains a protecting group, the transformation(s) to convert a suitably protected precursor of $R^4$, Y and/or Z in $R^a$ into $R^4$, Y and Z as defined for a compound of Formula (I) functionality (as examples described under Scheme 1) can be performed at different stages of the synthesis sequence shown in Scheme 2, depending on the nature of the transformation and the compatibility of the functional groups present in the sequence intermediates with the reaction conditions (a person skilled in the art will be able to decide the order of steps).

Scheme 3: General synthesis of compounds of Formula (I) with $R^c$=Y and Y and R$_1$ as defined above for a compound of Formula (I), Method 2:

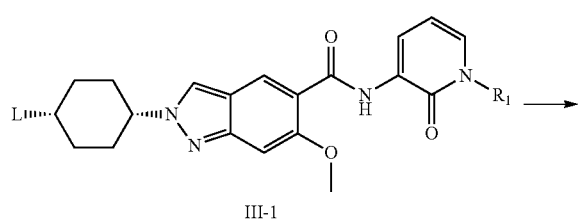

-continued

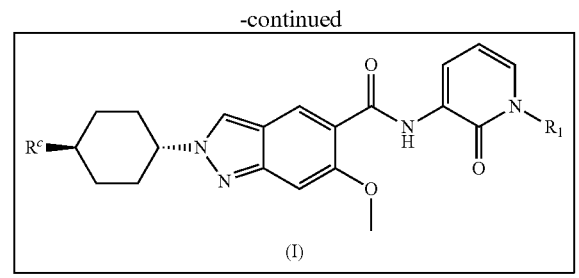

Scheme 3 shows an example how a compound III-1 (R$_1$ as defined in the claims for a compound of Formula (I) and L is a suitable leaving group for a nucleophilic substitution reaction, such as mesylate/tosylate) can be converted into a compound of Formula (I) by a nucleophilic substitution reaction with $R^c$. $R^c$ could, for example, be an azide or a triazole. The starting material III-1 can be obtained via the method shown in Scheme 2. The reaction shown in Scheme 3 could result directly in a compound of Formula (I) or a precursor which could be converted into a compound of Formula (I) by functional group interconversion (a person skilled in the art will be able to determine the necessary steps).

In embodiments of the specification there are provided methods of synthesizing compounds of Formula (I) or pharmaceutically acceptable salts thereof, intermediates in the synthesis of the compounds of Formula (I), for example methods and intermediates described herein and above.

In embodiments there are provided pharmaceutical compositions that comprise a compound of Formula (I) or a pharmaceutically acceptable salt thereof, in association with a pharmaceutically acceptable excipient. In such embodiments the compound of Formula (I) is preferably used as a single enantiomeric form. Minor impurities, for example up to 1% by mass of other stereoisomeric forms may be optionally be present. The pharmaceutical compositions can be used for the treatment of conditions in which IRAK4 kinase inhibition can be beneficial as described in more detail herein and above.

In embodiments there is provided a compound of Formula (I) for use in the production of a medicine, optionally wherein the medicines is for use in the treatment or prevention of a condition in which IRAK4 kinase inhibition can be beneficial as described in more detail herein and above.

The compounds of Formula (I) and pharmaceutically acceptable salts thereof may be prepared, used or supplied in amorphous form, crystalline form, or semi-crystalline form and any given compound of Formula (I) or pharmaceutically acceptable salt thereof may be capable of being formed into more than one crystalline and/or polymorphic form, including hydrated (e.g. hemi-hydrate, a mono-hydrate, a di-hydrate, a tri-hydrate or other stoichiometry of hydrate)

and/or solvated forms. It is to be understood that the present specification encompasses any and all such solid forms of the compound of Formula (I) and pharmaceutically acceptable salts thereof.

In further embodiments of the present specification there is provided a compound of Formula (I), which is obtainable by the methods described in the 'Examples' section hereinafter.

The present specification is intended to include all isotopes of atoms occurring in the present compounds. Isotopes will be understood to include those atoms having the same atomic number but different mass numbers. For example, isotopes of hydrogen include tritium and deuterium. Isotopes of carbon include $^{13}C$ and $^{14}C$. Isotopically labelled compounds of Formula (I) can generally be prepared by conventional techniques known to those skilled in the art or by processes analogous to those described in the accompanying Examples using appropriate isotopically labelled reagents in place of the non-labelled reagents previously employed.

A suitable pharmaceutically acceptable salt of a compound of the Formula (I) may be, for example, an acid addition salt. A suitable pharmaceutically acceptable salt of a compound of the Formula (I) may be, for example, an acid addition salt of a compound of the Formula (I), for example an acid-addition salt with an inorganic or organic acid. The compounds of the specification may be provided as the free base compound, i.e. in the non-salified state.

A further suitable pharmaceutically acceptable salt of a compound of the Formula (I) may be, for example, a salt formed within the human or animal body after administration of a compound of the Formula (I) to said human or animal body.

The compound of Formula (I) or pharmaceutically acceptable salt thereof may be prepared as a co-crystal solid form. It is to be understood that a pharmaceutically acceptable co-crystal of a compound of the Formula (I) or pharmaceutically acceptable salts thereof, form an aspect of the present specification.

For use in a pharmaceutical context it may be preferable to provide a compound of Formula (I) or a pharmaceutically acceptable salt thereof without large amounts of the other stereoisomeric forms being present.

The compound of Formula (I), or a pharmaceutically acceptable salt thereof, will normally be administered via the oral route though parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt or solvate thereof, or a solvate of such a salt, in a pharmaceutically acceptable dosage form may be possible. Depending upon the disorder and patient to be treated and the route of administration, the compositions may be administered at varying doses, for example in an oral dose of from 1 mg to 1,000 mg or from 1 mg to 2,000 mg.

The pharmaceutical formulations of the compound of Formula (I) described above may be prepared e.g. for parenteral, subcutaneous, intramuscular or intravenous administration.

The pharmaceutical formulations of the compound of Formula (I) described above may conveniently be administered in unit dosage form and may be prepared by any of the methods well-known in the pharmaceutical art, for example as described in Remington's Pharmaceutical Sciences, 17th ed., Mack Publishing Company, Easton, PA., (1985).

Pharmaceutical formulations suitable for oral administration may comprise one or more physiologically compatible carriers and/or excipients and may be in solid or liquid form. Tablets and capsules may be prepared with binding agents; fillers; lubricants; and surfactants. Liquid compositions may contain conventional additives such as suspending agents; emulsifying agents; and preservatives Liquid compositions may be encapsulated in, for example, gelatin to provide a unit dosage form. Solid oral dosage forms include tablets, two-piece hard shell capsules and soft elastic gelatin (SEG) capsules. An exemplary oral composition according to the specification comprises a compound of Formula (I) and at least one pharmaceutically acceptable excipient filled into a two-piece hard shell capsule or a soft elastic gelatin (SEG) capsule.

According to a further embodiment there is provided a compound of the Formula (I), or a pharmaceutically acceptable salt thereof, as defined hereinbefore, for use as a medicament in a warm-blooded animal such as man. In such embodiments the medicament may be for use in the treatment of conditions in which inhibition of IRAK4 is beneficial, for example in the treatment of cancer, inflammatory disease or autoinflammatory/autoimmune disease.

In embodiments wherein the compound for use is for the treatment of cancer, the cancer may be a haematologic malignancy selected from Waldenstrom's macroglobulinemia (WM), non-Hodgkin lymphoma (NHL), diffuse large B-cell lymphoma (DLBCL), primary central nervous system lymphoma (PCNSL), Splenic Marginal Zone Lymphoma (SMZL), small lymphocytic lymphoma (SLL), leukaemias (chronic lymphocytic leukaemia (CLL)) and monoclonal gammopathy of undetermined significance (MGUS-IgM+). In such embodiments the use may be as a single agent or in combination with at least one other agent administered separately, sequentially or simultaneously. In such embodiments the second agent may be selected from group comprising BCR inhibitors such as BTK inhibitors such as ibrutinib, acalabrutinib, zanubrutinib or tirabrutinib, PI3Kδ inhibitors, SYK inhibitors or immunotherapies.

In embodiments the compound for use in the treatment of cancer may be for use in the treatment of melanoma, optionally wherein the use may be in combination with at least one other agent administered separately, sequentially or simultaneously. In such embodiments the second agent may be a BTK inhibitor such as ibrutinib, acalabrutinib, zanubrutinib or tirabrutinib.

According to a further embodiment, there is provided the use of a compound of the Formula (I), or a pharmaceutically acceptable salt thereof, as defined hereinbefore, in the manufacture of a medicament for use in a warm-blooded animal such as man in the treatment of a condition in which inhibition of IRAK4 is beneficial. In such embodiments the medicament may be for the treatment of cancer, for example a haematologic malignancy selected from Waldenstrom's macroglobulinemia (WM), non-Hodgkin lymphoma (NHL), diffuse large B-cell lymphoma (DLBCL), primary central nervous system lymphoma (PCNSL), Splenic Marginal Zone Lymphoma (SMZL), small lymphocytic lymphoma (SLL), leukaemias (chronic lymphocytic leukaemia (CLL)) and monoclonal gammopathy of undetermined significance (MGUS-IgM+). In such embodiments the medicament may be for use may be as a single agent or in combination with at least one other agent or medicament administered separately, sequentially or simultaneously. In such embodiments the second agent or medicament may be selected from group comprising BCR inhibitors such as BTK inhibitors such as ibrutinib, acalabrutinib, zanubrutinib or tirabrutinib, PI3Kδ inhibitors, SYK inhibitors or immunotherapies.

In embodiments the medicament for use in the treatment of cancer may be for use in the treatment of melanoma, optionally wherein the use may be in combination with at least one other agent administered separately, sequentially or simultaneously. In such embodiments the second agent may be a BTK inhibitor such as ibrutinib, acalabrutinib, zanubrutinib or tirabrutinib.

In a further embodiment there is provided a method of treatment comprising administration of an effective amount of compound of the Formula (I), or a pharmaceutically acceptable salt thereof, as defined hereinbefore, to a patient in need thereof. In such embodiments the method of treatment may be for a condition in which inhibition of IRAK4 is beneficial. In such embodiments the method of treatment may be cancer, for example a haematologic malignancy selected from Waldenstrom's macroglobulinemia (WM), non-Hodgkin lymphoma (NHL), diffuse large B-cell lymphoma (DLBCL), primary central nervous system lymphoma (PCNSL), Splenic Marginal Zone Lymphoma (SMZL), small lymphocytic lymphoma (SLL), leukaemias (chronic lymphocytic leukaemia (CLL)) and monoclonal gammopathy of undetermined significance (MGUS-IgM+). In such embodiments the method of treatment may involve administration of the compound of Formula (I) as a single agent or in combination with at least one other agent or medicament administered separately, sequentially or simultaneously. In such embodiments the second agent or medicament may be selected from group comprising BCR inhibitors such as BTK inhibitors such as ibrutinib, acalabrutinib, zanubrutinib or tirabrutinib, PI3Kδ inhibitors, SYK inhibitors or immunotherapies.

In embodiments the method of treatment may be for the treatment of melanoma. In such embodiments the method may involve separate, sequential or simultaneous administration of a further agent or medicament. In such embodiments the second agent or medicament may be a BTK inhibitor such as ibrutinib, acalabrutinib, zanubrutinib or tirabrutinib.

In this specification, unless otherwise stated, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician. The effective amount will generally be in the range of 0.1 mg to 1,000 mg.

According to a further embodiment, there is provided a compound of the Formula (I), or a pharmaceutically acceptable salt thereof, as defined hereinbefore for use in providing an inhibitory effect on IRAK4 kinase.

According to a further embodiment, there is provided the use of a compound of the Formula (I), or a pharmaceutically acceptable salt thereof, as defined hereinbefore in the manufacture of a medicament for use in providing an inhibitory effect on IRAK4 kinase.

According to a further embodiment, there is also provided a method for providing an inhibitory effect on IRAK4 kinase which comprises administering an effective amount of a compound of the Formula (I), or a pharmaceutically acceptable salt thereof, as defined hereinbefore, to a patient in need thereof.

According to a further embodiment, there is provided a compound of the Formula (I), or a pharmaceutically acceptable salt thereof, as defined hereinbefore, for use in providing a selective inhibitory effect on IRAK4 kinase. In such cases the selective inhibitory effect indicates that the concentration of the compound of Formula (I) required to effect 50% inhibition in IRAK4 kinase activity in vitro is 10-fold, 100-fold or 1000-fold or more lower than that required to effect 50% inhibition of another kinase, for example another kinase that if inhibited gives rise to a toxic side effect.

According to a further embodiment, there is provided the use of a compound of the Formula (I), or a pharmaceutically acceptable salt thereof, as defined hereinbefore, in the manufacture of a medicament for use in providing a selective inhibitory effect on IRAK4 kinase.

According to a further embodiment, there is also provided a method for providing a selective inhibitory effect on IRAK4 kinase which comprises administering an effective amount of a compound of the Formula (I), or a pharmaceutically acceptable salt thereof, to a patient in need thereof.

Described herein are compounds that can inhibit IRAK4 kinase. In biochemical and cell based assays the compounds of the present specification are shown to be potent IRAK4 kinase inhibitors and may therefore be useful in the treatment of disorders mediated by IRAK4 kinase activity, in particular in the treatment of respiratory diseases such as asthma and chronic obstructive pulmonary disease (COPD), of inflammatory diseases and of autoinflammatory/autoimmune diseases such as systemic lupus erythematosus, rheumatoid arthritis, myositis, Sjögren's syndrome, systemic sclerosis, gout, endometriosis, atopic dermatitis and psoriasis.

In embodiments there is provided the use of a compound Formula (I) for the treatment of respiratory disease, optionally wherein the respiratory disease is asthma and chronic obstructive pulmonary disease (COPD).

In embodiments there is provided the use of a compound Formula (I) for the treatment of inflammatory diseases or autoinflammatory/autoimmune diseases such as systemic lupus erythematosus, rheumatoid arthritis, myositis, Sjögren's syndrome, systemic sclerosis, gout, endometriosis, atopic dermatitis and psoriasis.

In embodiments there is provided a method of treatment comprising administration of an effective amount of a compound of Formula (I) to a patient in need thereof, wherein the patient has a respiratory diseases, optionally wherein the respiratory disease is asthma and chronic obstructive pulmonary disease (COPD).

In embodiments there is provided a method of treatment comprising administration of an effective amount of a compound of Formula (I) to a patient in need thereof, wherein the patient has an inflammatory diseases or autoinflammatory/autoimmune diseases such as systemic lupus erythematosus, rheumatoid arthritis, myositis, Sjögren's syndrome, systemic sclerosis, gout, endometriosis, atopic dermatitis and psoriasis.

According to a further aspect of the specification, there is provided the use of a compound of the Formula (I), or a pharmaceutically acceptable salt thereof, as defined hereinbefore, in the manufacture of a medicament for use in the treatment of disorders mediated by IRAK4 kinase activity, in particular in the treatment of respiratory diseases such as asthma and chronic obstructive pulmonary disease (COPD), of inflammatory diseases and of autoinflammatory/autoimmune diseases such as systemic lupus erythematosus, rheumatoid arthritis, myositis, Sjögren's syndrome, systemic sclerosis, gout, endometriosis, atopic dermatitis and psoriasis.

According to a further aspect of the specification there is provided a kit comprising a pharmaceutical formulation comprising a compound of Formula (I) and instructions for use of the pharmaceutical formulation in the treatment of a condition or disease. In such embodiments, the condition or disease may be cancer, inflammatory disease or autoinflammatory/autoimmune disease. In cases where the instructions are for the treatment of cancer the cancer may be melanoma or a haematologic malignancy selected from Waldenstrom's macroglobulinemia (WM), non-Hodgkin lymphoma (NHL), diffuse large B-cell lymphoma (DLBCL), primary central nervous system lymphoma (PCNSL), Splenic Marginal Zone Lymphoma (SMZL), small lymphocytic lymphoma (SLL), leukaemias (chronic lymphocytic leukaemia (CLL)) and monoclonal gammopathy of undetermined significance (MGUS-IgM+). In instances wherein the kit is for the use of an, inflammatory disease or autoinflammatory/autoimmune disease the disease or condition may be selected from systemic lupus erythematosus, rheumatoid arthritis, myositis, Sjögren's syndrome, systemic sclerosis, gout, endometriosis, atopic dermatitis and psoriasis.

It will be appreciated that the following examples are provided so that the nature of the invention may be fully understood. It will also be appreciated that the following examples are not intended to limit the scope of the description in any way.

EXAMPLES

The following abbreviations are used:

| | |
|---|---|
| atm | Standard Atmosphere Pressure Unit |
| aq. | Aqueous |
| BOC | tert-Butyloxycarbonyl |
| CDI | 1,1'-Carbonyldiimidazole |
| CO | Carbon monoxide |
| Cs$_2$CO$_3$ | Cesium carbonate |
| DCE | 1,2-Dichloroethane |
| DCM | Dichloromethane |
| DIAD | Di-iso-propyl azodicarboxylate |
| DIPEA | N,N-Di-iso-propylethylamine |
| DMAP | 4-(Dimethylamino)pyridine |
| DMF | N,N-Dimethylformamide |
| DMSO | Dimethyl sulfoxide |
| dppf | 1,1'-Bis(diphenylphosphanyl)ferrocene |
| dppp | 1,3-Bis(diphenylphosphino)propane |
| EtOAc | Ethyl acetate |
| EtOH | Ethanol |
| FA | Formic acid |
| g | Gram(s) |
| h | Hour(s) |
| H$_2$ | Hydrogen |
| HATU | N-[(Dimethylamino)-1H-1,2,3-triazolo-[4,5-b]pyridin-1-ylmethylene]-N-methylmethanaminium hexafluorophosphate N-oxide |
| HCl | Hydrochloric acid |
| HPLC | High performance liquid chromatography |
| i-PrOH | Isopropanol |
| K$_2$CO$_3$ | Potassium carbonate |
| KF | Potassium fluoride |
| KOH | Potassium hydroxide |
| L | Liter(s) |
| LiOH | Lithium hydroxide |
| LiHMDS | Lithium bis(trimethylsilyl)amide |
| MeCN | Acetonitrile |
| MeOH | Methanol |
| min | Minute(s) |

-continued

| | |
|---|---|
| mL | Milliliter(s) |
| MsCl | Methanesulfonyl chloride |
| MTBE | Methyl tert-butyl ether |
| NaBH$_4$ | Sodium tetrahydridoborate |
| NaH | Sodium hydride |
| NaOH | Sodium hydroxide |
| NH$_3$ | Ammonia |
| NH$_4$HCO$_3$ | Ammonium bicarbonate |
| (NH$_4$)$_2$CO$_3$ | Ammonium carbonate |
| NH$_4$Cl | Ammonium chloride |
| NH$_4$OH | Ammonium hydroxide |
| nm | Nanometer |
| N$_2$ | Nitrogen |
| Pd(dppf)Cl$_2$ | [1,1'-Bis(diphenylphosphino)ferrocene] palladium(II) dichloride |
| Pd(dppf)Cl$_2$—CH$_2$Cl$_2$ | [1,1'-Bis(diphenylphosphino)ferrocene] palladium(II) dichloride dichloromethane complex |
| Pd(OAc)$_2$ | Palladium(II) acetate |
| Pd(OH)$_2$ | Palladium(II) hydroxide |
| PE | Petroleum ether |
| PMB | p-Methoxybenzyl |
| prep. | Preparative |
| i-PrOH | 2-Propanol |
| rt | Room temperature |
| sat. | Saturated |
| SEM | (Trimethylsilyl)ethoxymethyl |
| SFC | Supercritical fluid chromatography |
| T3P | Propanephosphonic acid anhydride |
| TFA | Trifluoroacetic acid |
| TEA | Triethylamine |
| TLC | Thin Layer Chromatography |
| TsCl | 4-Methylbenzenesulfonyl chloride |

Abbreviations used for analytical data, if not defined above, are consistent with the common usage in the field (see J Med Chem Standard Abbreviations and Acronyms http://pubsapp.acs.org/paragonplus/submission/jmcmar/jmcmar_abbreviations.pdf?).

The compound names provided below are generated using PerkinElmer ChemDraw Professional, Version 20.0.2.51. In instances where there is uncertainty as to the absolute stereochemistry, relative stereochemistry is specified as far as possible.

Compounds according to the specification can be prepared by methods well known to those skilled in the art, for example by directly using the routes outlined in Schemes 1 to 3 above, or by adapting those schemes as required to incorporate further functionality. Although specific routes and reagents are provided in the examples below, it will be appreciated that alternative starting materials and reagents can be used to deliver a variety of derivatives and/or reaction conditions. Accordingly, compounds across the claim scope can be readily prepared by routine adjustments or modifications using chemistry well know to the skilled in the art.

The compounds were analysed or purified by standard techniques. Except where otherwise noted, reactions are routinely run under inert atmosphere (e.g. nitrogen or argon).

PREPARATION OF INTERMEDIATES

Int 1: 5-Bromo-4-methoxy-2-nitrobenzaldehyde

5-Bromo-4-fluoro-2-nitrobenzaldehyde

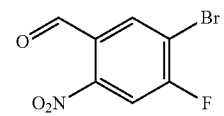

A solution of fuming nitric acid (12.0 mL, 0.3 mol) in concentrated sulfuric acid (25 mL) was added dropwise to 3-bromo-4-fluorobenzaldehyde (19.3 g, 95.1 mmol) in concentrated sulfuric acid (75 mL) at 0° C. The resulting yellow solution was slowly warmed to rt and stirred for 4 d. Then the reaction mixture was poured on crushed ice and the resulting precipitation was collected by filtration to afford 5-bromo-4-fluoro-2-nitrobenzaldehyde (22.6 g, 96%) as a yellow solid. m/z (ESI−), [M−H]⁻=245/247.

5-Bromo-4-methoxy-2-nitrobenzaldehyde (Int 1)

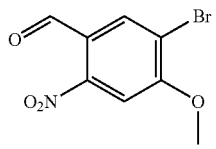

Sodium methoxide (10.9 g, 60.6 mmol) in MeOH (46 mL) was added to 5-bromo-4-fluoro-2-nitrobenzaldehyde (10.0 g, 40.3 mmol) in MeOH (150 mL) at rt. After stirring for 16 h the reaction was quenched with water (300 mL), the formed solid was filtered off and washed with water (100 mL) to afford 5-bromo-4-methoxy-2-nitrobenzaldehyde (6.6 g, 63%) as a pale-yellow solid. $^1$H NMR (300 MHz, DMSO-$d_6$) δ 10.03 (s, 1H), 8.15 (s, 1H), 7.78 (s, 1H), 4.04 (s, 3H).

Int 2: tert-Butyl ((1r,4r)-4-(5-bromo-6-methoxy-2H-indazol-2-yl)cyclohexyl)carbamate

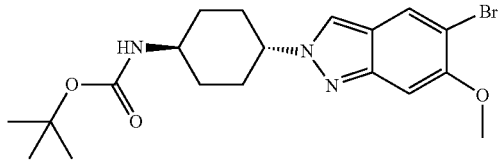 [SMILES: COc1cc2nn([C@H]3CC[C@H](NC(=O)OC(C)(C)C)CC3)cc2cc1Br]

To a solution of tert-butyl ((1r,4r)-4-aminocyclohexyl)carbamate (10.5 g, 49.0 mmol) in i-PrOH (200 mL) at rt was added 5-bromo-4-methoxy-2-nitrobenzaldehyde (Int 1) (12.7 g, 49.0 mmol) under N$_2$ atmosphere. The resulting mixture was stirred at 80° C. for 1 h, followed by the addition of tri-n-butylphosphine (29.7 g, 147.0 mmol). The reaction mixture was stirred at 80° C. for 13 h. The mixture was cooled to rt and concentrated under reduced pressure. The residue was purified by silica gel chromatography (eluting with 9-50% EtOAc in PE) to afford tert-butyl ((1r,4r)-4-(5-bromo-6-methoxy-2H-indazol-2-yl)cyclohexyl)carbamate (14.2 g, 68%) as a colorless solid. MS ESI, m/z=424/426 [M+H]⁺.

Int 3: Methyl 2-((1r,4r)-4-((tert-butoxycarbonyl)(methyl)amino)cyclohexyl)-6-methoxy-2H-indazole-5-carboxylate tert-Butyl ((1r,4r)-4-(5-bromo-6-methoxy-2H-indazol-2-yl)cyclohexyl)(methyl)carbamate

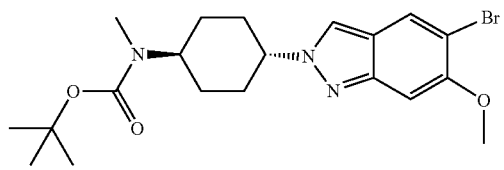 [SMILES: COc1cc2nn([C@H]3CC[C@H](N(C)C(=O)OC(C)(C)C)CC3)cc2cc1Br]

To a solution of tert-butyl ((1r,4r)-4-(5-bromo-6-methoxy-2H-indazol-2-yl)cyclohexyl)carbamate (Int 2) (4.2 g, 9.9 mmol) in DMF (50 mL) at 0° C. was added NaH (60 wt. %) (792 mg, 19.8 mmol). The resulting mixture was stirred at 25° C. for 30 min followed by the addition of iodomethane (1.24 mL, 19.8 mmol). The reaction mixture was stirred at rt for 13 h, then quenched with water (150 mL). The precipitate was filtered, washed with water (150 mL) and dried in vacuo to afford tert-butyl ((1r,4r)-4-(5-bromo-6-methoxy-2H-indazol-2-yl)cyclohexyl)(methyl)carbamate (4.36 g, 100%) as a colorless solid. $^1$H NMR (300 MHz, DMSO-$d_6$) δ 8.28 (s, 1H), 7.96 (s, 1H), 7.11 (s, 1H), 4.42 (ddt, 1H), 3.87-4.06 (m, 1H), 3.86 (s, 3H), 2.71 (s, 3H), 2.09-2.23 (m, 2H), 1.87-2.08 (m, 2H), 1.62-1.87 (m, 4H), 1.42 (s, 9H). MS ESI, m/z=438/440 (1:1) [M+H]⁺.

Methyl 2-((1r,4r)-4-((tert-butoxycarbonyl)(methyl)amino)cyclohexyl)-6-methoxy-2H-indazole-5-carboxylate (Int 3)

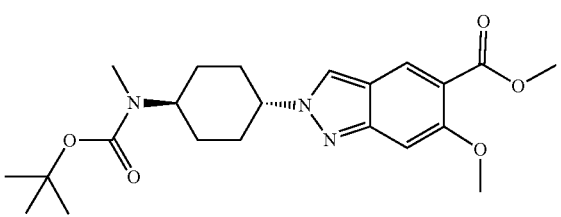 [SMILES: COC(=O)c1cc2cn([C@H]3CC[C@H](N(C)C(=O)OC(C)(C)C)CC3)nc2cc1OC]

A suspension of tert-butyl ((1r,4r)-4-(5-bromo-6-methoxy-2H-indazol-2-yl)cyclohexyl)(methyl)carbamate (4.3 g, 9.8 mmol), Pd(dppf)Cl$_2$ (714 mg, 1.0 mmol) and TEA (13.6 mL, 97.6 mmol) in MeOH (125 mL) was stirred under CO atmosphere at 15 atm and 100° C. for 15 h. The reaction mixture was cooled to rt and concentrated under reduced pressure. The residue was purified by silica gel chromatography (eluting with 30-50% EtOAc in PE) to afford methyl 2-((1r,4r)-4-((tert-butoxycarbonyl)(methyl)amino)cyclohexyl)-6-methoxy-2H-indazole-5-carboxylate (3.8 g, 93%) as a yellow solid. MS ESI, m/z=418 [M+H]⁺.

Int 4: Methyl 6-methoxy-2-((1r,4r)-4-(methylamino)cyclohexyl)-2H-indazole-5-carboxylate

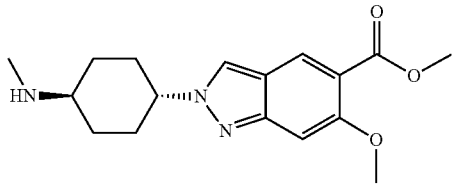

To a solution of methyl 2-((1r,4r)-4-((tert-butoxycarbonyl)(methyl)amino)cyclohexyl)-6-methoxy-2H-indazole-5-carboxylate (Int 3) (2.5 g, 6.0 mmol) in DCM (50 mL) was added 4N HCl in dioxane (15 ml, 59.9 mmol) at 25° C. under $N_2$ atmosphere. The resulting mixture was stirred at 25° C. for 18 h and then concentrated under reduced pressure to afford the HCl salt of methyl 6-methoxy-2-((1r,4r)-4-(methylamino)cyclohexyl)-2H-indazole-5-carboxylate (2.1 g, 100%), which was used without further purification. $^1$H NMR (400 MHz, DMSO-$d_6$) δ 8.77 (br. s, 1H), 8.43 (s, 1H), 8.05 (s, 1H), 7.01 (s, 1H), 4.36-4.56 (m, 1H), 3.78 (s, 3H), 3.74 (s, 3H), 3.53 (s, 3H), 2.95-3.14 (m, 1H), 2.11-2.26 (m, 4H), 1.92 (br. q, 2H), 1.60 (br. q, 2H). MS ESI, m/z=318 [M+H]$^+$.

Int 5: 2-((1r,4r)-4-((tert-Butoxycarbonyl)(methyl)amino)cyclohexyl)-6-methoxy-2H-indazole-5-carboxylic acid

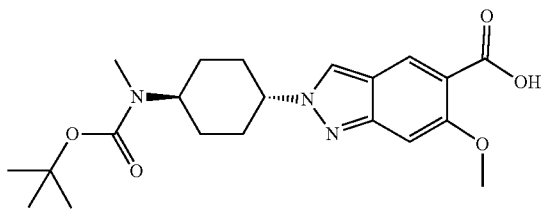 [SMILES: COc1cc2nn([C@H]3CC[C@H](N(C)C(=O)OC(C)(C)C)CC3)cc2cc1C(=O)O]

To a solution of methyl 2-((1r,4r)-4-((tert-butoxycarbonyl)(methyl)amino)cyclohexyl)-6-methoxy-2H-indazole-5-carboxylate (Int 3) (2.9 g, 6.9 mmol) in MeOH (50 mL)/water (25 mL) at rt was added NaOH (556 mg, 13.9 mmol). The resulting solution was stirred at 30° C. for 12 h. The reaction mixture was cooled to rt and acidified to pH ~6 with 4N HCl. The precipitate was filtered, washed with water (200 mL) and dried in vacuo to afford 2-((1r,4r)-4-((tert-butoxycarbonyl)(methyl)amino)cyclohexyl)-6-methoxy-2H-indazole-5-carboxylic acid (2.7 g, 95%) as a pale-yellow solid. MS ESI, m/z=404 [M+H]$^+$.

Int 6: 2-((1R,4r)-4-((R)-2-Hydroxy-N-methylpropanamido)cyclohexyl)-6-methoxy-2H-indazole-5-carboxylic acid Methyl 2-((1R,4r)-4-((R)-2-acetoxy-N-methylpropanamido)cyclohexyl)-6-methoxy-2H-indazole-5-carboxylate

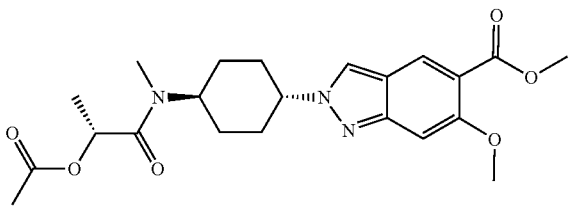 [SMILES: COC(=O)c1cc2cn([C@H]3CC[C@H](N(C)C(=O)[C@@H](C)OC(C)=O)CC3)nc2cc1OC]

To a solution of the HCl salt of methyl 6-methoxy-2-((1r,4r)-4-(methylamino)cyclohexyl)-2H-indazole-5-carboxylate (Int 4) (800 mg, 2.3 mmol) and TEA (945 μL, 6.8 mmol) in DCM (30 mL) at 0° C. under $N_2$ atmosphere was added (R)-1-chloro-1-oxopropan-2-yl acetate (511 mg, 3.4 mmol). The resulting solution was stirred at 25° C. for 15 h and then concentrated under reduced pressure. The residue was purified by C18-flash chromatography (eluting with 10-100% MeCN in water (0.1% NH$_4$OH)) to afford methyl 2-((1R,4r)-4-((R)-2-acetoxy-N-methylpropanamido)cyclohexyl)-6-methoxy-2H-indazole-5-carboxylate (910 mg, 93%) as a brown solid. $^1$H NMR (400 MHz, DMSO-$d_6$) (4:5 mixture of rotamers) δ 8.46/8.43 (s, 1H) (rotamers), 8.09/8.07 (s, 1H) (rotamers), 7.06/7.04 (s, 1H) (rotamers), 5.45/5.28 (q, 1H) (rotamers), 4.39-4.55 (m, 1H), 4.28-4.39/3.33-3.41 (m, 1H) (rotamers), 3.82 (s, 3H), 3.78 (s, 3H), 2.90/2.75 (s, 3H) (rotamers), 2.15-2.25 (m, 2H), 1.72-2.14 (m, 8H), 1.56-1.69 (m, 1H), 1.29-1.36 (m, 3H). MS ESI, m/z=432 [M+H]$^+$.

2-((1R,4r)-4-((R)-2-Hydroxy-N-methylpropanamido)cyclohexyl)-6-methoxy-2H-indazole-5-carboxylic acid (Int 6)

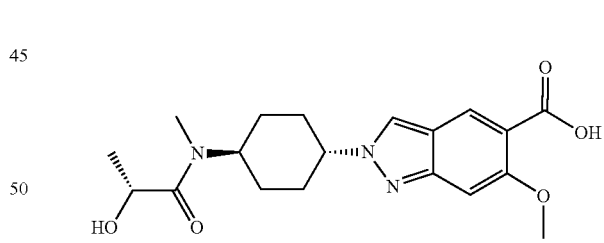

To a solution of methyl 2-((1R,4r)-4-((R)-2-acetoxy-N-methylpropanamido)cyclohexyl)-6-methoxy-2H-indazole-5-carboxylate (900 mg, 2.1 mmol) in MeOH (10 mL) at 25° C. under $N_2$ atmosphere was added LiOH monohydrate (525 mg, 12.5 mmol) in water (10 mL). The resulting solution was stirred at 25° C. for 16 h. The pH of the reaction mixture was adjusted to pH 7 with 1N HCl. The mixture was purified by C18-flash chromatography (eluting with 5-100% MeCN in water (0.1% FA)) to afford 2-((1R,4r)-4-((R)-2-hydroxy-N-methylpropanamido)cyclohexyl)-6-methoxy-2H-indazole-5-carboxylic acid (750 mg, 96%) as a brown solid. $^1$H NMR (400 MHz, DMSO-$d_6$) (4:5 mixture of rotamers) δ 8.43/8.40 (s, 1H) (rotamers), 8.25 (s, 1H), 8.04/8.03 (s, 1H) (rotamers), 7.01/7.00 (s, 1H) (rotamers), 4.38-4.58 (m, 2H), 4.32-4.41/3.93-4.02 (m, 1H) (rotamers), 3.81 (s, 3H), 2.90/ 2.76 (s, 3H) (rotamers), 1.94-2.24 (m, 4H), 1.71-1.94 (m, 3H), 1.59-1.71 (m, 1H), 1.17-1.26 (m, 3H). MS ESI, m/z=376 [M+H]$^+$.

Int 7: 2-((1r,4r)-4-Aminocyclohexyl)-6-methoxy-N-(1-methyl-2-oxo-1,2-dihydropyridin-3-yl)-2H-indazole-5-carboxamide Methyl 2-((1r,4r)-4-((tert-butoxycarbonyl)amino)cyclohexyl)-6-methoxy-2H-indazole-5-carboxylate

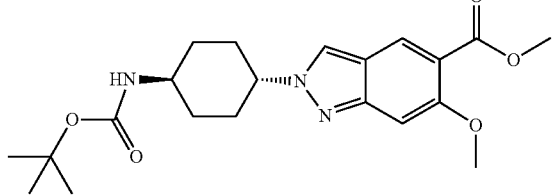

A mixture of tert-butyl ((1r,4r)-4-(5-bromo-6-methoxy-2H-indazol-2-yl)cyclohexyl)carbamate (Int 2) (1.5 g, 3.5 mmol), Pd(dppf)Cl$_2$—CH$_2$Cl$_2$ (577 mg, 0.7 mmol) and DIPEA (3.1 mL, 17.7 mmol) in MeOH (30 mL) was stirred in a sealed vessel under CO atmosphere at 15 atm, and then heated at 110° C. for 12 h. The reaction was carried out three times in parallel on the same scale. The combined reaction mixtures were concentrated under reduced pressure. The residue was purified by silica gel chromatography (eluting with 50% EtOAc in PE) to afford methyl 2-((1r,4r)-4-((tert-butoxycarbonyl)amino)cyclohexyl)-6-methoxy-2H-indazole-5-carboxylate (4.4 g, quantitative yield) as a grey solid. $^1$H NMR (300 MHz, DMSO-d$_6$) δ 8.44 (s, 1H), 8.08 (s, 1H), 7.06 (s, 1H), 6.86 (d, 1H), 4.30-4.50 (m, 1H), 3.82 (s, 3H), 3.79 (s, 3H), 3.28-3.44 (m, 1H), 2.03-2.19 (m, 2H), 1.82-2.03 (m, 4H), 1.40 (s, 11H). MS ESI, m/z=404 [M+H]$^+$.

2-((1r,4r)-4-((tert-Butoxycarbonyl)amino)cyclohexyl)-6-methoxy-2H-indazole-5-carboxylic acid

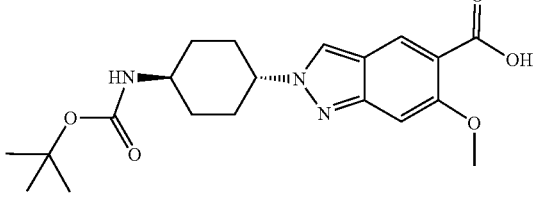

To a solution of methyl 2-((1r,4r)-4-((tert-butoxycarbonyl)amino)cyclohexyl)-6-methoxy-2H-indazole-5-carboxylate (1.5 g, 3.7 mmol) in water (5 mL) and MeOH (10 mL) was added NaOH (0.3 g, 7.4 mmol). The resulting mixture was stirred at 25° C. for 4 h before the pH of the mixture was adjusted to pH 5 with 0.1N HCl to cause precipitation. The precipitate was collected by filtration, washed with water (10 mL) and dried in vacuo to afford 2-((1r,4r)-4-((tert-butoxycarbonyl)amino)cyclohexyl)-6-methoxy-2H-indazole-5-carboxylic acid (1.4 g, 97%) as a pale-yellow solid, which was used without further purification. $^1$H NMR (400 MHz, DMSO-d$_6$) δ 12.41 (br. s, 1H), 8.42 (s, 1H), 8.06 (s, 1H), 7.03 (s, 1H), 6.86 (d, 1H), 4.29-4.52 (m, 1H), 3.81 (s, 3H), 2.03-2.17 (m, 2H), 1.86-2.03 (m, 4H), 1.39 (s, 9H), 1.32-1.49 (m, 2H). MS ESI, m/z=390 [M+H]$^+$.

tert-Butyl ((1r,4r)-4-(6-methoxy-5-((1-methyl-2-oxo-1,2-dihydropyridin-3-yl)carbamoyl)-2H-indazol-2-yl)cyclohexyl)carbamate

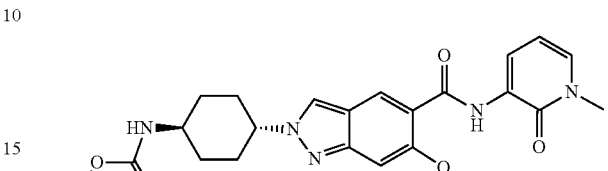

To a solution of 2-((1r,4r)-4-((tert-butoxycarbonyl)amino)cyclohexyl)-6-methoxy-2H-indazole-5-carboxylic acid (600 mg, 1.5 mmol), HATU (879 mg, 2.3 mmol) and DIPEA (807 µL, 4.6 mmol) in DMF (10 mL) was added 3-amino-1-methylpyridin-2(1H)-one (383 mg, 3.1 mmol). The reaction mixture was stirred at 25° C. for 5 h. The mixture was purified by C18-flash chromatography (eluting with 0-100% MeCN in water (0.1% NH$_4$OH)) to afford tert-butyl ((1r,4r)-4-(6-methoxy-5-((1-methyl-2-oxo-1,2-dihydropyridin-3-yl)carbamoyl)-2H-indazol-2-yl)cyclohexyl)carbamate (640 mg, 84%) as a light-yellow solid. $^1$H NMR (300 MHz, DMSO-d$_6$) δ 11.04 (s, 1H), 8.55 (s, 2H), 8.44 (dd, 1H), 7.42 (dd, 1H), 7.22 (s, 1H), 6.87 (d, 1H), 6.30 (t, 1H), 4.35-4.50 (m, 1H), 4.06 (s, 3H), 3.55 (s, 3H), 2.04-2.20 (m, 2H), 1.85-2.04 (m, 4H), 1.39 (s, 9H), 1.30-1.51 (m, 2H). MS ESI, m/z=496 [M+H]$^+$.

2-((1r,4r)-4-Aminocyclohexyl)-6-methoxy-N-(1-methyl-2-oxo-1,2-dihydropyridin-3-yl)-2H-indazole-5-carboxamide (Int 7)

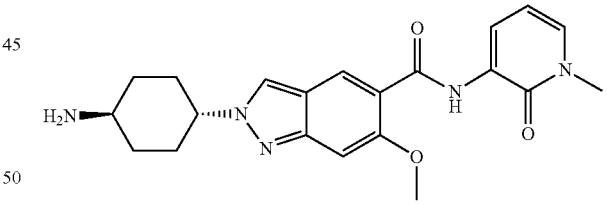

To a solution of tert-butyl ((1r,4r)-4-(6-methoxy-5-((1-methyl-2-oxo-1,2-dihydropyridin-3-yl)carbamoyl)-2H-indazol-2-yl)cyclohexyl)carbamate (620 mg, 1.3 mmol) in DCM (7 mL) was added 2N HCl in dioxane (6.3 mL, 12.5 mmol), and the resulting solution was stirred at 25° C. for 4 h. The mixture was concentrated under reduced pressure to afford the HCl salt of 2-((1r,4r)-4-aminocyclohexyl)-6-methoxy-N-(1-methyl-2-oxo-1,2-dihydropyridin-3-yl)-2H-indazole-5-carboxamide (565 mg, quantitative yield) as a colorless solid. $^1$H NMR (300 MHz, DMSO-d$_6$) (a HCl salt) δ 11.03 (s, 1H), 8.58 (s, 1H), 8.56 (s, 1H), 8.43 (dd, 1H), 8.36 (br d, 3H), 7.43 (dd, 1H), 7.20 (s, 1H), 6.30 (t, 1H), 4.42-4.57 (m, 1H), 4.06 (s, 3H), 3.55 (s, 3H), 3.02-3.22 (m, 1H), 2.08-2.29 (m, 4H), 1.90-2.08 (m, 2H), 1.52-1.73 (m, 2H). MS ESI, m/z=396 [M+H]$^+$.

Int 8: (1s,4s)-4-(6-Methoxy-5-((1-methyl-2-oxo-1,2-dihydropyridin-3-yl)carbamoyl)-2H-indazol-2-yl)cyclohexyl methanesulfonate (1s,4s)-4-(5-Bromo-6-methoxy-2H-indazol-2-yl)cyclohexan-1-ol

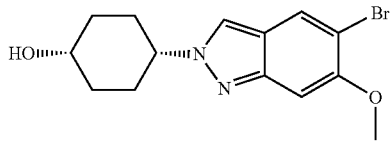 [SMILES: COc1cc2nn([C@H]3CC[C@@H](O)CC3)cc2cc1Br]

(1s,4s)-4-Aminocyclohexan-1-ol (6.0 g, 52.1 mmol) was added to 5-bromo-4-methoxy-2-nitrobenzaldehyde (Int 1) (13.8 g, 53.1 mmol) in i-PrOH (500 mL) under $N_2$ atmosphere. The resulting mixture was stirred at 80° C. for 15 h. Then the reaction mixture was cooled to room temperature and tributylphosphane (31.6 g, 156.3 mmol) was added to the mixture. The resulting mixture was stirred at 80° C. for 6 h and then concentrated under reduced pressure. The crude was purified by silica chromatography (eluting with 70% EtOAc in PE) to afford (1s,4s)-4-(5-bromo-6-methoxy-2H-indazol-2-yl)cyclohexan-1-ol (12 g, 71%) as a colorless solid. MS ESI, m/z=325/327 [M+H]$^+$.

Methyl 2-((1s,4s)-4-hydroxycyclohexyl)-6-methoxy-2H-indazole-5-carboxylate

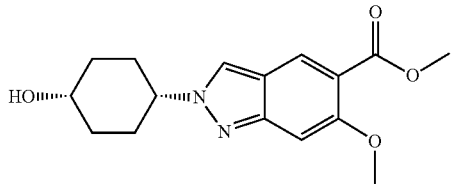 [SMILES: COC(=O)c1cc2cn([C@H]3CC[C@@H](O)CC3)nc2cc1OC]

(1s,4s)-4-(5-Bromo-6-methoxy-2H-indazol-2-yl)cyclohexan-1-ol (10 g, 30.8 mmol), TEA (21.4 mL, 153.8 mmol) and Pd(dppf)Cl$_2$—CH$_2$Cl$_2$ (5.0 g, 6.2 mmol) in MeOH (200 mL) were stirred under an atmosphere of CO at 15 atm and 110° C. for 15 h. The mixture was cooled to rt and concentrated under reduced pressure. The crude was purified by silica chromatography (eluting with 1% MeOH in DCM) to afford methyl 2-((1s,4s)-4-hydroxycyclohexyl)-6-methoxy-2H-indazole-5-carboxylate (8.0 g, 85%) as a brown oil. MS ESI, m/z=305 [M+H]$^+$.

2-((1s,4s)-4-Hydroxycyclohexyl)-6-methoxy-2H-indazole-5-carboxylic acid

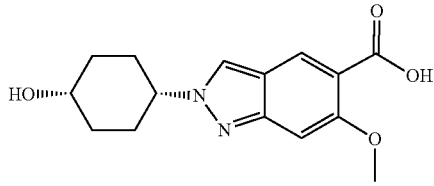 [SMILES: COc1cc2nn([C@H]3CC[C@@H](O)CC3)cc2cc1C(=O)O]

2M aq. NaOH solution (50 ml, 100.0 mmol) was added to methyl 2-((1s,4s)-4-hydroxycyclohexyl)-6-methoxy-2H-indazole-5-carboxylate (8.0 g, 26.1 mmol) in MeOH (100 mL). The resulting mixture was stirred at rt for 15 h. Then the reaction mixture was diluted with water (700 mL) and washed with EtOAc (2×600 mL). The aqueous phase was collected and the pH was adjusted to pH 4 with aq. 2M HCl. The aq. phase was extracted with EtOAc (1×600 mL) and DCM (2×500 mL). The organic layers were combined, dried over Na$_2$SO$_4$ and concentrated under reduced pressure to afford 2-((1s,4s)-4-hydroxycyclohexyl)-6-methoxy-2H-indazole-5-carboxylic acid (7.0 g, 92%) as an orange solid which was used without further purification. MS ESI, m/z=291 [M+H]$^+$.

2-((1s,4s)-4-Hydroxycyclohexyl)-6-methoxy-N-(1-methyl-2-oxo-1,2-dihydropyridin-3-yl)-2H-indazole-5-carboxamide

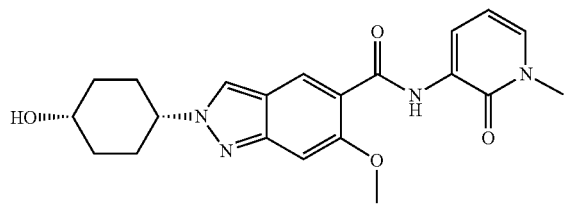 [SMILES: COc1cc2nn([C@H]3CC[C@@H](O)CC3)cc2cc1C(=O)Nc1cccn(C)c1=O]

To a solution of 2-((1s,4s)-4-hydroxycyclohexyl)-6-methoxy-2H-indazole-5-carboxylic acid (7.0 g, 23.9 mmol) and HATU (10.9 g, 28.7 mmol) in DMF (100 mL) at rt under $N_2$ atmosphere was added DIPEA (12.5 mL, 71.8 mmol). The resulting solution was stirred for 10 min, followed by the addition of 3-amino-1-methylpyridin-2(1H)-one hydrochloride (4.4 g, 27.5 mmol). The reaction mixture was stirred at rt for 15 h and then filtered. The solid was washed with water (50 mL) to afford 2-((1s,4s)-4-hydroxycyclohexyl)-6-methoxy-N-(1-methyl-2-oxo-1,2-dihydropyridin-3-yl)-2H-indazole-5-carboxamide (7.5 g, 79%) as a light yellow solid. $^1$H NMR (400 MHz, DMSO-d$_6$) δ 11.04 (s, 1H), 8.57 (s, 1H), 8.55 (s, 1H), 8.45 (dd, 1H), 7.41 (dd, 1H), 7.21 (s, 1H), 6.30 (t, 1H), 4.51 (d, 1H), 4.44 (tt, 1H), 4.07 (s, 3H), 3.84-3.93 (m, 1H), 3.55 (s, 3H), 2.29 (qd, 2H), 1.82-1.94 (m, 2H), 1.72-1.82 (m, 2H), 1.57-1.70 (m, 2H). MS ESI, m/z=397 [M+H]$^+$.

(1s,4s)-4-(6-Methoxy-5-((1-methyl-2-oxo-1,2-dihydropyridin-3-yl)carbamoyl)-2H-indazol-2-yl)cyclohexyl methanesulfonate (Int 8)

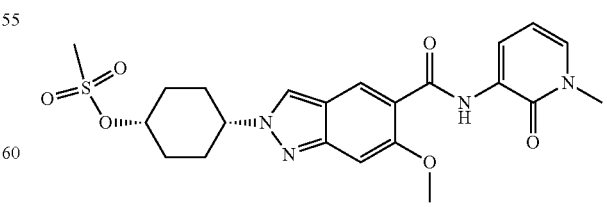

MsCl (2.5 mL, 31.5 mmol) was added dropwise to a solution of 2-((1s,4s)-4-hydroxycyclohexyl)-6-methoxy-N-(1-methyl-2-oxo-1,2-dihydropyridin-3-yl)-2H-indazole-5-carboxamide (5.0 g, 12.6 mmol) and TEA (10.6 mL, 75.7 mmol) in DCM (300 mL) at 0° C. under N₂ atmosphere. The resulting solution was stirred at rt for 15 h. Then, the reaction mixture was quenched with MeOH (10 mL), filtered, and concentrated under reduced pressure. The residue was purified by silica gel chromatography (eluting with 2% MeOH in DCM) to afford (1s,4s)-4-(6-methoxy-5-((1-methyl-2-oxo-1,2-dihydropyridin-3-yl)carbamoyl)-2H-indazol-2-yl)cyclohexyl methanesulfonate (4.10 g, 69%) as a pink solid. ¹H NMR (400 MHz, DMSO-d₆) δ 11.04 (s, 1H), 8.59 (s, 1H), 8.57 (s, 1H), 8.45 (dd, 1H), 7.42 (dd, 1H), 7.25 (s, 1H), 6.30 (t, 1H), 4.94-5.04 (m, 1H), 4.60 (tt, 1H), 4.07 (s, 3H), 3.56 (s, 3H), 3.23 (s, 3H), 1.96-2.29 (m, 6H), 1.82-1.96 (m, 2H). MS ESI, m/z=475 [M+H]⁺.

EXAMPLES

6-Methoxy-N-(1-methyl-2-oxo-1,2-dihydropyridin-3-yl)-2-((1r,4r)-4-(N-methylacetamido)cyclohexyl)-2H-indazole-5-carboxamide (Example 1)

Methyl 6-methoxy-2-((1r,4r)-4-(N-methylacetamido)cyclohexyl)-2H-indazole-5-carboxylate

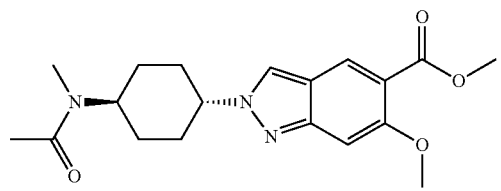 [SMILES: COC(=O)c1cc2cn([C@H]3CC[C@H](N(C)C(C)=O)CC3)nc2cc1OC]

To a solution of the HCl salt of methyl 6-methoxy-2-((1r,4r)-4-(methylamino)cyclohexyl)-2H-indazole-5-carboxylate (Int 4) (410 mg, 1.2 mmol) and TEA (485 μL, 3.5 mmol) in DCM (8 mL) was added acetic anhydride (219 μL, 2.3 mmol). The resulting mixture was stirred at 25° C. for 2 h and then diluted with DCM (25 mL), and washed sequentially with sat. aq. NaHCO₃ (20 mL), brine (25 mL). The organic layer was dried over Na₂SO₄, filtered and concentrated under reduced pressure to afford methyl 6-methoxy-2-((1r,4r)-4-(N-methylacetamido)cyclohexyl)-2H-indazole-5-carboxylate (415 mg, 100%) as a brown oil, which was used in the next step without further purification. ¹H NMR (300 MHz, DMSO-d₆) (3:2 mixture of rotamers) δ 8.46/8.44 (s, 1H) (rotamers), 8.09/8.08 (s, 1H) (rotamers), 7.05/7.04 (s, 1H) (rotamers), 4.34-4.56/3.68-3.90 (m, 2H) (rotamers), 3.81 (s, 3H), 3.78 (s, 3H), 2.85/2.72 (s, 3H) (rotamers), 1.90-2.19 (m, 7H), 1.57-1.88 (m, 4H). MS ESI, m/z=360 [M+H]⁺.

6-Methoxy-2-((1r,4r)-4-(N-methylacetamido)cyclohexyl)-2H-indazole-5-carboxylic acid

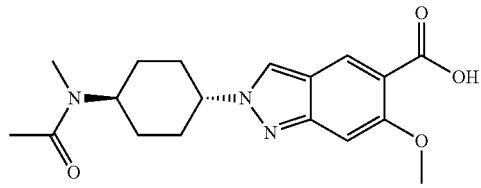 [SMILES: COc1cc2nn([C@H]3CC[C@H](N(C)C(C)=O)CC3)cc2cc1C(=O)O]

To a solution of methyl 6-methoxy-2-((1r,4r)-4-(N-methylacetamido)cyclohexyl)-2H-indazole-5-carboxylate (Int 5) (400 mg, 1.1 mmol) in MeOH/water (9 mL, 2:1) at 25° C. under N₂ atmosphere was added NaOH (89 mg, 2.23 mmol). The resulting solution was stirred at 25° C. for 2 h, then acidified with 2N HCl to pH 6, and concentrated under reduced pressure. The residue was purified by C18-flash chromatography (eluting with 0-80% MeCN in water (0.1% FA)) to afford 6-methoxy-2-((1r,4r)-4-(N-methylacetamido)cyclohexyl)-2H-indazole-5-carboxylic acid (384 mg, 100%) as a colorless solid. ¹H NMR (300 MHz, DMSO-d₆) (3:2 mixture of rotamers) δ 12.44 (br. s, 1H), 8.44/8.42 (s, 1H) (rotamers), 8.08/8.06 (s, 1H) (rotamers), 7.02/7.01 (s, 1H) (rotamers), 4.34-4.54/3.70-3.81 (m, 2H) (rotamers), 3.82 (s, 3H), 2.85/2.72 (s, 3H) (rotamers), 2.12-2.24 (m, 2H), 1.89-2.12 (m, 5H), 1.68-1.89 (m, 3H), 1.57-1.68 (m, 1H). MS ESI, m/z=346 [M+H]⁺.

6-Methoxy-N-(1-methyl-2-oxo-1,2-dihydropyridin-3-yl)-2-((1r,4r)-4-(N-methylacetamido)cyclohexyl)-2H-indazole-5-carboxamide, Example 1

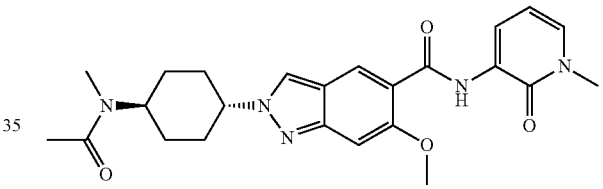

To a solution of 6-methoxy-2-((1r,4r)-4-(N-methylacetamido)cyclohexyl)-2H-indazole-5-carboxylic acid (100 mg, 0.29 mmol), DIPEA (152 μL, 0.87 mmol) and 3-amino-1-methylpyridin-2(1H)-one (53.9 mg, 0.43 mmol) in DCM (3 mL) at 25° C. under N₂ atmosphere was added T3P® (50 wt. % in EtOAc) (553 mg, 0.87 mmol). The resulting solution was stirred at 25° C. for 2 h and then concentrated under reduced pressure. The residue was purified by C18-flash chromatography (eluting with 0-80% MeCN in water (0.1% FA)) and further by prep. HPLC (YMC-Actus Triart C18 ExRS 5 μm 30×150 mm; elution gradient 12-45% MeCN in water (10 mM (NH₄)₂CO₃+0.1% NH₄OH) over 7 min; 60 mL/min) to afford 6-methoxy-N-(1-methyl-2-oxo-1,2-dihydropyridin-3-yl)-2-((1r,4r)-4-(N-methylacetamido)cyclohexyl)-2H-indazole-5-carboxamide (93 mg, 71%), Example 1, as a pale yellow solid. ¹H NMR (400 MHz, DMSO-d₆) (3:2 mixture of rotamers) δ 11.04 (s, 1H), 8.53-8.60 (m, 2H), 8.45 (dd, 1H), 7.43 (dd, 1H), 7.22/7.20 (s, 1H) (rotamers), 6.31 (t, 1H), 4.45-4.55 (m, 1H), 4.36-4.45/3.72-3.85 (m, 1H) (rotamers), 4.07 (s, 3H), 3.56 (s, 3H), 2.86/2.72 (s, 3H) (rotamers), 2.15-2.25 (m, 2H), 1.94-2.15 (m, 5H), 1.70-1.93 (m, 3H), 1.58-1.70 (m, 1H). MS ESI, m/z=452 [M+H]⁺.

6-Methoxy-N-(1-methyl-2-oxo-1,2-dihydropyridin-3-yl)-2-((1R,2R)-2-methyl-4-(N-methylacetamido)cyclohexyl)-2H-indazole-5-carboxamide—Isomer 1 (Example 2) & Isomer 2

Example 3 rac-(7R,8R)—N-Benzyl-7-methyl-1,4-dioxaspiro[4.5]decan-8-amine

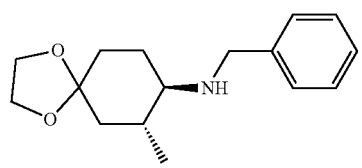 [SMILES: C[C@@H]1CC2(CC[C@H]1NCc1ccccc1)OCCO2]

And Enantiomer

To a solution of 7-methyl-1,4-dioxaspiro[4.5]decan-8-one (3.0 g, 17.6 mmol) and phenylmethanamine (2.8 g, 26.4 mmol) in toluene (50 mL) under $N_2$ atmosphere was added 4-methylbenzenesulfonic acid monohydrate (335 mg, 1.8 mmol). The resulting solution was stirred at 120° C. for 15 h. The reaction mixture was allowed to cool to rt and was concentrated under reduced pressure to give the crude imine intermediate. To a solution of the imine in MeOH (60 mL) at −60° C. was added $NaBH_4$ (0.6 g, 15.8 mmol) portionwise over a period of 5 min under $N_2$ atmosphere. The resulting mixture was stirred at −60° C. for 1 h, then slowly warmed to rt and stirred for 3 h. Five batches of crude product solution where prepared in parallel as described above and combined before the purification. The reaction mixture was concentrated under reduced pressure, dissolved with EtOAc (500 mL) and washed with brine (300 mL×3). The organic layer was dried over $Na_2SO_4$, filtered and was concentrated under reduced pressure. The residue was purified by C18-flash chromatography (eluting with 0-100% MeCN in water (0.05% $NH_4HCO_3$)) to afford rac-(7R,8R)-N-benzyl-7-methyl-1,4-dioxaspiro[4.5]decan-8-amine (8.1 g, 35%) as an orange oil. MS ESI, m/z=262 [M+H]$^+$.

rac-(7R,8R)-7-Methyl-1,4-dioxaspiro[4.5]decan-8-amine

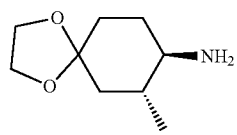

And Enantiomer

To a solution of rac-(7R,8R)-N-benzyl-7-methyl-1,4-dioxaspiro[4.5]decan-8-amine (8.1 g, 31.0 mmol) in MeOH (100 mL) under $N_2$ atmosphere was added $Pd(OH)_2$ on carbon (20 wt. %) (872 mg, 1.2 mmol). The resulting suspension was stirred at rt under hydrogen at 2 atm for 15 h. The reaction mixture was filtered through celite, and the celite cake was washed with MeOH (150 mL). The combined MeOH solution was concentrated under reduced pressure to afford crude rac-(7R,8R)-7-methyl-1,4-dioxaspiro[4.5]decan-8-amine (5.0 g) as a brown oil, which was used without further purification.

5-Bromo-6-methoxy-2-((7R,8R)-7-methyl-1,4-dioxaspiro[4.5]decan-8-yl)-2H-indazole

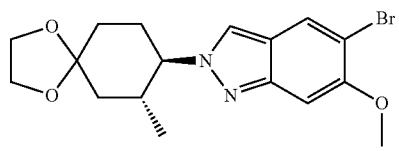 [SMILES: COc1cc2nn([C@@H]3CCC4(C[C@H]3C)OCCO4)cc2cc1Br]

To a solution of 5-bromo-4-methoxy-2-nitrobenzaldehyde (Int 1) (10.6 g, 40.9 mmol) in i-PrOH (200 mL) at rt was added crude rac-(7R,8R)-7-methyl-1,4-dioxaspiro[4.5]decan-8-amine (7.0 g) under $N_2$ atmosphere. The resulting mixture was stirred at 80° C. for 2 h, then cooled to rt, followed by the addition of tri-n-butylphosphine (41.4 g, 204.4 mmol). The reaction mixture was stirred at 80° C. for 24 h. The mixture was allowed to cool to rt and concentrated under reduced pressure. The residue was purified by silica gel chromatography (eluting with 0-10% MeOH in DCM) and further by C18-flash chromatography (eluting with 0-100% MeCN in water (0.05% $NH_4OH$)) to afford rac-5-bromo-6-methoxy-2-((7R,8R)-7-methyl-1,4-dioxaspiro[4.5]decan-8-yl)-2H-indazole as a yellow solid. This material was purified by chiral prep. SFC (Chiralpak® IG, 5 μm 50×250 mm; isocratic with 50% MeOH (0.1% 2N $NH_3$-MeOH) in $CO_2$ (35° C., 100 bar)) to afford 5-bromo-6-methoxy-2-((7R,8R)-7-methyl-1,4-dioxaspiro[4.5]decan-8-yl)-2H-indazole (3.0 g, 19%, 100% ee) as a gray solid. $^1$H NMR (300 MHz, DMSO-$d_6$) δ 8.25 (d, 1H), 7.96 (s, 1H), 7.12 (s, 1H), 4.13 (td, 1H), 3.87-3.99 (m, 4H), 3.87 (s, 3H), 2.26-2.43 (m, 1H), 2.19 (td, 1H), 1.75-1.96 (m, 3H), 1.68 (td, 1H), 1.46 (t, 1H), 0.52 (d, 3H). MS ESI, m/z=381/383 [M+H]$^+$.

(3R,4R)-4-(5-Bromo-6-methoxy-2H-indazol-2-yl)-3-methylcyclohexan-1-one

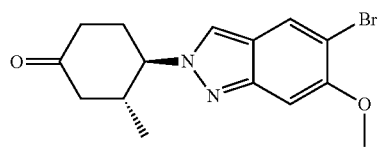 [SMILES: COc1cc2nn([C@@H]3CCC(=O)C[C@H]3C)cc2cc1Br]

To a solution of 5-bromo-6-methoxy-2-((7R,8R)-7-methyl-1,4-dioxaspiro[4.5]decan-8-yl)-2H-indazole (185 mg, 0.5 mmol) in THF (5 mL) at rt under $N_2$ atmosphere was added aq. 4N HCl (5 mL, 20.0 mmol). The reaction mixture was stirred at rt for 12 h. The reaction mixture was neutralized with aq. $NH_4OH$ solution to pH~7 and then concentrated under reduced pressure. The residue was purified by silica gel chromatography (eluting with 0-50% EtOAc in PE) to afford (3R,4R)-4-(5-bromo-6-methoxy-2H-indazol-2-yl)-3-methylcyclohexan-1-one (160 mg, 98%) as a yellow oil. MS ESI, m/z=337/339 [M+H]$^+$.

(3R,4R)-4-(5-Bromo-6-methoxy-2H-indazol-2-yl)-N,3-dimethylcyclohexan-1-amine

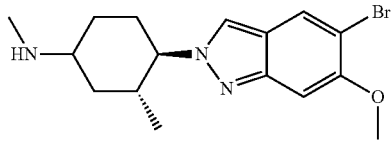

To a solution of (3R,4R)-4-(5-bromo-6-methoxy-2H-indazol-2-yl)-3-methylcyclohexan-1-one (180 mg, 0.5 mmol) and methanamine (33 wt. % in MeOH) (754 mg, 8.0 mmol) in DCE (6 mL) was added sodium triacetoxyborohydride (339 mg, 1.6 mmol). The resulting mixture was stirred at rt for 2 h, then quenched with water (1 mL) and concentrated under reduced pressure. The residue was purified by C18-flash chromatography (eluting with 0-100% MeCN in water (2% NH$_4$OH)) to afford (3R,4R)-4-(5-bromo-6-methoxy-2H-indazol-2-yl)-N,3-dimethylcyclohexan-1-amine (150 mg, 80%) as a colorless solid. MS ESI, m/z=337/339 (1:1) [M+H]$^+$.

N-((3R,4R)-4-(5-Bromo-6-methoxy-2H-indazol-2-yl)-3-methylcyclohexyl)-N-methylacetamide

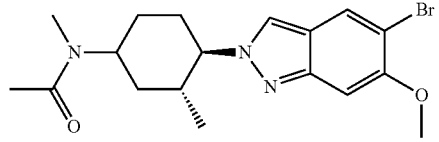 [SMILES: COc1cc2nn([C@@H]3CCC(N(C)C(C)=O)C[C@H]3C)cc2cc1Br]

To a solution of (3R,4R)-4-(5-bromo-6-methoxy-2H-indazol-2-yl)-N,3-dimethylcyclohexan-1-amine (140 mg, 0.4 mmol) and TEA (222 µL, 1.6 mmol) in DCM (5 mL) was added acetic anhydride (81 mg, 0.8 mmol). The resulting mixture was stirred at rt for 1 h. Then, the reaction mixture was concentrated under reduced pressure and purified by C18-flash chromatography (eluting with 0-100% MeCN in water (0.1% FA)) to afford N-((3R,4R)-4-(5-bromo-6-methoxy-2H-indazol-2-yl)-3-methylcyclohexyl)-N-methylacetamide (125 mg, 80%) as a yellow solid. MS ESI, m/z=394/396 (1:1) [M+H]$^+$.

Methyl 6-methoxy-2-((1R,2R)-2-methyl-4-(N-methylacetamido)cyclohexyl)-2H-indazole-5-carboxylate

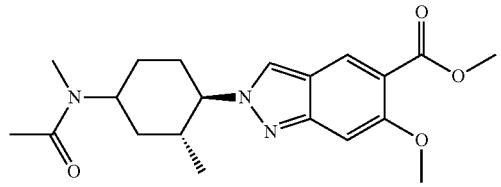 [SMILES: COC(=O)c1cc2cn([C@@H]3CCC(N(C)C(C)=O)C[C@H]3C)nc2cc1OC]

A mixture of N-((3R,4R)-4-(5-bromo-6-methoxy-2H-indazol-2-yl)-3-methylcyclohexyl)-N-methylacetamide (120 mg, 0.3 mmol), Pd(dppf)Cl$_2$ (45 mg, 0.06 mmol) and DIPEA (266 µL, 1.5 mmol) in MeOH (10 mL) was stirred in a sealed vessel under CO atmosphere at 15 atm, and then heated at 110° C. for 15 h. The reaction mixture was concentrated under reduced pressure. The residue was purified by C18-flash chromatography (eluting with 0-100% MeCN in water (0.05% NH$_4$OH)) to afford methyl 6-methoxy-2-((1R,2R)-2-methyl-4-(N-methylacetamido)cyclohexyl)-2H-indazole-5-carboxylate (105 mg, 92%) as a wax-like yellow solid. MS ESI, m/z=374 [M+H]$^+$.

6-Methoxy-2-((1R,2R)-2-methyl-4-(N-methylacetamido)cyclohexyl)-2H-indazole-5-carboxylic acid

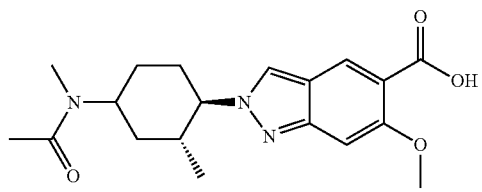 [SMILES: COc1cc2nn([C@@H]3CCC(N(C)C(C)=O)C[C@H]3C)cc2cc1C(=O)O]

To a solution of methyl 6-methoxy-2-((1R,2R)-2-methyl-4-(N-methylacetamido)cyclohexyl)-2H-indazole-5-carboxylate (102 mg, 0.3 mmol) in MeOH (3 mL) at rt under N$_2$ atmosphere was added LiOH (20 mg, 0.8 mmol) in water (10 mL). The resulting solution was stirred at rt for 2 h and then adjusted to pH 6 with 2N HCl. The reaction mixture was purified directly by C18-flash chromatography (eluting with 5-100% MeCN in water (0.05% FA)) to afford 6-methoxy-2-((1R,2R)-2-methyl-4-(N-methylacetamido)cyclohexyl)-2H-indazole-5-carboxylic acid (98 mg, 100%) as a colorless solid. MS ESI, m/z=360 [M+H]$^+$.

6-Methoxy-N-(1-methyl-2-oxo-1,2-dihydropyridin-3-yl)-2-((1R,2R)-2-methyl-4-(N-methylacetamido)cyclohexyl)-2H-indazole-5-carboxamide—Isomer 1, Example 2 & Isomer 2, Example 3

ISOMER 1

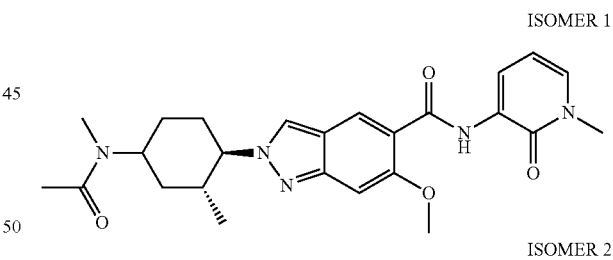

ISOMER 2

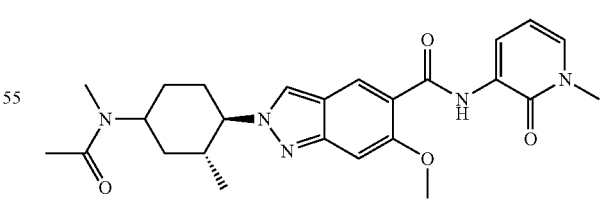

To a solution of 6-methoxy-2-((1R,2R)-2-methyl-4-(N-methylacetamido)cyclohexyl)-2H-indazole-5-carboxylic acid (88 mg, 0.2 mmol), DIPEA (171 µL, 1.0 mmol) and 3-amino-1-methylpyridin-2(1H)-one hydrochloride (79 mg, 0.5 mmol) in DCM (5 mL) at 25° C. under N$_2$ atmosphere was added T3P® (50 wt. % in EtOAc) (312 mg, 0.5 mmol). The resulting solution was stirred at rt for 2 h before it was concentrated under reduced pressure. The residue was purified by C18-flash chromatography (eluting with 0-100% MeCN in water (0.05% FA)) and then further separated by chiral prep. HPLC (Chiralpak® IF, 5 μm 20 mm×250 mm; isocratic with 50% MTBE (0.5% 2M NH₃-MeOH solution) in EtOH for 26 min; 20.0 mL/min) to afford 6-methoxy-N-(1-methyl-2-oxo-1,2-dihydropyridin-3-yl)-2-((1R,2R)-2-methyl-4-(N-methylacetamido)cyclohexyl)-2H-indazole-5-carboxamide—Isomer 1 (40 mg, 35%, 100% ee) and 6-methoxy-N-(1-methyl-2-oxo-1,2-dihydropyridin-3-yl)-2-((1R,2R)-2-methyl-4-(N-methylacetamido)cyclohexyl)-2H-indazole-5-carboxamide—Isomer 2 (14 mg, 12%, 99.6% ee), both as colorless solids. Isomer 1 (Example 2): ¹H NMR (400 MHz, DMSO-d₆) (3:2 mixture of rotamers) δ 11.04 (s, 1H), 8.68 (s, 1H), 8.59 (s, 1H), 8.45 (dd, 1H), 7.43 (dd, 1H), 7.25 (s, 1H), 6.31 (t, 1H), 4.52-4.70/3.91-4.05 (m, 1H) (rotamers), 4.30-4.48 (m, 1H), 4.08 (s, 3H), 3.56 (s, 3H), 2.85/2.70 (br. s, 4H) (rotamers), 0.89-2.38 (m, 12H). MS ESI, m/z=466 [M+H]⁺. Isomer 2 (Example 3): ¹H NMR (400 MHz, DMSO-d₆) (3:2 mixture of rotamers) δ 11.04 (s, 1H), 8.57-8.60 (m, 1H), 8.57/8.55 (s, 1H) (rotamers), 8.45 (dd, 1H), 7.43 (dd, 1H), 7.24/7.21 (s, 1H) (rotamers), 6.31 (t, 1H), 4.45-4.55 (m, 1H), 4.45-4.55/3.81-3.92 (m, 1H) (rotamers), 4.09-4.18 (m, 1H), 4.07 (s, 3H), 3.56 (s, 3H), 2.86/2.72 (s, 3H) (rotamers), 1.94-2.28 (m, 6H), 1.56-1.90 (m, 4H), 0.53-0.63 (m, 3H). MS ESI, m/z=466 [M+H]⁺.

6-Methoxy-N-(1-methyl-2-oxo-1,2-dihydropyridin-3-yl)-2-((1R,2S,4R)-2-methyl-4-(N-methylacetamido)cyclohexyl)-2H-indazole-5-carboxamide (Example 4)

6-Methoxy-N-(1-methyl-2-oxo-1,2-dihydropyridin-3-yl)-2-((1S,2R,4S)-2-methyl-4-(N-methylacetamido)cyclohexyl)-2H-indazole-5-carboxamide (Example 5)

rel-6-Methoxy-N-(1-methyl-2-oxo-1,2-dihydropyridin-3-yl)-2-((1R,2S,4S)-2-methyl-4-(N-methylacetamido)cyclohexyl)-2H-indazole-5-carboxamide—Isomer 1 (Example 6) & Isomer 2 (Example 7)

rac-(7R,8S)—N-Benzyl-7-methyl-1,4-dioxaspiro[4.5]decan-8-amine

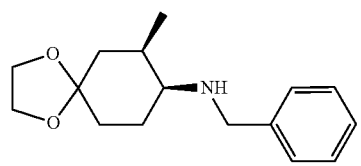 [SMILES: C[C@@H]1CC2(CC[C@@H]1NCc1ccccc1)OCCO2]

And Enantiomer

To a solution of N-benzyl-7-methyl-1,4-dioxaspiro[4.5]decan-8-imine (3.2 kg, 12.3 mol) in MeOH (15 L) cooled to below −60° C. was added NaBH₄ (466.8 g, 12.3 mol) under N₂ atmosphere in 5 batches over 30 min. The resulting mixture was warmed from −60° C. to −30° C. over 1 h, then from −30° C. to 10° C. over 0.5 h. The mixture was quenched with aq. saturated NH₄Cl solution (5 L) and extracted with DCM (5 L×3). The combined organic layers were washed with water (6 L) and brine (6 L), dried over Na₂SO₄, filtered and then concentrated under reduced pressure. The residue was purified by C18-flash chromatography (eluting with 40-70% MeCN in water (0.05% NH₄HCO₃)) to afford the trans-isomer (1.3 kg, 40%) and the desired rac-(7R,8S)-N-benzyl-7-methyl-1,4-dioxaspiro[4.5]decan-8-amine. ¹H NMR (300 MHz, CDCl₃) δ 7.19-7.38 (m, 5H), 3.87-4 (m, 4H), 3.84 (d, 1H), 3.65 (d, 1H), 2.70 (q, 1H), 1.93-2.07 (m, 1H), 1.79-1.93 (m, 2H), 1.71 (dd, 1H), 1.43-1.62 (m, 3H), 0.96 (d, 3H). MS ESI, m/z=262 [M+H]⁺.

rac-(7R,8S)-7-Methyl-1,4-dioxaspiro[4.5]decan-8-amine

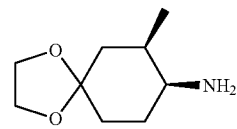

And Enantiomer

A suspension of Palladium on carbon (10 wt. %) (3.0 g, 2.8 mmol) and rac-(7R,8S)-N-benzyl-7-methyl-1,4-dioxaspiro[4.5]decan-8-amine (20.0 g, 76.5 mmol) in MeOH (200 mL) was stirred at rt under an H₂ atmosphere at 2 atm for 15 h. Then the mixture was filtered through celite, and the filtrate was concentrated under reduced pressure to afford rac-(7R,8S)-7-methyl-1,4-dioxaspiro[4.5]decan-8-amine (11.0 g, 84%) as a dark oil, which was used without further purification. ¹H NMR (300 MHz, DMSO-d₆) δ 3.77-3.87 (m, 4H), 2.79 (q, 1H), 1.65-1.78 (m, 2H), 1.48-1.6 (m, 3H), 1.06-1.47 (m, 4H), 0.83 (d, 3H). MS ESI, m/z=172 [M+H]⁺.

rac-5-Bromo-6-methoxy-2-((7R,8S)-7-methyl-1,4-dioxaspiro[4.5]decan-8-yl)-2H-indazole

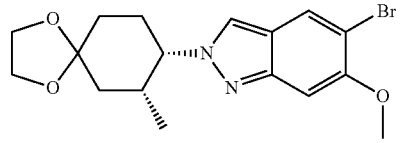 [SMILES: COc1cc2nn([C@H]3CCC4(C[C@H]3C)OCCO4)cc2cc1Br]

And Enantiomer

To a solution of 5-bromo-4-methoxy-2-nitrobenzaldehyde (Int 1) (16.6 g, 65.2 mmol) in i-PrOH (102 mL) was added rac-(7R,8S)-7-methyl-1,4-dioxaspiro[4.5]decan-8-amine (10.2 g, 59.6 mmol) under N₂ atmosphere. The resulting mixture was stirred at 80° C. for 3 h, then cooled to rt, followed by the addition of tri-n-butylphosphine (46.8 g, 231.3 mmol). The reaction mixture was stirred at 80° C. for 11 h, then cooled and stirred at 0° C. for 1 h. The resulting suspension was filtered through filter paper, the collected solid was suspended in i-PrOH (60 mL)/n-heptane (36 mL) and stirred at 60° C. for 1 day. After cooling to rt the desired product was obtained by filtration to give rac-5-bromo-6-methoxy-2-((7R,8S)-7-methyl-1,4-dioxaspiro[4.5]decan-8-yl)-2H-indazole (16.3 g, 72%) as a grey solid. ¹H NMR (300 MHz, DMSO-d₆) δ 8.25 (s, 1H), 7.97 (s, 1H), 7.15 (s, 1H), 4.66 (q, 1H), 3.83-3.98 (m, 7H), 2.24-2.40 (m, 2H), 2.00-2.16 (m, 3H), 1.57-1.70 (m, 2H), 0.55 (d, 3H). MS ESI, m/z=381/383 [M+H]+.

rac-(3R,4S)-4-(5-Bromo-6-methoxy-2H-indazol-2-yl)-3-methylcyclohexan-1-one

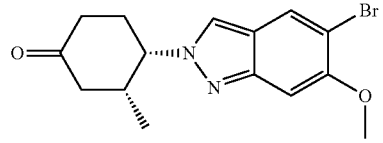 [SMILES: COc1cc2nn([C@H]3CCC(=O)C[C@H]3C)cc2cc1Br]

And Enantiomer

To a solution of rac-5-bromo-6-methoxy-2-((7R,8S)-7-methyl-1,4-dioxaspiro[4.5]decan-8-yl)-2H-indazole (16.3 g, 42.6 mmol in THF/water (300 mL 1:1) was added aq. 12N HCl solution (60 mL, 720.0 mmol). The reaction mixture was stirred at rt for 2 h before the pH of the mixture was adjusted to pH~6 with aq. 2N NaOH solution. THF was removed under reduced pressure to give an aq. suspension. The suspension was filtered, and the collected precipitate was washed with PE (100 mL) and dried under vacuum to afford rac-(3R,4S)-4-(5-bromo-6-methoxy-2H-indazol-2-yl)-3-methylcyclohexan-1-one (13.70 g, 95%) as a pale yellow solid, which was used without further purification. $^1$H NMR (300 MHz, DMSO-$d_6$) δ 8.35 (d, 1H), 8.01 (s, 1H), 7.15 (s, 1H), 5.02 (dt, 1H), 3.87 (s, 3H), 2.61-2.8 (m, 2H), 2.24-2.61 (m, 5H), 0.60 (d, 3H). MS ESI, m/z=337/339 [M+H]+.

rac-(3R,4S)-4-(5-Bromo-6-methoxy-2H-indazol-2-yl)-N,3-dimethylcyclohexan-1-amine

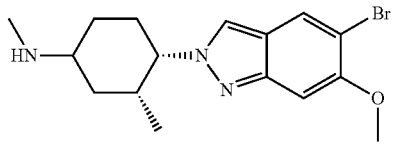

And Enantiomer

To a solution of rac-(3R,4S)-4-(5-bromo-6-methoxy-2H-indazol-2-yl)-3-methylcyclohexan-1-one (780 mg, 2.3 mmol) and methanamine (33 wt. % in MeOH) (2.2 g, 23.1 mmol) in DCE (10 mL) was added sodium triacetoxyborohydride (1.5 g, 6.9 mmol). The resulting mixture was stirred at 25° C. for 1 h, quenched with water (20 mL) and extracted with DCM (50 mL×2). The combined organic layers were dried over Na$_2$SO$_4$, filtered and then concentrated under reduced pressure to afford rac-(3R,4S)-4-(5-bromo-6-methoxy-2H-indazol-2-yl)-N,3-dimethylcyclohexan-1-amine (800 mg, 98%) as a yellow solid, which was used without further purification. MS ESI, m/z=352/354 [M+H]+.

rac-N-((3R,4S)-4-(5-Bromo-6-methoxy-2H-indazol-2-yl)-3-methylcyclohexyl)-N-methylacetamide

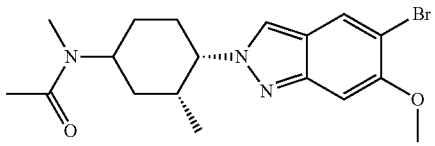 [SMILES: COc1cc2nn([C@H]3CCC(N(C)C(C)=O)C[C@H]3C)cc2cc1Br]

And Enantiomer

To a solution of rac-(3R,4S)-4-(5-bromo-6-methoxy-2H-indazol-2-yl)-N,3-dimethylcyclohexan-1-amine (780 mg, 2.2 mmol) and TEA (1.2 mL, 8.9 mmol) in DCM (10 mL) was added acetic anhydride (452 mg, 4.4 mmol). The resulting mixture was stirred at rt for 1 h. Then, the reaction mixture was concentrated under reduced pressure and purified by C18-flash chromatography (eluting with 0-100% MeCN in water (0.1% FA)) to afford rac-N-((3R,4S)-4-(5-bromo-6-methoxy-2H-indazol-2-yl)-3-methylcyclohexyl)-N-methylacetamide (720 mg, 82%) as a solid. $^1$H NMR (300 MHz, DMSO-$d_6$) (4:5 mixture of stereoisomers) δ 8.29/8.28 (s, 1H) (stereoisomers), 8.00 (s, 1H), 7.11 (s, 1H), 4.61-4.69 (m, 1H), 4.46-4.61/3.85-3.92 (m, 1H) (stereoisomers), 3.89 (s, 3H), 2.97/2.84 (s, 3H) (stereoisomers), 1.93-2.24 (m, 7H), 1.22-1.55 (m, 2H), 0.52-0.6 (m, 3H). MS ESI, m/z=394/396 [M+H]+.

rac-Methyl 6-methoxy-2-((1S,2R)-2-methyl-4-(N-methylacetamido)cyclohexyl)-2H-indazole-5-carboxylate

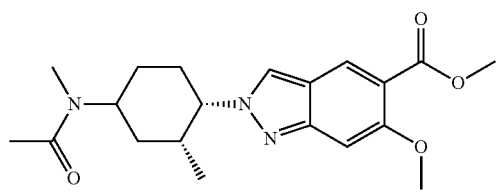 [SMILES: COC(=O)c1cc2cn([C@H]3CCC(N(C)C(C)=O)C[C@H]3C)nc2cc1OC]

And Enantiomer

A mixture of rac-N-((3R,4S)-4-(5-bromo-6-methoxy-2H-indazol-2-yl)-3-methylcyclohexyl)-N-methylacetamide (720 mg, 1.8 mmol), Pd(dppf)Cl$_2$ (267 mg, 0.4 mmol) and DIPEA (1.6 mL, 9.1 mmol) in MeOH (10 mL) was stirred in a sealed vessel under an CO atmosphere at 15 atm, and then heated at 110° C. for 15 h before being concentrated under reduced pressure. The residue was purified by C18-flash chromatography (eluting with 0-100% MeCN in water (0.05% NH$_4$OH)) to afford rac-methyl 6-methoxy-2-((1S,2R)-2-methyl-4-(N-methylacetamido)cyclohexyl)-2H-indazole-5-carboxylate (640 mg, 94%) as a wax-like yellow solid. $^1$H NMR (300 MHz, DMSO-$d_6$) (4:5 mixture of stereoisomers) δ 8.46/8.45 (s, 1H) (stereoisomers), 8.10 (s, 1H), 7.05 (s, 1H), 4.62-4.73 (m, 1H), 4.47-4.62 (m, 1H), 4.47-4.62/3.81-3.92 (m, 1H) (stereoisomers), 3.84 (s, 3H), 3.78 (s, 3H), 2.97/2.84 (s, 3H) (stereoisomers), 1.90-2.37 (m, 7H), 1.22-1.58 (m, 2H), 0.53-0.63 (m, 3H). MS ESI, m/z=374 [M+H]+.

rac-6-Methoxy-2-((1S,2R)-2-methyl-4-(N-methylac-
etamido)cyclohexyl)-2H-indazole-5-carboxylic acid

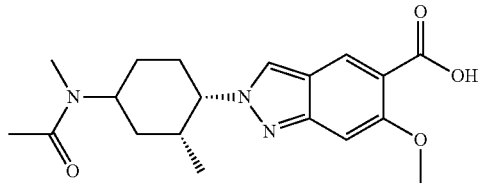 [SMILES: COc1cc2nn([C@H]3CCC(N(C)C(C)=O)C[C@H]3C)cc2cc1C(=O)O]

And Enantiomer

To a solution of rac-methyl 6-methoxy-2-((1S,2R)-2-methyl-4-(N-methylacetamido)cyclohexyl)-2H-indazole-5-carboxylate (620 mg, 1.7 mmol) in MeOH (3 mL) at rt under N₂ atmosphere was added LiOH (119 mg, 5.0 mmol) in water (3 mL). The resulting solution was stirred at rt for 2 h. Then, the pH of the reaction mixture was adjusted to pH 6 with 2N HCl. The mixture was purified directly by C18-flash chromatography (eluting with 5-100% MeCN in water (0.05% FA)) to afford rac-6-methoxy-2-((1S,2R)-2-methyl-4-(N-methylacetamido)cyclohexyl)-2H-indazole-5-carboxylic acid (590 mg, 99%) as a colorless solid. $^1$H NMR (300 MHz, DMSO-$d_6$) (2:3 mixture of stereoisomers) δ 8.43/8.42 (s, 1H) (stereoisomers), 8.07 (s, 1H), 7.03 (s, 1H), 4.62-4.71 (m, 1H), 4.47-4.62/3.79-3.93 (m, 1H) (stereoisomers), 3.84 (s, 3H), 2.97/2.84 (s, 3H) (stereoisomers), 2.43-2.65 (m, 1H), 1.92-2.38 (m, 7H), 1.22-1.60 (m, 2H), 0.51-0.65 (m, 3H). MS ESI, m/z=360 [M+H]$^+$.

6-Methoxy-N-(1-methyl-2-oxo-1,2-dihydropyridin-
3-yl)-2-((1R,2S,4R)-2-methyl-4-(N-methylacet-
amido)cyclohexyl)-2H-indazole-5-carboxamide,
Example 4

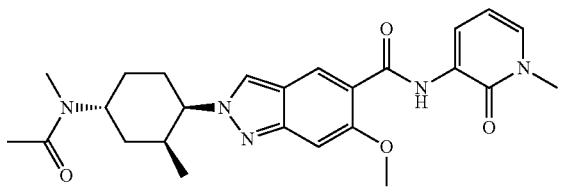 [SMILES: COc1cc2nn([C@@H]3CC[C@@H](N(C)C(C)=O)C[C@@H]3C)cc2cc1C(=O)Nc1cccn(C)c1=O]

6-Methoxy-N-(1-methyl-2-oxo-1,2-dihydropyridin-
3-yl)-2-((1S,2R,4S)-2-methyl-4-(N-methylacet-
amido)cyclohexyl)-2H-indazole-5-carboxamide,
Example 5

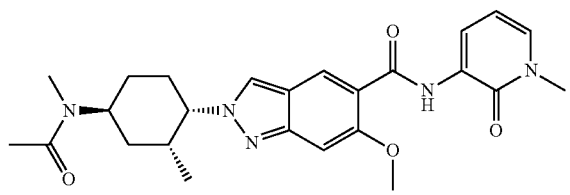 [SMILES: COc1cc2nn([C@H]3CC[C@H](N(C)C(C)=O)C[C@H]3C)cc2cc1C(=O)Nc1cccn(C)c1=O]

rel-6-Methoxy-N-(1-methyl-2-oxo-1,2-dihydropyri-
din-3-yl)-2-((1R,2S,4S)-2-methyl-4-(N-methylacet-
amido)cyclohexyl)-2H-indazole-5-carboxamide—
Isomer 1, Example 6 & Isomer 2, Example 7

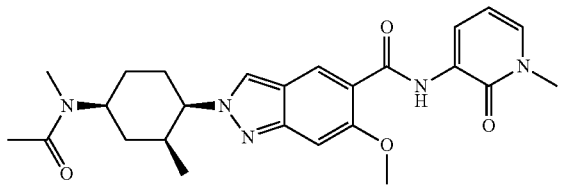

or Enantiomer
ISOMER 1

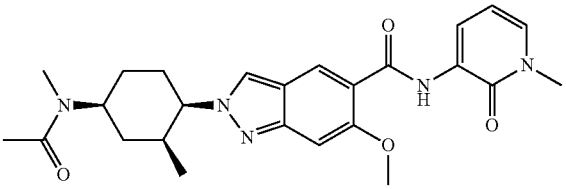

or Enantiomer
ISOMER 2

To a solution of rac-6-methoxy-2-((1S,2R)-2-methyl-4-(N-methylacetamido)cyclohexyl)-2H-indazole-5-carboxylic acid (550 mg, 1.5 mmol), HATU (698 mg, 1.8 mmol) and DIPEA (1.3 mL, 7.7 mmol) in DMF (7 mL) at 25° C. under N₂ atmosphere was added 3-amino-1-methylpyridin-2(1H)-one hydrochloride (614 mg, 3.8 mmol). The reaction mixture was stirred at rt for 2 h and then concentrated under reduced pressure. The residue was purified by C18-flash chromatography (eluting with 0-100% MeCN in water (0.05% NH₄OH)) to give rac-6-methoxy-N-(1-methyl-2-oxo-1,2-dihydropyridin-3-yl)-2-((1R,2S,4R)-2-methyl-4-(N-methylacetamido)cyclohexyl)-2H-indazole-5-carboxamide (130 mg) and rac-6-methoxy-N-(1-methyl-2-oxo-1,2-dihydropyridin-3-yl)-2-((1R,2S,4S)-2-methyl-4-(N-methylacetamido)cyclohexyl)-2H-indazole-5-carboxamide (450 mg).

rac-6-Methoxy-N-(1-methyl-2-oxo-1,2-dihydropyridin-3-yl)-2-((1R,2S,4R)-2-methyl-4-(N-methylacetamido)cyclohexyl)-2H-indazole-5-carboxamide was separated by prep. chiral HPLC (Chiralpak® IA, 5 µm 21.2 mm×150 mm; isocratic with 50% MTBE in EtOH for 30 min; 20.0 mL/min) to afford 6-methoxy-N-(1-methyl-2-oxo-1,2-dihydropyridin-3-yl)-2-((1R,2S,4R)-2-methyl-4-(N-methylacetamido)cyclohexyl)-2H-indazole-5-carboxamide (31 mg, 4%, 100% ee) and 6-Methoxy-N-(1-methyl-2-oxo-1,2-dihydropyridin-3-yl)-2-((1S,2R,4S)-2-methyl-4-(N-methylacetamido)cyclohexyl)-2H-indazole-5-carboxamide (30 mg, 4%, 99.8% ee), both as colorless solids.

rac-6-Methoxy-N-(1-methyl-2-oxo-1,2-dihydropyridin-3-yl)-2-((1R,2S,4S)-2-methyl-4-(N-methylacetamido)cyclohexyl)-2H-indazole-5-carboxamide was separated by prep. chiral HPLC (Chiralpak® IH, 5 µm 20 mm×250 mm; isocratic with 80% MTBE (0.5% 2M NH₃-MeOH solution) in EtOH for 14 min; 20.0 mL/min) to afford rel-6-methoxy-N-(1-methyl-2-oxo-1,2-dihydropyridin-3-yl)-2-((1R,2S,4S)-2-methyl-4-(N-methylacetamido)cyclohexyl)-2H-indazole-5-carboxamide—Isomer 1 (177 mg, 25%, 100% ee) and rel-6-methoxy-N-(1-methyl-2-oxo-1,2-dihydropyridin-3-yl)-2-((1R,2S,4S)-2-methyl-4-(N-methylacetamido)cyclohexyl)-2H-indazole-5-carboxamide—Isomer 2 (169 mg, 24%, 100% ee), both as colorless solids.

(1R,2S,4R)—Isomer, Example 4:1H NMR (400 MHz, DMSO-d$_6$) (2:3 mixture of rotamers) δ 11.04 (s, 1H), 8.59/8.57 (s, 1H) (rotamers), 8.54/8.51 (s, 1H) (rotamers), 8.45 (dd, 1H), 7.43 (dd, 1H), 7.20-7.25 (m, 1H), 6.31 (t, 1H), 4.58-4.73 (m, 1H), 4.58-4.73/3.84-3.98 (m, 1H) (rotamers), 4.07 (s, 3H), 3.56 (s, 3H), 2.84/2.72 (s, 3H) (rotamers), 2.62-2.70 (m, 1H), 2.31-2.45 (m, 1H), 1.93-2.19 (m, 5H), 1.63-1.93 (m, 2H), 1.55-1.63/1.40-1.51 (m, 1H) (rotamers), 0.67/0.63 (d, 3H) (rotamers). MS ESI, m/z=466 [M+H]$^+$.

(1S,2R,4S)—Isomer, Example 5:1H NMR (400 MHz, DMSO-d$_6$) (2:3 mixture of rotamers) δ 11.04 (s, 1H), 8.59/8.57 (s, 1H) (rotamers), 8.54/8.50 (s, 1H) (rotamers), 8.45 (dd, 1H), 7.43 (dd, 1H), 7.20-7.25 (m, 1H), 6.31 (t, 1H), 4.60-4.72 (m, 1H), 4.60-4.72/3.84-3.98 (m, 1H) (rotamers), 4.07 (s, 3H), 3.56 (s, 3H), 2.84/2.72 (s, 3H) (rotamers), 2.62-2.70 (m, 1H), 2.31-2.45 (m, 1H), 1.97-2.16 (m, 5H), 1.63-1.91 (m, 2H), 1.55-1.63/1.42-1.50 (m, 1H) (rotamers), 0.67/0.63 (d, 3H) (rotamers). MS ESI, m/z=466 [M+H]$^+$.

(1R,2S,4S)—Isomer 1, Example 6: $^1$H NMR (400 MHz, DMSO-d$_6$) (5:4 mixture of rotamers) δ 11.03 (s, 1H), 8.60 (s, 1H), 8.58/8.56 (s, 1H) (rotamers), 8.45 (dd, 1H), 7.43 (dd, 1H), 7.22 (s, 1H), 6.31 (t, 1H), 4.66-4.75 (m, 1H), 4.50-4.61/3.82-3.92 (m, 1H) (rotamers), 4.09 (s, 3H), 3.56 (s, 3H), 2.98/2.85 (s, 3H) (rotamers), 2.40-2.69 (m, 1H), 1.95-2.39 (m, 7H), 1.49-1.57/1.33-1.41 (m, 1H) (rotamers), 1.41-1.49/1.26-1.33 (m, 1H) (rotamers), 0.53-0.66 (m, 3H). MS ESI, m/z=466 [M+H]$^+$.

(1R,2S,4S)—Isomer 2, Example 7:1H NMR (400 MHz, DMSO-d$_6$) (5:4 mixture of rotamers) δ 11.03 (s, 1H), 8.60 (s, 1H), 8.58/8.56 (s, 1H) (rotamers), 8.45 (dd, 1H), 7.43 (dd, 1H), 7.22 (s, 1H), 6.31 (t, 1H), 4.66-4.75 (m, 1H), 4.49-4.61/3.81-3.94 (m, 1H) (rotamers), 4.09 (s, 3H), 3.56 (s, 3H), 2.98/2.85 (s, 3H) (rotamers), 2.40-2.67 (m, 1H), 1.96-2.39 (m, 7H), 1.49-1.57/1.33-1.41 (m, 1H) (rotamers), 1.41-1.49/1.26-1.33 (m, 1H) (rotamers), 0.55-0.65 (m, 3H). MS ESI, m/z=466 [M+H]$^+$.

2-((1R,4r)-4-((R)-2-Hydroxy-N-methylpropanamido)cyclohexyl)-6-methoxy-N-(1-methyl-2-oxo-1,2-dihydropyridin-3-yl)-2H-indazole-5-carboxamide (Example 8)

tert-Butyl ((1r,4r)-4-(6-methoxy-5-((1-methyl-2-oxo-1,2-dihydropyridin-3-yl)carbamoyl)-2H-indazol-2-yl)cyclohexyl)(methyl)carbamate

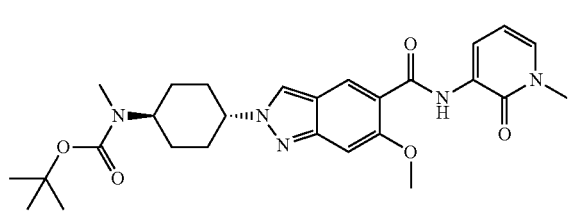 [SMILES: COc1cc2nn([C@H]3CC[C@H](N(C)C(=O)OC(C)(C)C)CC3)cc2cc1C(=O)Nc1cccn(C)c1=O]

To a solution of 2-((1r,4r)-4-((tert-butoxycarbonyl)(methyl)amino)cyclohexyl)-6-methoxy-2H-indazole-5-carboxylic acid (Int 5) (120 mg, 0.3 mmol), 3-amino-1-methylpyridin-2(1H)-one (44 mg, 0.4 mmol) and DIPEA (156 μL, 0.9 mmol) in DMF (5 mL) at 25° C. under N$_2$ atmosphere was added HATU (170 mg, 0.5 mmol). The reaction mixture was stirred at 25° C. for 15 h. The mixture was purified directly by C18-flash chromatography (eluting with 0-100% MeCN in water (0.1% FA)) to afford tert-butyl ((1r,4r)-4-(6-methoxy-5-((1-methyl-2-oxo-1,2-dihydropyridin-3-yl)carbamoyl)-2H-indazol-2-yl)cyclohexyl)(methyl)carbamate (110 mg, 73%) as a pale yellow solid. $^1$H NMR (300 MHz, DMSO-d$_6$) δ 11.04 (s, 1H), 8.54-8.60 (m, 2H), 8.45 (dd, 1H), 7.43 (dd, 1H), 7.22 (s, 1H), 6.31 (t, 1H), 4.39-4.55 (m, 1H), 4.06 (s, 3H), 3.75-4.04 (m, 1H), 3.56 (s, 3H), 2.72 (s, 3H), 2.11-2.24 (m, 2H), 1.90-2.06 (m, 2H), 1.65-1.90 (m, 4H), 1.42 (s, 9H). MS ESI, m/z=510 [M+H]$^+$.

6-Methoxy-N-(1-methyl-2-oxo-1,2-dihydropyridin-3-yl)-2-((1r,4r)-4-(methylamino)cyclohexyl)-2H-indazole-5-carboxamide

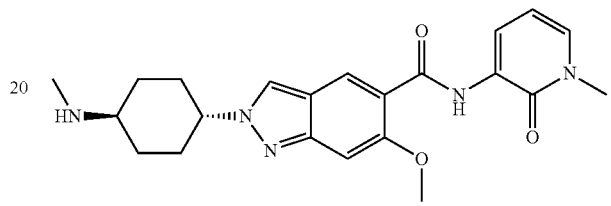

tert-Butyl ((1r,4r)-4-(6-methoxy-5-((1-methyl-2-oxo-1,2-dihydropyridin-3-yl)carbamoyl)-2H-indazol-2-yl)cyclohexyl)(methyl)carbamate (100 mg, 0.2 mmol) was added into 2N HCl in dioxane (8.0 mL, 16.0 mmol) at 25° C. under N$_2$ atmosphere. The resulting mixture was stirred at 25° C. for 2 h before it was concentrated under reduced pressure to afford 6-methoxy-N-(1-methyl-2-oxo-1,2-dihydropyridin-3-yl)-2-((1r,4r)-4-(methylamino)cyclohexyl)-2H-indazole-5-carboxamide (95 mg, 100%) as the HCl salt, which was used without further purification. $^1$H NMR (400 MHz, DMSO-d$_6$) (HCl salt) δ 11.03 (s, 1H), 8.97-9.11 (m, 2H), 8.57 (s, 2H), 8.44 (dd, 1H), 7.43 (dd, 1H), 7.21 (s, 1H), 6.31 (t, 1H), 4.46-4.58 (m, 1H), 4.06 (s, 3H), 3.56 (s, 3H), 3.00-3.16 (m, 1H), 2.56 (t, 3H), 2.16-2.29 (m, 4H), 1.89-2.05 (m, 2H), 1.54-1.69 (m, 2H). MS ESI, m/z=410 [M+H]$^+$.

(R)-1-(((1r,4R)-4-(6-Methoxy-5-((1-methyl-2-oxo-1,2-dihydropyridin-3-yl)carbamoyl)-2H-indazol-2-yl)cyclohexyl)(methyl)amino)-1-oxopropan-2-yl acetate

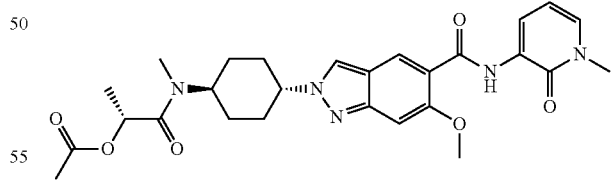

To a solution of the HCl salt of 6-methoxy-N-(1-methyl-2-oxo-1,2-dihydropyridin-3-yl)-2-((1r,4r)-4-(methylamino)cyclohexyl)-2H-indazole-5-carboxamide (90 mg, 0.2 mmol) and TEA (113 μL, 0.8 mmol) in DCM (8 mL) at 25° C. under N$_2$ atmosphere was added (R)-1-chloro-1-oxopropan-2-yl acetate (46 mg, 0.3 mmol). The resulting solution was stirred at 25° C. for 2 h, then poured into saturated NH$_4$Cl solution (10 mL) and extracted with DCM (25 mL×2). The organic layer was dried over Na$_2$SO$_4$, filtered and concentrated under reduced pressure to afford (R)-1-(((1r,4R)-4-(6- methoxy-5-((1-methyl-2-oxo-1,2-dihydropyridin-3-yl)carbamoyl)-2H-indazol-2-yl)cyclohexyl)(methyl)amino)-1-oxopropan-2-yl acetate (100 mg, 95%) as a yellow solid, which was used without further purification. $^1$H NMR (400 MHz, DMSO-$d_6$) (5:4 mixture of rotamers) δ 11.04 (s, 1H), 8.53-8.61 (m, 2H), 8.45 (dd, 1H), 7.43 (dd, 1H), 7.22/7.20 (s, 1H) (rotamers), 6.31 (t, 1H), 5.46/5.28 (q, 1H) (rotamers), 4.40-4.58 (m, 1H), 4.29-4.40 (m, 1H), 4.06 (s, 3H), 3.56 (s, 3H), 2.91/2.75 (s, 3H) (rotamers), 1.58-2.28 (m, 11H), 1.33/1.31 (d, 3H) (rotamers). MS ESI, m/z=524 [M+H]$^+$.

2-((1R,4r)-4-((R)-2-Hydroxy-N-methylpropanamido)cyclohexyl)-6-methoxy-N-(1-methyl-2-oxo-1,2-dihydropyridin-3-yl)-2H-indazole-5-carboxamide, Example 8

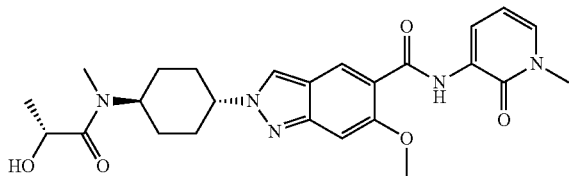 [SMILES: COc1cc2nn([C@H]3CC[C@H](N(C)C(=O)[C@@H](C)O)CC3)cc2cc1C(=O)Nc1cccn(C)c1=O]

To a solution of (R)-1-(((1r,4R)-4-(6-methoxy-5-((1-methyl-2-oxo-1,2-dihydropyridin-3-yl)carbamoyl)-2H-indazol-2-yl)cyclohexyl)(methyl)amino)-1-oxopropan-2-yl acetate (90 mg, 0.2 mmol) in THF/water (8 mL, 1:1) at 25° C. under N$_2$ atmosphere was added LiOH (21 mg, 0.9 mmol). The resulting solution was stirred at 25° C. for 2 h, then poured into saturated NH$_4$Cl solution (10 mL) and extracted with DCM (25 mL×3). The organic layer was dried over Na$_2$SO$_4$, filtered and concentrated under reduced pressure. The residue was purified by prep. HPLC (Xbridge® BEH OBD C18 5 μm 30×150 mm; elution gradient 18-38% MeCN in water (10 mM NH$_4$HCO$_3$+0.1% NH$_4$OH) over 8 min; 60 mL/min) to afford 2-((1R,4r)-4-((R)-2-hydroxy-N-methylpropanamido)cyclohexyl)-6-methoxy-N-(1-methyl-2-oxo-1,2-dihydropyridin-3-yl)-2H-indazole-5-carboxamide (52 mg, 63%), Example 8, as a pale yellow solid. $^1$H NMR (400 MHz, DMSO-$d_6$) (5:4 mixture of rotamers) δ 11.05 (s, 1H), 8.54-8.61 (m, 2H), 8.45 (dd, 1H), 7.43 (dd, 1H), 7.22/7.20 (s, 1H) (rotamers), 6.31 (t, 1H), 4.86-5.02/4.66-4.86 (m, 1H) (rotamers), 4.33-4.58/3.93-4.03 (m, 3H) (rotamers), 4.07 (s, 3H), 3.56 (s, 3H), 2.90/2.76 (s, 3H) (rotamers), 2.14-2.26 (m, 2H), 1.58-2.14 (m, 6H), 1.21/1.18 (d, 3H) (rotamers). MS ESI, m/z=482 [M+H]$^+$.

N-(1-(fluoromethyl)-2-oxo-1,2-dihydropyridin-3-yl)-2-((1R,4r)-4-((R)-2-hydroxy-N-methylpropanamido)cyclohexyl)-6-methoxy-2H-indazole-5-carboxamide (Example 9)

1-(Fluoromethyl)-3-nitropyridin-2(1H)-one

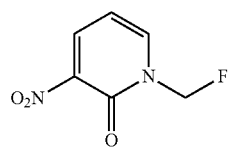 [SMILES: O=c1c([N+](=O)[O-])cccn1CF]

To a suspension of 3-nitropyridin-2(1H)-one (300 mg, 2.1 mmol) and K$_2$CO$_3$ (888 mg, 6.4 mmol) in DMF (8 mL) at 25° C. under N$_2$ atmosphere was added fluoroiodomethane (856 mg, 5.4 mmol). The resulting mixture was heated at 80° C. for 2 h, then quenched with water (20 mL) and extracted with DCM/i-PrOH (3/1) (25 mL×3). The organic layer was dried over Na$_2$SO$_4$, filtered and concentrated under reduced pressure. The residue was purified by prep. HPLC (Waters SunFire® C18 OBD, 5 μm 30×150 mm; elution gradient 4-20% MeCN in water (0.1% TFA) over 7 min; 60 mL/min) to afford 1-(fluoromethyl)-3-nitropyridin-2(1H)-one (130 mg, 35%) as a yellow solid. $^1$H NMR (400 MHz, DMSO-$d_6$) δ 8.51 (dd, 1H), 8.32 (dd, 1H), 6.53 (dd, 1H), 6.05 (d, 2H). MS ESI, m/z=173 [M+H]$^+$.

3-Amino-1-(fluoromethyl)pyridin-2(1H)-one

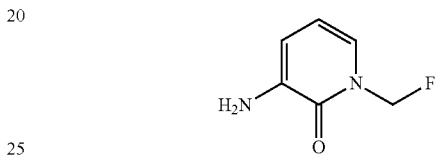

To a suspension of 1-(fluoromethyl)-3-nitropyridin-2(1H)-one (120 mg, 0.7 mmol) and zinc (228 mg, 3.5 mmol) in THF/MeOH (1:2, 6 mL) at 25° C. under N$_2$ atmosphere was added a solution of NH$_4$Cl (186 mg, 3.5 mmol) in water (2 mL). The resulting suspension was heated at 60° C. for 2 h. The reaction mixture was filtered through silica gel and the silica gel cake was washed with MeOH (20 mL). The combined filtrates were concentrated under reduced pressure. The residue was basified with an aq. 30% NH$_4$OH solution, diluted with water (10 mL) and extracted with EtOAc (25 mL×3). The combined organic layers were dried over Na$_2$SO$_4$, filtered and concentrated under reduced pressure. The residue was purified by prep. TLC (eluting with 50% EtOAc in PE) to afford 3-amino-1-(fluoromethyl)pyridin-2(1H)-one (70 mg, 71%) as a yellow oil. $^1$H NMR (400 MHz, DMSO-$d_6$) δ 7.02 (dd, 1H), 6.45 (dd, 1H), 6.10 (t, 1H), 5.95 (d, 2H), 5.26 (s, 2H). MS ESI, m/z=143 [M+H]$^+$.

N-(1-(Fluoromethyl)-2-oxo-1,2-dihydropyridin-3-yl)-2-((1R,4r)-4-((R)-2-hydroxy-N-methylpropanamido)cyclohexyl)-6-methoxy-2H-indazole-5-carboxamide, Example 9

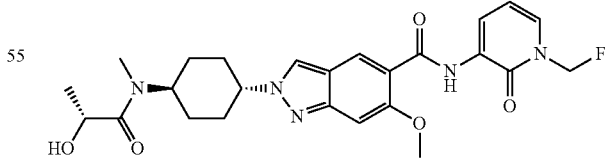

A solution of 2-((1R,4r)-4-((R)-2-hydroxy-N-methylpropanamido)cyclohexyl)-6-methoxy-2H-indazole-5-carboxylic acid (Int 6) (40 mg, 0.1 mmol), HATU (49 mg, 0.1 mmol) and DIPEA (74 μL, 0.4 mmol) in DMF (3 mL) was stirred at 25° C. under N$_2$ atmosphere for 1 h, followed by the addition of 3-amino-1-(fluoromethyl)pyridin-2(1H)-one (53 mg, 0.4 mmol). The resulting solution was stirred at 60°

C. for 12 h. The reaction mixture was purified directly by prep. HPLC twice (YMC-Actus Triart C18 ExRS 5 μm 30×150 mm; elution gradient 24-36% MeCN in water (10 mM NH₄HCO₃+0.1% NH₄OH) over 10 min; 60 mL/min) to afford N-(1-(fluoromethyl)-2-oxo-1,2-dihydropyridin-3-yl)-2-((1R,4r)-4-((R)-2-hydroxy-N-methylpropanamido)cyclohexyl)-6-methoxy-2H-indazole-5-carboxamide (23 mg, 43%), Example 9, as a colorless solid. ¹H NMR (400 MHz, DMSO-d₆) (5:6 mixture of rotamers) δ 11.05 (s, 1H), 8.56-8.63 (m, 2H), 8.51 (dd, 1H), 7.57 (dd, 1H), 7.24/7.21 (s, 1H) (rotamers), 6.41 (t, 1H), 6.07 (d, 2H), 4.93/4.75 (d, 1H) (rotamers), 4.33-4.59/3.93-4.04 (m, 3H) (rotamers), 4.08 (s, 3H), 2.91 (s, 2H), 2.76 (s, 1H), 2.91/2.76 (s, 3H) (rotamers), 2.15-2.27 (m, 2H), 1.6-2.15 (m, 6H), 1.22/1.18 (d, 3H) (rotamers). MS ESI, m/z=500 [M+H]⁺.

N-(1-(Cyanomethyl)-2-oxo-1,2-dihydropyridin-3-yl)-2-((1R,4r)-4-((R)-2-hydroxy-N-methylpropanamido)cyclohexyl)-6-methoxy-2H-indazole-5-carboxamide (Example 10)

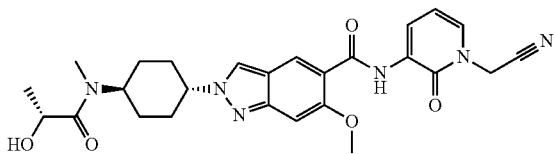 [SMILES: COc1cc2nn([C@H]3CC[C@H](N(C)C(=O)[C@@H](C)O)CC3)cc2cc1C(=O)Nc1cccn(CC#N)c1=O]

A solution of 2-((1R,4r)-4-((R)-2-hydroxy-N-methylpropanamido)cyclohexyl)-6-methoxy-2H-indazole-5-carboxylic acid (Int 6) (40 mg, 0.1 mmol), HATU (49 mg, 0.1 mmol) and DIPEA (74 μL, 0.4 mmol) in DMF (3 mL) at 25° C. under N₂ atmosphere was stirred for 1 h, followed by the addition of 2-(3-amino-2-oxopyridin-1(2H)-yl)acetonitrile (40 mg, 0.3 mmol). The reaction mixture was stirred at 60° C. for 2 h. The mixture was purified directly by prep. HPLC (Xbridge® BEH OBD C18 5 μm 30×150 mm; elution gradient 21-36% MeCN in water (10 mM NH₄HCO₃+0.1% NH₄OH) over 8 min; 60 mL/min) to afford N-(1-(cyanomethyl)-2-oxo-1,2-dihydropyridin-3-yl)-2-((1R,4r)-4-((R)-2-hydroxy-N-methylpropanamido)cyclohexyl)-6-methoxy-2H-indazole-5-carboxamide (29 mg, 55%), Example 10, as a colorless solid. ¹H NMR (400 MHz, DMSO-d₆) (5:6 mixture of rotamers) δ 11.03 (s, 1H), 8.55-8.64 (m, 2H), 8.51 (dd, 1H), 7.51 (dd, 1H), 7.24/7.22 (s, 1H) (rotamers), 6.45 (t, 1H), 5.16 (s, 2H), 4.93/4.75 (d, 1H) (rotamers), 4.34-4.57/3.93-4.03 (m, 3H) (rotamers), 4.09 (s, 3H), 2.91/2.76 (s, 3H) (rotamers), 2.15-2.26 (m, 2H), 1.62-2.15 (m, 6H), 1.22/1.18 (d, 3H) (rotamers). MS ESI, m/z=507 [M+H]⁺.

N-(1-Cyclopropyl-2-oxo-1,2-dihydropyridin-3-yl)-2-((1S,4r)-4-((S)-2-hydroxy-N-methylpropanamido)cyclohexyl)-6-methoxy-2H-indazole-5-carboxamide (Example 11)

tert-Butyl ((1r,4r)-4-(5-((1-cyclopropyl-2-oxo-1,2-dihydropyridin-3-yl)carbamoyl)-6-methoxy-2H-indazol-2-yl)cyclohexyl)(methyl)carbamate To a solution of 2-((1r,4r)-4-((tert-butoxycarbonyl)(methyl)amino)cyclohexyl)-6-methoxy-2H-indazole-5-carboxylic acid (Int 5) (300 mg, 0.7 mmol), HATU (339 mg, 0.9 mmol) and DIPEA (519 μL, 3.0 mmol) in DMF (5 mL) at 25° C. under N₂ atmosphere was added 3-amino-1-cyclopropylpyridin-2(1H)-one hydrochloride (167 mg, 0.9 mmol). The reaction mixture was stirred at 25° C. for 15 h. The mixture was purified directly by C18-flash chromatography (eluting with 0-100% MeCN in water (0.05% NH₄OH)) to afford to afford tert-butyl ((1r,4r)-4-(5-((1-cyclopropyl-2-oxo-1,2-dihydropyridin-3-yl)carbamoyl)-6-methoxy-2H-indazol-2-yl)cyclohexyl)(methyl)carbamate (300 mg, 75%) as a colorless solid. ¹H NMR (300 MHz, DMSO-d₆) δ 11.05 (s, 1H), 8.53-8.59 (m, 2H), 8.42 (dd, 1H), 7.29 (dd, 1H), 7.22 (s, 1H), 6.27 (t, 1H), 4.37-4.54 (m, 1H), 4.07 (s, 3H), 3.76-4.03 (m, 1H), 3.39-3.49 (m, 1H), 2.71 (s, 3H), 2.09-2.26 (m, 2H), 1.87-2.08 (m, 2H), 1.59-1.86 (m, 4H), 1.41 (s, 9H), 0.97-1.09 (m, 2H), 0.81-0.93 (m, 2H). MS ESI, m/z=536 [M+H]⁺.

N-(1-Cyclopropyl-2-oxo-1,2-dihydropyridin-3-yl)-6-methoxy-2-((1r,4r)-4-(methylamino)cyclohexyl)-2H-indazole-5-carboxamide

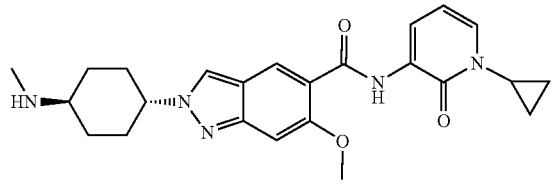

To a solution of tert-butyl ((1r,4r)-4-(5-((1-cyclopropyl-2-oxo-1,2-dihydropyridin-3-yl)carbamoyl)-6-methoxy-2H-indazol-2-yl)cyclohexyl)(methyl)carbamate (295 mg, 0.6 mmol) in DCM (1 mL) was added 4N HCl in dioxane (688 μL, 2.8 mmol) at 25° C. under N₂ atmosphere. The resulting mixture was stirred at 25° C. for 17 h and then concentrated under reduced pressure to afford the HCl salt of N-(1-cyclopropyl-2-oxo-1,2-dihydropyridin-3-yl)-6-methoxy-2-((1r,4r)-4-(methylamino)cyclohexyl)-2H-indazole-5-carboxamide (260 mg, 100%) as a colorless solid, which was used without further purification. ¹H NMR (300 MHz, DMSO-d₆) δ 11.04 (s, 1H), 8.57 (s, 2H), 8.42 (dd, 1H), 7.29 (dd, 1H), 7.21 (s, 1H), 6.27 (t, 1H), 4.43-4.58 (m, 1H), 4.07 (s, 3H), 3.39-3.48 (m, 1H), 2.97-3.13 (m, 1H), 2.54 (t, 3H), 2.13-2.31 (m, 4H), 1.86-2.06 (m, 2H), 1.52-1.71 (m, 2H), 0.97-1.10 (m, 2H), 0.85-0.93 (m, 2H). MS ESI, m/z=436 [M+H]⁺.

(S)-1-(((1r,4S)-4-(5-((1-Cyclopropyl-2-oxo-1,2-dihydropyridin-3-yl)carbamoyl)-6-methoxy-2H-indazol-2-yl)cyclohexyl)(methyl)amino)-1-oxopropan-2-yl acetate

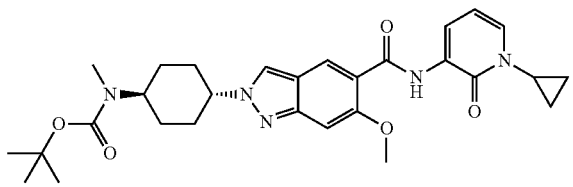 [SMILES: COc1cc2nn([C@H]3CC[C@H](N(C)C(=O)OC(C)(C)C)CC3)cc2cc1C(=O)Nc1cccn(C2CC2)c1=O]

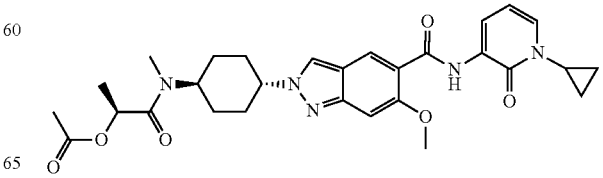

To a solution of the HCl salt of N-(1-cyclopropyl-2-oxo-1,2-dihydropyridin-3-yl)-6-methoxy-2-((1r,4r)-4-(methylamino)cyclohexyl)-2H-indazole-5-carboxamide (255 mg, 0.5 mmol) and TEA (226 μL, 1.6 mmol) in DCM (20 mL) was added (S)-1-chloro-1-oxopropan-2-yl acetate (114 mg, 0.8 mmol) at 0° C. under N₂ atmosphere. The resulting mixture was stirred at 25° C. for 30 min, then quenched with water (25 mL) and extracted with DCM (15 mL). The organic layer was dried over Na₂SO₄, filtered and concentrated under reduced pressure. The residue was purified by C18-flash chromatography (eluting with 0-100% MeCN in water (0.05% NH₄OH)) to afford (S)-1-(((1r,4S)-4-(5-((1-cyclopropyl-2-oxo-1,2-dihydropyridin-3-yl)carbamoyl)-6-methoxy-2H-indazol-2-yl)cyclohexyl)(methyl)amino)-1-oxopropan-2-yl acetate (295 mg, 99%) as a colorless solid. ¹H NMR (300 MHz, DMSO-d₆) (2:3 mixture of rotamers) δ 11.05 (s, 1H), 8.50-8.59 (m, 2H), 8.42 (dd, 1H), 7.29 (dd, 1H), 7.22/7.20 (s, 1H) (rotamers), 6.27 (t, 1H), 5.45/5.27 (q, 1H) (rotamers), 4.40-4.56 (m, 1H), 4.26-4.39/3.71-3.86 (m, 1H) (rotamers), 4.07 (s, 3H), 3.39-3.49 (m, 1H), 2.90/2.74 (s, 3H) (rotamers), 1.69-2.28 (m, 10H), 1.54-1.68 (m, 1H), 1.31 (t, 3H), 0.98-1.11 (m, 2H), 0.84-0.94 (m, 2H). MS ESI, m/z=550 [M+H]⁺.

N-(1-Cyclopropyl-2-oxo-1,2-dihydropyridin-3-yl)-2-((1S,4r)-4-((S)-2-hydroxy-N-methylpropanamido)cyclohexyl)-6-methoxy-2H-indazole-5-carboxamide, Example 11

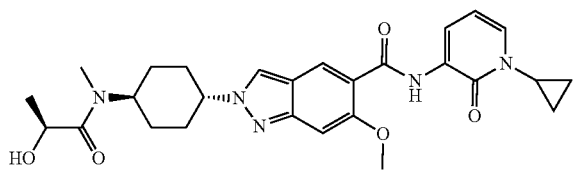 [SMILES: COc1cc2nn([C@H]3CC[C@H](N(C)C(=O)[C@H](C)O)CC3)cc2cc1C(=O)Nc1cccn(C2CC2)c1=O]

To a solution of (S)-1-(((1r,4S)-4-(5-((1-cyclopropyl-2-oxo-1,2-dihydropyridin-3-yl)carbamoyl)-6-methoxy-2H-indazol-2-yl)cyclohexyl)(methyl)amino)-1-oxopropan-2-yl acetate (290 mg, 0.5 mmol) in MeOH (10 mL) at 25° C. under N₂ atmosphere was added LiOH (38 mg, 1.6 mmol) in water (10 mL). The resulting solution was stirred at 25° C. for 15 h. The reaction mixture was purified directly by C18-flash chromatography (eluting with 20-50% MeCN in water (0.05% NH₄OH)) to afford N-(1-cyclopropyl-2-oxo-1,2-dihydropyridin-3-yl)-2-((1S,4r)-4-((S)-2-hydroxy-N-methylpropanamido)cyclohexyl)-6-methoxy-2H-indazole-5-carboxamide (250 mg, 93%, 99.8% ee), Example 11, as a colorless solid. ¹H NMR (400 MHz, DMSO-d₆) (2:3 mixture of rotamers) δ 11.05 (s, 1H), 8.53-8.61 (m, 2H), 8.42 (dd, 1H), 7.29 (dd, 1H), 7.22/7.19 (s, 1H) (rotamers), 6.27 (t, 1H), 4.91/4.75 (br.s, 1H), 4.32-4.56/3.91-4.03 (m, 3H) (rotamers), 4.07 (s, 3H), 3.40-3.48 (m, 1H), 2.90/2.75 (s, 3H) (rotamers), 1.71-2.27 (m, 7H), 1.60-1.70 (m, 1H), 1.21/1.17 (d, 3H) (rotamers), 0.99-1.08 (m, 2H), 0.86-0.92 (m, 2H). MS ESI, m/z=508 [M+H]⁺.

N-(1-Cyclopropyl-2-oxo-1,2-dihydropyridin-3-yl)-2-((1R,4r)-4-((R)-2-hydroxy-N-methylpropanamido)cyclohexyl)-6-methoxy-2H-indazole-5-carboxamide (Example 12)

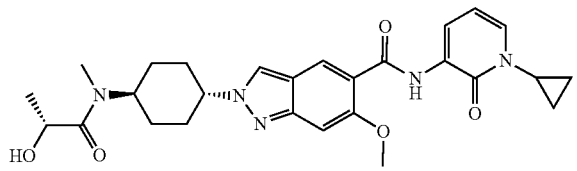 [SMILES: COc1cc2nn([C@H]3CC[C@H](N(C)C(=O)[C@@H](C)O)CC3)cc2cc1C(=O)Nc1cccn(C2CC2)c1=O]

To a solution of 2-((1R,4r)-4-((R)-2-hydroxy-N-methylpropanamido)cyclohexyl)-6-methoxy-2H-indazole-5-carboxylic acid (Int 6) (200 mg, 0.5 mmol), 3-amino-1-cyclopropylpyridin-2(1H)-one (120 mg, 0.8 mmol) and DIPEA (372 μL, 2.1 mmol) in DMF (2 mL) under N₂ atmosphere was added HATU (243 mg, 0.6 mmol). The reaction mixture was stirred at 20° C. for 17 h. The reaction mixture was purified directly by C18-flash chromatography (eluting with 0-100% MeCN in water (0.05% FA)) and further by prep. HPLC (YMC-Actus Triart C18 5 μm 30×150 mm; elution gradient 15-40% MeCN in water (10 mM (NH₄)₂CO₃+0.1% NH₄OH) over 10 min; 60 mL/min) to afford N-(1-cyclopropyl-2-oxo-1,2-dihydropyridin-3-yl)-2-((1R,4r)-4-((R)-2-hydroxy-N-methylpropanamido)cyclohexyl)-6-methoxy-2H-indazole-5-carboxamide (32 mg, 12%), Example 12, as a colorless solid. ¹H NMR (400 MHz, DMSO-d) (4:5 mixture of rotamers) δ 11.05 (s, 1H), 8.54-8.61 (m, 2H), 8.43 (dd, 1H), 7.29 (dd, 1H), 7.23/7.20 (s, 1H) (rotamers), 6.28 (t, 1H), 4.91/4.73 (d, 1H) (rotamers), 4.37-4.56 (m, 2H), 4.34-4.45/3.93-4.04 (m, 1H) (rotamers), 4.08 (s, 3H), 3.45 (tt, 1H), 2.91/2.77 (s, 3H) (rotamers), 2.15-2.28 (m, 2H), 1.96-2.15 (m, 2H), 1.72-1.96 (m, 3H), 1.68 (s, 1H), 1.16-1.26 (m, 3H), 1-1.09 (m, 2H), 0.87-0.95 (m, 2H). MS ESI, m/z=508 [M+H]⁺.

2-((1R,4r)-4-((R)-2-Hydroxy-N-methylpropanamido)cyclohexyl)-6-methoxy-N-(1-(oxetan-3-yl)-2-oxo-1,2-dihydropyridin-3-yl)-2H-indazole-5-carboxamide (Example 13)

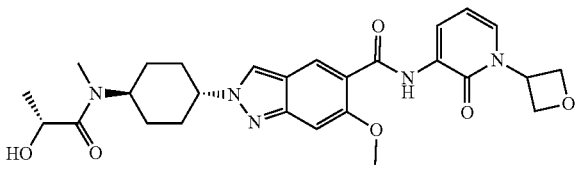 [SMILES: COc1cc2nn([C@H]3CC[C@H](N(C)C(=O)[C@@H](C)O)CC3)cc2cc1C(=O)Nc1cccn(C2COC2)c1=O]

To a solution of 2-((1R,4r)-4-((R)-2-hydroxy-N-methylpropanamido)cyclohexyl)-6-methoxy-2H-indazole-5-carboxylic acid (Int 6) (50 mg, 0.1 mmol), HATU (61 mg, 0.2 mmol) and DIPEA (93 μL, 0.5 mmol) in DMF (2 mL) at 25° C. under N₂ atmosphere was added 3-amino-1-(oxetan-3-yl)pyridin-2(1H)-one (27 mg, 0.2 mmol). The reaction mixture was stirred at 25° C. for 16 h. The mixture was purified directly by prep. HPLC twice (Waters XSelect CSH Fluoro-Phenyl OBD, 5 μm 30×150 mm; elution gradient 26-36% MeCN in water (0.1% FA) over 8 min, 60 mL/min; followed by Xbridge® BEH OBD C18 5 μm 30×150 mm; elution gradient 17-37% MeCN in water (10 mM NH₄HCO₃+0.1%

NH₄OH) over 8 min; 60 mL/min) to afford 2-((1R,4r)-4-((R)-2-hydroxy-N-methylpropanamido)cyclohexyl)-6-methoxy-N-(1-(oxetan-3-yl)-2-oxo-1,2-dihydropyridin-3-yl)-2H-indazole-5-carboxamide (33 mg, 47%), Example 13, as a colorless solid. ¹H NMR (400 MHz, DMSO-d₆) (5:6 mixture of rotamers) δ 10.98 (s, 1H), 8.53-8.63 (m, 2H), 8.49 (dd, 1H), 7.57 (dd, 1H), 7.22/7.19 (s, 1H) (rotamers), 6.45 (t, 1H), 5.66 (p, 1H), 4.92 (t, 2H), 4.80 (t, 2H), 4.33-4.57/3.93-4.02 (m, 3H) (rotamers), 4.05 (s, 3H), 2.91/2.76 (s, 3H) (rotamers), 2.14-2.28 (m, 2H), 1.61-2.14 (m, 6H), 1.21/1.18 (d, 3H) (rotamers). MS ESI, m/z=524 [M+H]⁺.

2-((1R,4r)-4-((R)-2-Hydroxy-N-methylpropanamido)cyclohexyl)-6-methoxy-N-(2-oxo-1-(1H-pyrazol-4-yl)-1,2-dihydropyridin-3-yl)-2H-indazole-5-carboxamide (Example 14)

3-Amino-1-(1-((2-(trimethylsilyl)ethoxy)methyl)-1H-pyrazol-4-yl)pyridin-2(1H)-one

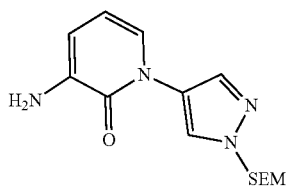

To a suspension of 3-aminopyridin-2(1H)-one (100 mg, 0.9 mmol), N,N'-dimethylethylenediamine (160 mg, 1.8 mmol), Cs₂CO₃ (592 mg, 1.8 mmol) and copper(I) iodide (35 mg, 0.2 mmol) in 1,4-dioxane (10 mL) at 25° C. under N₂ atmosphere was added 4-bromo-1-((2-(trimethylsilyl)ethoxy)methyl)-1H-pyrazole (252 mg, 0.9 mmol). The resulting mixture was heated at 105° C. for 15 h. The reaction was carried out 11 times in parallel on the same scale. The combined reaction mixtures were filtered through celite. The filtrate was concentrated under reduced pressure. The residue was purified by C18 flash chromatography (eluting with 0-100% MeCN in water (0.05% NH₄OH)) to afford crude 3-amino-1-(1-((2-(trimethylsilyl)ethoxy)methyl)-1H-pyrazol-4-yl)pyridin-2(1H)-one (2.1 g, 69%) as a dark oil. MS ESI, m/z=307 [M+H]⁺.

2-((1R,4r)-4-((R)-2-Hydroxy-N-methylpropanamido)cyclohexyl)-6-methoxy-N-(2-oxo-1-(1-((2-(trimethylsilyl)ethoxy)methyl)-1H-pyrazol-4-yl)-1,2-dihydropyridin-3-yl)-2H-indazole-5-carboxamide

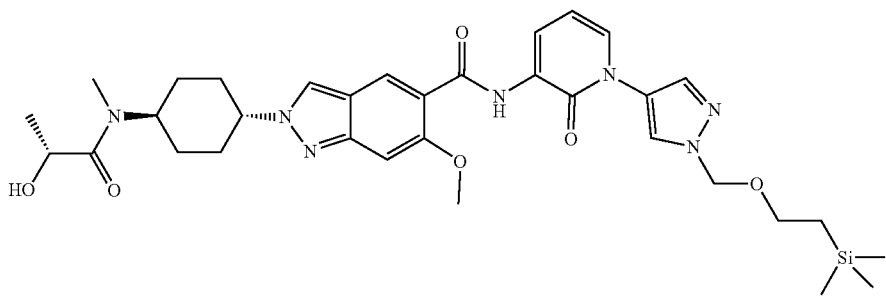 [SMILES: COc1cc2nn([C@H]3CC[C@H](N(C)C(=O)[C@@H](C)O)CC3)cc2cc1C(=O)Nc1cccn(-c2cnn(COCC[Si](C)(C)C)c2)c1=O]

To a solution of 2-((1R,4r)-4-((R)-2-hydroxy-N-methylpropanamido)cyclohexyl)-6-methoxy-2H-indazole-5-carboxylic acid (Int 6) (199 mg, 0.5 mmol), HATU (242 mg, 0.6 mmol) and DIPEA (370 μL, 2.1 mmol) in DMF (10 mL) at 25° C. under N₂ atmosphere was added 3-amino-1-(1-((2-(trimethylsilyl)ethoxy)methyl)-1H-pyrazol-4-yl)pyridin-2(1H)-one (195 mg, 0.6 mmol). The reaction mixture was stirred at 25° C. for 16 h. The mixture was purified by C18-flash chromatography (eluting with 5-100% MeCN in water (0.05% NH₄OH)) to afford 2-((1R,4r)-4-((R)-2-hydroxy-N-methylpropanamido)cyclohexyl)-6-methoxy-N-(2-oxo-1-(1-((2-(trimethylsilyl)ethoxy)methyl)-1H-pyrazol-4-yl)-1,2-dihydropyridin-3-yl)-2H-indazole-5-carboxamide (193 mg, 55%) as a grey solid. ¹H NMR (300 MHz, DMSO-d₆) (5:6 mixture of rotamers) δ 11.10 (s, 1H), 8.56-8.64 (m, 2H), 8.55 (s, 1H), 8.51 (dd, 1H), 8.02 (s, 1H), 7.62 (dd, 1H), 7.23/7.20 (s, 1H) (rotamers), 6.47 (t, 1H), 5.48 (s, 2H), 4.92/4.74 (m, 1H) (rotamers), 4.31-4.59/3.92-4.03 (m, 3H) (rotamers), 4.07 (s, 3H), 3.61 (t, 2H), 2.91/2.77 (s, 3H) (rotamers), 1.59-2.30 (m, 8H), 1.14-1.27 (m, 3H), 0.87 (t, 2H), −0.02 (s, 9H). MS ESI, m/z=664 [M+H]⁺.

2-((1R,4r)-4-((R)-2-Hydroxy-N-methylpropanamido)cyclohexyl)-6-methoxy-N-(2-oxo-1-(1H-pyrazol-4-yl)-1,2-dihydropyridin-3-yl)-2H-indazole-5-carboxamide, Example 14

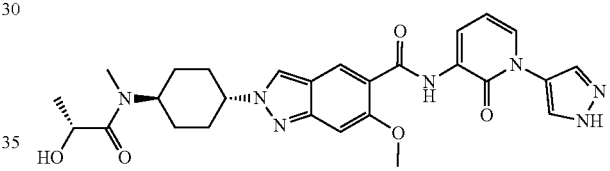

To a solution of 2-((1R,4r)-4-((R)-2-hydroxy-N-methylpropanamido)cyclohexyl)-6-methoxy-N-(2-oxo-1-(1-((2-(trimethylsilyl)ethoxy)methyl)-1H-pyrazol-4-yl)-1,2-dihydropyridin-3-yl)-2H-indazole-5-carboxamide (190 mg, 0.3 mmol) in DCM (20 mL) was added 4N HCl in dioxane (358 μL, 1.43 mmol) at 25° C. under N₂ atmosphere. The resulting mixture was stirred at 25° C. for 16 h and then concentrated under reduced pressure. The residue was purified by prep. HPLC twice (Xbridge® BEH OBD C18 5 μm 30×150 mm; elution gradient 18-38% MeCN in water (10 mM NH₄HCO₃+0.1% NH₄OH) over 8 min, 60 mL/min; followed by Waters XSelect CSH Fluoro-Phenyl OBD, 5 μm 30×150 mm; elution gradient 30-40% MeCN in water (0.1% FA) over 8 min, 60 mL/min) to afford 2-((1R,4r)-4-((R)-2-hydroxy-N-methylpropanamido)cyclohexyl)-6-methoxy-N-

(2-oxo-1-(1H-pyrazol-4-yl)-1,2-dihydropyridin-3-yl)-2H-indazole-5-carboxamide (26 mg, 17%), Example 14, as a colorless solid. ¹H NMR (400 MHz, DMSO-d₆) (5:6 mixture of rotamers) δ 13.15 (br. s, 1H), 11.10 (s, 1H), 8.54-8.64 (m, 2H), 8.50 (dd, 1H), 8.32 (s, 1H), 7.94 (s, 1H), 7.59 (dd, 1H), 7.22/7.20 (s, 1H) (rotamers), 6.44 (t, 1H), 4.92/4.72 (d, 1H) (rotamers), 4.33-4.57/3.93-4.03 (m, 3H) (rotamers), 4.06 (s, 3H), 2.91/2.76 (s, 3H) (rotamers), 2.15-2.27 (m, 2H), 1.62-2.15 (m, 6H), 1.22/1.18 (d, 3H) (rotamers). MS ESI, m/z=534 [M+H]⁺.

2-((1R,4r)-4-((R)-2-Hydroxy-N-methylpropanamido)cyclohexyl)-6-methoxy-N-(1-(1-methyl-1H-pyrazol-4-yl)-2-oxo-1,2-dihydropyridin-3-yl)-2H-indazole-5-carboxamide (Example 15)

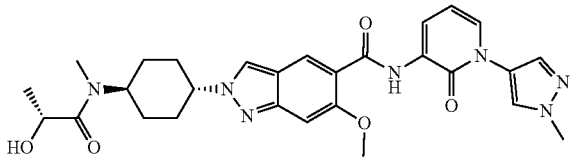 [SMILES: COc1cc2nn([C@H]3CC[C@H](N(C)C(=O)[C@@H](C)O)CC3)cc2cc1C(=O)Nc1cccn(-c2cnn(C)c2)c1=O]

To a solution of 2-((1R,4r)-4-((R)-2-hydroxy-N-methylpropanamido)cyclohexyl)-6-methoxy-2H-indazole-5-carboxylic acid (Int 6) (150 mg, 0.4 mmol), HATU (213 mg, 0.6 mmol) and DIPEA (209 µL, 1.2 mmol) in DMF (6 mL) at 25° C. under N₂ atmosphere was added 3-amino-1-(1-methyl-1H-pyrazol-4-yl)pyridin-2(1H)-one (114 mg, 0.6 mmol). The reaction mixture was stirred at 25° C. for 16 h. The mixture was purified directly by C18-flash chromatography (eluting with 0-100% MeCN in water (0.1% NH₄OH)), followed by prep. HPLC (Xbridge® BEH OBD C18 5 µm 30×150 mm; elution gradient 21-41% MeCN in water (10 mM NH₄HCO₃+0.1% NH₄OH) over 8 min; 60 mL/min) to afford 2-((1R,4r)-4-((R)-2-hydroxy-N-methylpropanamido)cyclohexyl)-6-methoxy-N-(1-(1-methyl-1H-pyrazol-4-yl)-2-oxo-1,2-dihydropyridin-3-yl)-2H-indazole-5-carboxamide (64 mg, 30%), Example 15, as a colorless solid. ¹H NMR (400 MHz, DMSO-d₆) (5:6 mixture of rotamers) δ 11.09 (s, 1H), 8.55-8.62 (m, 2H), 8.50 (dd, 1H), 8.33 (s, 1H), 7.87 (s, 1H), 7.58 (dd, 1H), 7.22/7.20 (s, 1H) (rotamers), 6.45 (t, 1H), 4.91/4.73 (d, 1H) (rotamers), 4.34-4.57/3.94-4.04 (m, 3H) (rotamers), 4.07 (s, 3H), 3.91 (s, 3H), 2.91/2.77 (s, 3H) (rotamers), 2.15-2.28 (m, 2H), 1.62-2.15 (m, 6H), 1.22/1.19 (d, 1H) (rotamers). MS ESI, m/z=548 [M+H]⁺.

2-((1R,4r)-4-((R)-2-Hydroxy-N-methylpropanamido)cyclohexyl)-6-methoxy-N-(1-(1-methyl-1H-1,2,3-triazol-4-yl)-2-oxo-1,2-dihydropyridin-3-yl)-2H-indazole-5-carboxamide (Example 16)

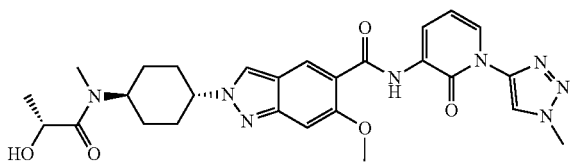 [SMILES: COc1cc2nn([C@H]3CC[C@H](N(C)C(=O)[C@@H](C)O)CC3)cc2cc1C(=O)Nc1cccn(-c2cn(C)nn2)c1=O]

3-Amino-1-(1-methyl-1H-1,2,3-triazol-4-yl)pyridin-2(1H)-one

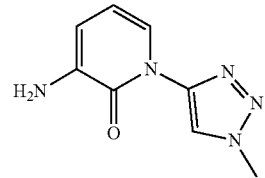

To a suspension of 3-aminopyridin-2(1H)-one (100 mg, 0.9 mmol), 4-bromo-1-methyl-1H-1,2,3-triazole (221 mg, 1.4 mmol), Cs₂CO₃ (592 mg, 1.8 mmol) and copper(I) iodide (35 mg, 0.2 mmol) in 1,4-dioxane (10 mL) at 25° C. under N₂ atmosphere was added N,N'-dimethylethylenediamine (160 mg, 1.8 mmol). The resulting mixture was heated at 105° C. for 16 h. The reaction was carried out 6 times in parallel on the same scale. The combined reaction mixtures were filtered through celite. The filtrate was concentrated under reduced pressure. The residue was purified by C18 flash chromatography twice (eluting with 0-30% MeCN in water (0.05% NH₄OH) and then with 0-30% MeCN in water (0.1% HCl)), followed by prep. HPLC (YMC-Actus Triart C18 5 µm 30×150 mm; elution gradient 5-20% MeCN in water (10 mM NH₄HCO₃+0.1% NH₄OH) over 8 min; 60 mL/min) and further by C18 flash chromatography (eluting with 0-30% MeCN in water (0.05% NH₄OH)) to afford 3-amino-1-(1-methyl-1H-1,2,3-triazol-4-yl)pyridin-2(1H)-one (53 mg, 5%) as a yellow solid. ¹H NMR (400 MHz, DMSO-d₆) δ 8.64 (s, 1H), 7.62 (d, 1H), 6.50 (d, 1H), 6.27 (t, 1H), 5.34 (s, 2H), 4.13 (s, 3H). MS ESI, m/z=192 [M+H]⁺.

2-((1R,4r)-4-((R)-2-Hydroxy-N-methylpropanamido)cyclohexyl)-6-methoxy-N-(1-(1-methyl-1H-1,2,3-triazol-4-yl)-2-oxo-1,2-dihydropyridin-3-yl)-2H-indazole-5-carboxamide, Example 16

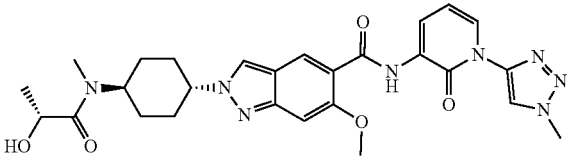 [SMILES: COc1cc2nn([C@H]3CC[C@H](N(C)C(=O)[C@@H](C)O)CC3)cc2cc1C(=O)Nc1cccn(-c2cn(C)nn2)c1=O]

To a solution of 2-((1R,4r)-4-((R)-2-hydroxy-N-methylpropanamido)cyclohexyl)-6-methoxy-2H-indazole-5-carboxylic acid (Int 6) (48 mg, 0.1 mmol), 3-amino-1-(1-methyl-1H-1,2,3-triazol-4-yl)pyridin-2(1H)-one (36 mg, 0.2 mmol) and DIPEA (89 µL, 0.6 mmol) in DMF (3 mL) at 25° C. under N₂ atmosphere was added HATU (58 mg, 0.2 mmol). The reaction mixture was heated at 50° C. for 16 h. The mixture was purified directly by C18-flash chromatography (eluting with 0-100% MeCN in water (0.05% NH₄OH)) and further by prep. HPLC (YMC-Actus Triart C18 5 µm 30×150 mm; elution gradient 25-45% MeCN in water (10 mM NH₄HCO₃+0.1% NH₄OH) over 10 min; 60 mL/min) to afford 2-((1R,4r)-4-((R)-2-hydroxy-N-methylpropanamido)cyclohexyl)-6-methoxy-N-(1-(1-methyl-1H-1,2,3-triazol-4-yl)-2-oxo-1,2-dihydropyridin-3-yl)-2H-indazole-5-carboxamide (40 mg, 61%), Example 16, as a colorless solid. $^1$H NMR (400 MHz, DMSO-$d_6$) (5:6 mixture of rotamers) δ 11.10 (s, 1H), 8.74 (s, 1H), 8.57-8.65 (m, 2H), 8.56 (dd, 1H), 8.07 (dd, 1H), 7.24/7.22 (s, 1H) (rotamers), 6.57 (t, J=7.3 Hz, 1H), 4.92/4.73 (d, 1H) (rotamers), 4.33-4.58/3.93-4.04 (m, 3H) (rotamers), 4.17 (s, 3H), 4.09 (s, 3H), 2.91/2.77 (s, 3H) (rotamers), 2.15-2.28 (m, 2H), 1.61-2.15 (m, 6H), 1.22/1.19 (d, 3H) (rotamers). MS ESI, m/z=549 [M+H]$^+$.

2-((1R,4r)-4-((R)-2-Hydroxy-N-methylpropanamido)cyclohexyl)-6-methoxy-N-(1-(2-methyl-2H-1,2,3-triazol-4-yl)-2-oxo-1,2-dihydropyridin-3-yl)-2H-indazole-5-carboxamide (Example 17)

3-Amino-1-(2-methyl-2H-1,2,3-triazol-4-yl)pyridin-2(1H)-one

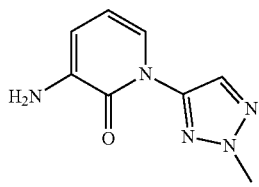

To a suspension of 3-aminopyridin-2(1H)-one (100 mg, 0.9 mmol), 4-bromo-1-methyl-1H-1,2,3-triazole (221 mg, 1.4 mmol), Cs$_2$CO$_3$ (592 mg, 1.8 mmol) and copper(I) iodide (35 mg, 0.2 mmol) in 1,4-dioxane (10 mL) at 25° C. under N$_2$ atmosphere was added N,N'-dimethylethylenediamine (160 mg, 1.8 mmol). The resulting mixture was heated at 105° C. for 16 h. The reaction was carried out 6 times in parallel on the same scale. The combined reaction mixtures were filtered through celite. The filtrate was concentrated under reduced pressure. The residue was purified by C18 flash chromatography (eluting with 5-30% MeCN in water (0.05% NH$_4$OH)) and further by prep. HPLC (Xbridge® BEH OBD C18 5 μm 30×150 mm; elution gradient 5-25% MeCN in water (10 mM NH$_4$HCO$_3$+0.1% NH$_4$OH) over 8 min; 60 mL/min) to afford 3-amino-1-(2-methyl-2H-1,2,3-triazol-4-yl)pyridin-2(1H)-one (150 mg, 14%) as a dark solid. $^1$H NMR (400 MHz, DMSO-$d_6$) δ 8.22 (s, 1H), 7.28 (dd, 1H), 6.48 (dd, 1H), 6.23 (t, 1H), 5.37 (s, 2H), 4.19 (s, 3H). MS ESI, m/z=192 [M+H]$^+$.

2-((1R,4r)-4-((R)-2-Hydroxy-N-methylpropanamido)cyclohexyl)-6-methoxy-N-(1-(2-methyl-2H-1,2,3-triazol-4-yl)-2-oxo-1,2-dihydropyridin-3-yl)-2H-indazole-5-carboxamide, Example 17

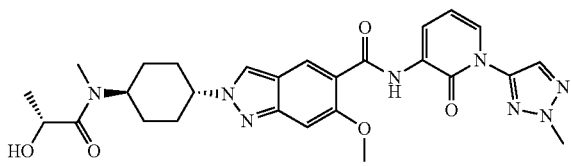 [SMILES: COc1cc2nn([C@H]3CC[C@H](N(C)C(=O)[C@@H](C)O)CC3)cc2cc1C(=O)Nc1cccn(-c2cnn(C)n2)c1=O]

To a solution of 2-((1R,4r)-4-((R)-2-hydroxy-N-methylpropanamido)cyclohexyl)-6-methoxy-2H-indazole-5-carboxylic acid (Int 6) (60 mg, 0.2 mmol), 3-amino-1-(2-methyl-2H-1,2,3-triazol-4-yl)pyridin-2(1H)-one (40 mg, 0.2 mmol) and DIPEA (112 μL, 0.6 mmol) in DMF (2 mL) at 25° C. under N$_2$ atmosphere was added HATU (91 mg, 0.24 mmol). The reaction mixture was stirred at 50° C. for 15 h. The mixture was purified directly by prep. HPLC (Xbridge® BEH OBD C18 5 μm 30×150 mm; elution gradient 25-42% MeCN in water (10 mM NH$_4$HCO$_3$+0.1% NH$_4$OH) over 8 min; 60 mL/min) to afford 2-((1R,4r)-4-((R)-2-hydroxy-N-methylpropanamido)cyclohexyl)-6-methoxy-N-(1-(2-methyl-2H-1,2,3-triazol-4-yl)-2-oxo-1,2-dihydropyridin-3-yl)-2H-indazole-5-carboxamide (34 mg, 39%), Example 17, as a colorless solid. $^1$H NMR (400 MHz, DMSO-$d_6$) (5:6 mixture of rotamers) δ 11.09 (s, 1H), 8.56-8.65 (m, 2H), 8.54 (dd, 1H), 8.28 (s, 1H), 7.73 (dd, 1H), 7.23/7.21 (s, 1H) (rotamers), 6.53 (t, 1H), 4.94/4.75 (d, 1H) (rotamers), 4.33-4.58/3.93-4.03 (m, 3H) (rotamers), 4.23 (s, 3H), 4.07 (s, 3H), 2.91/2.76 (s, 3H) (rotamers), 2.14-2.28 (m, 2H), 1.62-2.14 (m, 6H), 1.22/1.18 (d, 3H) (rotamers). MS ESI, m/z=549 [M+H]$^+$.

6-Methoxy-N-(1-methyl-2-oxo-1,2-dihydropyridin-3-yl)-2-((1r,4r)-4-(2-oxopyrrolidin-1-yl)cyclohexyl)-2H-indazole-5-carboxamide (Example 18)

2-((1r,4r)-4-(4-Chlorobutanamido)cyclohexyl)-6-methoxy-N-(1-methyl-2-oxo-1,2-dihydropyridin-3-yl)-2H-indazole-5-carboxamide

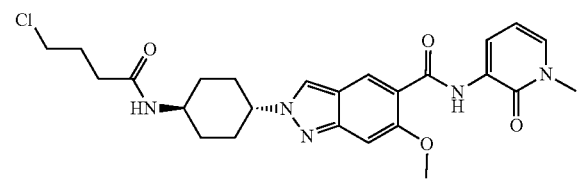 [SMILES: COc1cc2nn([C@H]3CC[C@H](NC(=O)CCCCl)CC3)cc2cc1C(=O)Nc1cccn(C)c1=O]

To a solution of the HCl salt of 2-((1r,4r)-4-aminocyclohexyl)-6-methoxy-N-(1-methyl-2-oxo-1,2-dihydropyridin-3-yl)-2H-indazole-5-carboxamide (Int 7) (150 mg, 0.3 mmol) and TEA (165 μL, 1.1 mmol) in DCM (1 mL) was added 4-chlorobutanoyl chloride (98 mg, 0.7 mmol). The resulting mixture was stirred at 25° C. for 1 h. The mixture was purified directly by C18-flash chromatography (eluting with 0-100% MeCN in water (0.1% NH$_4$OH)) to afford 2-((1r,4r)-4-(4-chlorobutanamido)cyclohexyl)-6-methoxy-N-(1-methyl-2-oxo-1,2-dihydropyridin-3-yl)-2H-indazole-5-carboxamide (90 mg, 53%) as a light-yellow solid. $^1$H NMR (400 MHz, DMSO-$d_6$) δ 11.03 (br. s, 1H), 8.54-8.62 (m, 2H), 8.47 (br. s, 1H), 8.44 (dd, 1H), 7.44 (dd, 1H), 7.19-7.24 (m, 1H), 6.30 (t, 1H), 4.43-4.54 (m, 1H), 4.06 (s, 3H), 3.58-3.66 (m, 3H), 3.55 (s, 3H), 2.06-2.29 (m, 5H), 1.85-2.06 (m, 5H), 1.58-1.72 (m, 1H), 1.36-1.51 (m, 1H). MS ESI, m/z=500/502 (2:1) [M+H]$^+$.

6-Methoxy-N-(1-methyl-2-oxo-1,2-dihydropyridin-3-yl)-2-((1r,4r)-4-(2-oxopyrrolidin-1-yl)cyclohexyl)-2H-indazole-5-carboxamide, Example 18

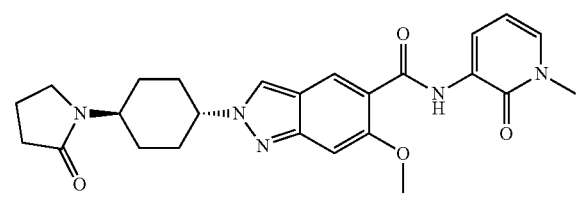 [SMILES: COc1cc2nn([C@H]3CC[C@H](N4CCCC4=O)CC3)cc2cc1C(=O)Nc1cccn(C)c1=O]

To a solution of potassium tert-butoxide (9 mg, 0.1 mmol) in THF (4 mL) was added 2-((1r,4r)-4-(4-chlorobutanamido)cyclohexyl)-6-methoxy-N-(1-methyl-2-oxo-1,2-dihydropyridin-3-yl)-2H-indazole-5-carboxamide (20 mg, 0.04 mmol). The resulting mixture was stirred at 50° C. for 10 h under N₂ atmosphere. The reaction was carried out twice in parallel on the same scale. The combined reaction mixtures were purified directly by C18 flash chromatography (eluting with 0-100% MeCN in water (0.1% NH₄OH)) and further by prep. HPLC (YMC-Actus Triart C18 5 μm 30×150 mm; elution gradient 30-40% MeCN in water (10 mM NH₄HCO₃+0.1% NH₄OH) over 8 min; 60 mL/min) to afford 6-methoxy-N-(1-methyl-2-oxo-1,2-dihydropyridin-3-yl)-2-((1r,4r)-4-(2-oxopyrrolidin-1-yl)cyclohexyl)-2H-indazole-5-carboxamide (15 mg, 41%), Example 18, as a colorless solid. ¹H NMR (400 MHz, DMSO-d₆) δ 11.04 (s, 1H), 8.58 (s, 1H), 8.57 (s, 1H), 8.45 (dd, 1H), 7.43 (dd, 1H), 7.22 (s, 1H), 6.31 (t, 1H), 4.43-4.54 (m, 1H), 4.07 (s, 3H), 3.84-3.97 (m, 1H), 3.56 (s, 3H), 2.14-2.29 (m, 4H), 1.97-2.11 (m, 2H), 1.92 (p, 2H), 1.65-1.83 (m, 4H). MS ESI, m/z=464 [M+H]⁺.

6-Methoxy-N-(1-methyl-2-oxo-1,2-dihydropyridin-3-yl)-2-((1r,4r)-4-(3-methyl-2-oxoimidazolidin-1-yl)cyclohexyl)-2H-indazole-5-carboxamide (Example 19)

tert-Butyl (2-(((1r,4r)-4-(6-methoxy-5-((1-methyl-2-oxo-1,2-dihydropyridin-3-yl)carbamoyl)-2H-indazol-2-yl)cyclohexyl)amino)ethyl)(methyl)carbamate

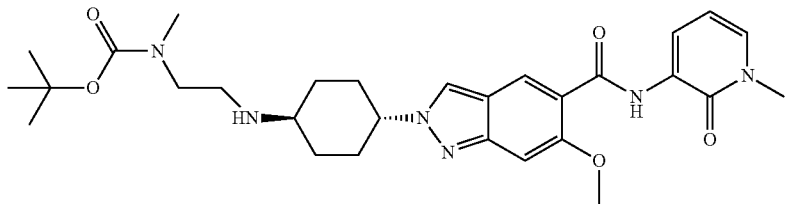 [SMILES: COc1cc2nn([C@H]3CC[C@H](NCCN(C)C(=O)OC(C)(C)C)CC3)cc2cc1C(=O)Nc1cccn(C)c1=O]

tert-Butyl methyl(2-oxoethyl)carbamate (20 mg, 0.1 mmol) was added to a solution of the HCl salt of 2-((1r,4r)-4-aminocyclohexyl)-6-methoxy-N-(1-methyl-2-oxo-1,2-dihydropyridin-3-yl)-2H-indazole-5-carboxamide (Int 7) (79% wt. %) (50 mg, 0.1 mmol) in DCE (4 mL), followed by the addition of sodium triacetoxyborohydride (52 mg, 0.2 mmol). The resulting mixture was stirred at 25° C. for 6 h. The reaction mixture was purified directly by C18 flash chromatography (eluting with 0-100% MeCN in water (0.1% NH₄OH)) to afford tert-butyl (2-(((1r,4r)-4-(6-methoxy-5-((1-methyl-2-oxo-1,2-dihydropyridin-3-yl)carbamoyl)-2H-indazol-2-yl)cyclohexyl)amino)ethyl)(methyl)carbamate (100 mg, 52%) as a brown solid. MS ESI, m/z=553 [M+H]⁺.

6-Methoxy-N-(1-methyl-2-oxo-1,2-dihydropyridin-3-yl)-2-((1r,4r)-4-((2-(methylamino)ethyl)amino)cyclohexyl)-2H-indazole-5-carboxamide

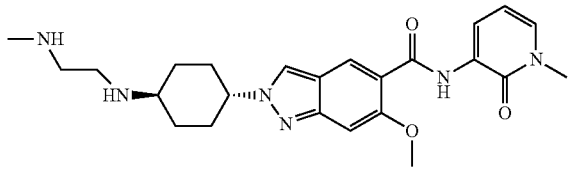

To a solution of tert-butyl (2-(((1r,4r)-4-(6-methoxy-5-((1-methyl-2-oxo-1,2-dihydropyridin-3-yl)carbamoyl)-2H-indazol-2-yl)cyclohexyl)amino)ethyl)(methyl)carbamate (95 mg, 0.2 mmol) in DCM (15 mL) was added 2N HCl in dioxane (860 μL, 1.7 mmol), and the resulting solution was stirred at 25° C. for 4 h. The mixture was concentrated under reduced pressure to afford the HCl salt of 6-methoxy-N-(1-methyl-2-oxo-1,2-dihydropyridin-3-yl)-2-((1r,4r)-4-((2-(methylamino)ethyl)amino)cyclohexyl)-2H-indazole-5-carboxamide (78 mg, 100%) as a brown solid. MS ESI, m/z=453 [M+H]⁺.

6-Methoxy-N-(1-methyl-2-oxo-1,2-dihydropyridin-3-yl)-2-((1r,4r)-4-(3-methyl-2-oxoimidazolidin-1-yl)cyclohexyl)-2H-indazole-5-carboxamide, Example 19

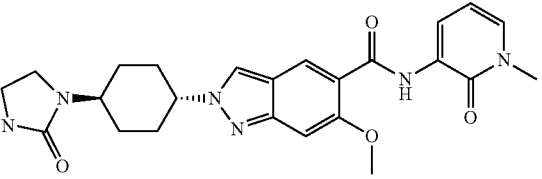

To a solution of 6-methoxy-N-(1-methyl-2-oxo-1,2-dihydropyridin-3-yl)-2-((1r,4r)-4-((2-(methylamino)ethyl)amino)cyclohexyl)-2H-indazole-5-carboxamide hydrochloride (30 mg, 0.1 mmol) and DIPEA (46 μL, 0.3 mmol) in DCE (5 mL) under N₂ atmosphere was added CDI (13 mg, 0.1 mmol). The resulting solution was stirred at 60° C. for 5 h. The reaction was carried out twice in parallel on the same scale. The combined reaction mixtures were purified directly by prep. HPLC (YMC-Actus Triart C18 ExRS 5 μm 30×150 mm; elution gradient 21-43% MeCN in water (10 mM NH₄HCO₃+0.1% NH₄OH) over 8 min; 60 mL/min) to afford 6-methoxy-N-(1-methyl-2-oxo-1,2-dihydropyridin-3-yl)-2-((1r,4r)-4-(3-methyl-2-oxoimidazolidin-1-yl)cyclohexyl)-2H-indazole-5-carboxamide (10 mg, 17%), Example 19, as a light-yellow solid. ¹H NMR (300 MHz, DMSO-d₆) δ 11.04 (s, 1H), 8.54-8.60 (m, 2H), 8.45 (dd, 1H), 7.43 (dd, 1H), 7.22 (s, 1H), 6.31 (t, 1H), 4.40-4.54 (m, 1H), 4.06 (s, 3H), 3.59-3.74 (m, 1H), 3.56 (s, 3H), 3.16-3.29 (m, 4H), 2.65 (s, 3H), 2.12-2.31 (m, 2H), 1.92-2.12 (m, 2H), 1.64-1.83 (m, 4H). MS ESI, m/z=479 [M+H]⁺.

6-Methoxy-N-(1-methyl-2-oxo-1,2-dihydropyridin-3-yl)-2-((5s,8s)-1-methyl-2-oxo-3-oxa-1-azaspiro[4.5]decan-8-yl)-2H-indazole-5-carboxamide (Example 20)

(4-(5-Bromo-6-methoxy-2H-indazol-2-yl)cyclohexyl)methanol

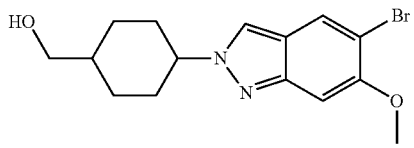 [SMILES: COc1cc2nn(C3CCC(CO)CC3)cc2cc1Br]

To a solution of (4-aminocyclohexyl)methanol (4.2 g, 25.4 mmol) in i-PrOH (40 mL) at rt was added 5-bromo-4-methoxy-2-nitrobenzaldehyde (Int 1) (6.6 g, 25.4 mmol) and TEA (10.6 mL, 76.1 mmol) under $N_2$ atmosphere. The resulting mixture was stirred at 90° C. for 30 min, then cooled to rt, followed by the addition of tri-n-butylphosphine (15.4 g, 76.1 mmol). The reaction mixture was stirred at 90° C. for 10 h. The mixture was cooled to rt and purified directly by C-18 flash chromatography (eluting with 0-100% MeCN in water (1% $NH_4OH$)) to yield a black liquid, which was used in the next step without further purification. MS ESI, m/z=339/341 [M+H]$^+$.

(4-(5-Bromo-6-methoxy-2H-indazol-2-yl)cyclohexyl)methyl carbamate

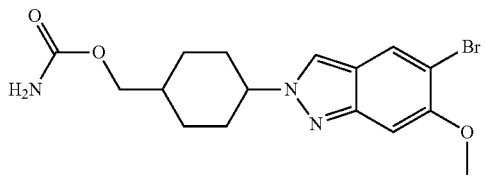 [SMILES: COc1cc2nn(C3CCC(COC(N)=O)CC3)cc2cc1Br]

To a solution of crude (4-(5-bromo-6-methoxy-2H-indazol-2-yl)cyclohexyl)methanol (7.9 g) in DCM (1000 mL) at 0° C. was added 2,2,2-trichloroacetyl isocyanate (5.3 g, 32.0 mmol). The resulting solution was warmed to rt and stirred for 2 h. Subsequently, MeOH (20 mL) and $K_2CO_3$ (320 mg, 2.3 mmol) were added. The resulting mixture was stirred at rt for 3 h and then concentrated under reduced pressure.

The residue was purified directly by C-18 flash chromatography (eluting with 0-100% MeCN in water (1% $NH_4OH$)) to yield (4-(5-bromo-6-methoxy-2H-indazol-2-yl)cyclohexyl)methyl carbamate (6.6 g, 85%) as a dark oil. MS ESI, m/z=382/384 [M+H]$^+$.

(5s,8s)-8-(5-Bromo-6-methoxy-2H-indazol-2-yl)-3-oxa-1-azaspiro[4.5]decan-2-one

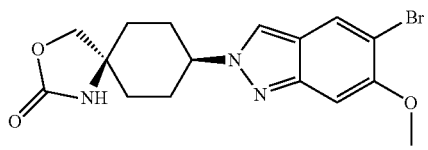 [SMILES: COc1cc2nn([C@H]3CC[C@@]4(CC3)COC(=O)N4)cc2cc1Br]

(5r,8r)-8-(5-Bromo-6-methoxy-2H-indazol-2-yl)-3-oxa-1-azaspiro[4.5]decan-2-one

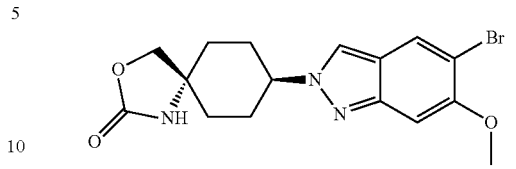

To a suspension of magnesium oxide (3.1 g, 77.0 mmol), phenyl-$\lambda^3$-iodanediyl diacetate (15.1 g, 46.9 mmol) and crude (4-(5-bromo-6-methoxy-2H-indazol-2-yl)cyclohexyl)methyl carbamate (6.4 g) in DCM (80 mL) at 20° C. under $N_2$ atmosphere was added [$Rh_2(OAc)_4$] (1.5 g, 3.4 mmol). The resulting mixture was stirred at 40° C. for 15 h. The reaction mixture was then filtered through a paper filter. The filtrate was diluted with DCM (200 mL), and washed with brine (100 mL), dried over $Na_2SO_4$, filtered and then concentrated under reduced pressure. The residue was purified by C-18 flash chromatography (eluting with 0-100% MeCN in water (1% $NH_4OH$)) and further by prep. SFC (GreenSep™ Basic, 5 μm 30 mm×150 mm; isocratic with 25% MeOH (0.5% 2M $NH_3$-MeOH) in $CO_2$ (35° C., 100 bar); 80 mL/min; to afford (5s,8s)-8-(5-bromo-6-methoxy-2H-indazol-2-yl)-3-oxa-1-azaspiro[4.5]decan-2-one (60 mg, 1%) and (5r,8r)-8-(5-bromo-6-methoxy-2H-indazol-2-yl)-3-oxa-1-azaspiro[4.5]decan-2-one (150 mg, 2%), both as yellow solids. (5s,8s)—Isomer: $^1$H NMR (300 MHz, DMSO-$d_6$) δ 8.41 (s, 1H), 8.30 (s, 1H), 8.03 (s, 1H), 7.07 (s, 1H), 4.35-4.52 (m, 1H), 4.04 (s, 2H), 3.87 (s, 3H), 1.65-2.23 (m, 8H). MS ESI, m/z=380/382 (1:1) [M+H]$^+$. (5r,8r)—Isomer: $^1$H NMR (300 MHz, DMSO-$d_6$) δ 8.30 (s, 1H), 7.99 (s, 1H), 7.85 (s, 1H), 7.12 (s, 1H), 4.37-4.51 (m, 1H), 4.22 (s, 2H), 3.86 (s, 3H), 1.65-2.15 (m, 8H). MS ESI, m/z=380/382 (1:1) [M+H]$^+$.

(5s,8s)-8-(5-Bromo-6-methoxy-2H-indazol-2-yl)-1-methyl-3-oxa-1-azaspiro[4.5]decan-2-one

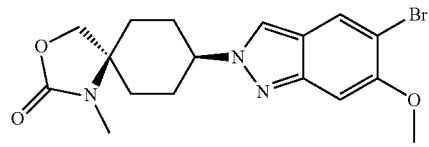 [SMILES: COc1cc2nn([C@H]3CC[C@@]4(CC3)COC(=O)N4C)cc2cc1Br]

To a suspension of (5s,8s)-8-(5-bromo-6-methoxy-2H-indazol-2-yl)-3-oxa-1-azaspiro[4.5]decan-2-one (60 mg, 0.2 mmol) and NaH (60 wt. %) (10 mg, 0.2 mmol) in DMF (6 mL) at 25° C. under $N_2$ atmosphere was added iodomethane (67 mg, 0.5 mmol). The reaction mixture was stirred at 25° C. for 15 h, then quenched with saturated aq. $NH_4Cl$ solution (5 mL) and purified directly by C18-flash chromatography (eluting with 0-100% MeCN in water (0.1% FA)) to afford (5s,8s)-8-(5-bromo-6-methoxy-2H-indazol-2-yl)-1-methyl-3-oxa-1-azaspiro[4.5]decan-2-one (45 mg, 72%) as a red solid. $^1$H NMR (300 MHz, DMSO-d6) δ 8.43 (s, 1H), 7.98 (s, 1H), 7.15 (s, 1H), 4.58-4.67 (m, 1H), 4.21 (s, 2H), 3.87 (s, 3H), 2.58 (s, 3H), 2.35-2.48 (m, 2H), 1.87-2.12 (m, 4H), 1.40-1.58 (m, 2H). MS ESI, m/z=394/396 (1:1) [M+H]$^+$.

Methyl 6-methoxy-2-((5s,8s)-1-methyl-2-oxo-3-oxa-1-azaspiro[4.5]decan-8-yl)-2H-indazole-5-carboxylate

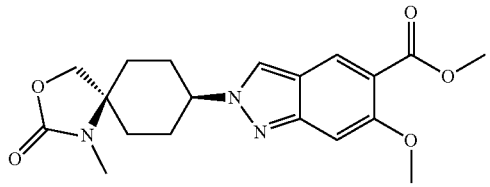 [SMILES: COC(=O)c1cc2cn([C@H]3CC[C@@]4(CC3)COC(=O)N4C)nc2cc1OC]

A mixture of (5s,8s)-8-(5-bromo-6-methoxy-2H-indazol-2-yl)-1-methyl-3-oxa-1-azaspiro[4.5]decan-2-one (45 mg, 0.1 mmol), Pd(dppf)Cl₂ (17 mg, 0.02 mmol) and TEA (250 μL, 1.8 mmol) in MeOH (10 mL) was stirred in a sealed vessel under CO atmosphere at 10 atm, and then heated at 100° C. for 12 h. The reaction mixture was concentrated under reduced pressure. The residue was purified by C18-flash chromatography (eluting with 0-100% MeCN in water (1% NH₄OH)) to afford methyl 6-methoxy-2-((5s,8s)-1-methyl-2-oxo-3-oxa-1-azaspiro[4.5]decan-8-yl)-2H-indazole-5-carboxylate (40 mg, 94%) as a colorless solid. ¹H NMR (300 MHz, DMSO-d₆) δ 8.60 (s, 1H), 8.09 (s, 1H), 7.09 (s, 1H), 4.58-4.69 (m, 1H), 4.22 (s, 2H), 3.83 (s, 3H), 3.79 (s, 3H), 2.58 (s, 3H), 1.91-2.08 (m, 8H). MS ESI, m/z=374 [M+H]⁺.

6-Methoxy-2-((5s,8s)-1-methyl-2-oxo-3-oxa-1-azaspiro[4.5]decan-8-yl)-2H-indazole-5-carboxylic acid

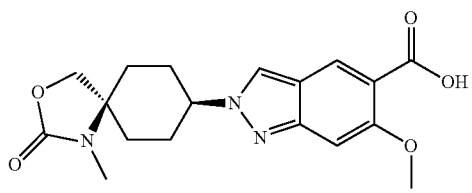 [SMILES: COc1cc2nn([C@H]3CC[C@@]4(CC3)COC(=O)N4C)cc2cc1C(=O)O]

To a solution of methyl 6-methoxy-2-((5s,8s)-1-methyl-2-oxo-3-oxa-1-azaspiro[4.5]decan-8-yl)-2H-indazole-5-carboxylate (38 mg, 0.1 mmol) in MeOH (1 mL) at 25° C. was added a solution of LiOH (7 mg, 0.3 mmol) in water (1 mL). The resulting solution was stirred at 25° C. for 10 h. The pH of the reaction mixture was adjusted to pH 6 with 2N HCl. The reaction mixture was purified directly by C18-flash chromatography (eluting with 0-100% MeCN in water (0.1% FA)) to afford 6-methoxy-2-((5s,8s)-1-methyl-2-oxo-3-oxa-1-azaspiro[4.5]decan-8-yl)-2H-indazole-5-carboxylic acid (35 mg, 96%) as a yellow solid. ¹H NMR (300 MHz, DMSO-d₆) δ 8.53 (s, 1H), 7.96 (s, 1H), 7.02 (s, 1H), 4.58-4.68 (m, 1H), 4.22 (s, 2H), 3.81 (s, 3H), 2.57 (s, 3H), 1.87-2.16 (m, 8H). MS ESI, m/z=360 [M+H]⁺.

6-Methoxy-N-(1-methyl-2-oxo-1,2-dihydropyridin-3-yl)-2-((5s,8s)-1-methyl-2-oxo-3-oxa-1-azaspiro[4.5]decan-8-yl)-2H-indazole-5-carboxamide, Example 20

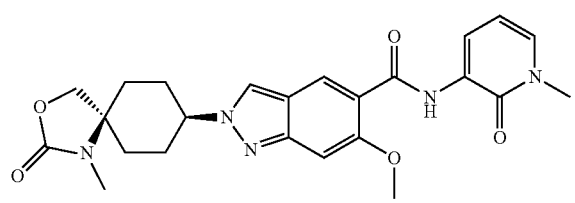 [SMILES: COc1cc2nn([C@H]3CC[C@@]4(CC3)COC(=O)N4C)cc2cc1C(=O)Nc1cccn(C)c1=O]

To a solution of 6-methoxy-2-((5s,8s)-1-methyl-2-oxo-3-oxa-1-azaspiro[4.5]decan-8-yl)-2H-indazole-5-carboxylic acid (33 mg, 0.1 mmol), DIPEA (17 μL, 0.1 mmol) and T3P (50 wt. % in EtOAc) (62 mg, 0.1 mmol) in DCM (0.5 mL) at 25° C. under N₂ atmosphere was added (62 mg, 0.1 mmol) 3-amino-1-methylpyridin-2(1H)-one (24 mg, 0.2 mmol). The resulting solution was stirred at 50° C. for 10 h. The reaction mixture was concentrated under reduced pressure and then purified by prep. HPLC (Waters Xbridge® Shield RP18 OBD, 5 μm 30×150 mm; elution gradient 20-35% MeCN in water (10 mM NH₄HCO₃+0.1% NH₄OH) over 8 min, then 35% for 2 min; 60 mL/min) to afford 6-methoxy-N-(1-methyl-2-oxo-1,2-dihydropyridin-3-yl)-2-((5s,8s)-1-methyl-2-oxo-3-oxa-1-azaspiro[4.5]decan-8-yl)-2H-indazole-5-carboxamide (15 mg, 35%), Example 20, as a colorless solid. ¹H NMR (300 MHz, DMSO-d₆) δ 11.05 (s, 1H), 8.72 (s, 1H), 8.59 (s, 1H), 8.45 (dd, 1H), 7.44 (dd, 1H), 7.26 (s, 1H), 6.31 (t, 1H), 4.64-4.73 (m, 1H), 4.23 (s, 2H), 4.08 (s, 3H), 3.56 (s, 3H), 2.59 (s, 3H), 1.90-2.17 (m, 4H), 1.43-1.61 (m, 2H). MS ESI, m/z=466 [M+H]⁺.

6-Methoxy-N-(1-methyl-2-oxo-1,2-dihydropyridin-3-yl)-2-((5r,8r)-1-methyl-2-oxo-3-oxa-1-azaspiro[4.5]decan-8-yl)-2H-indazole-5-carboxamide (Example 21)

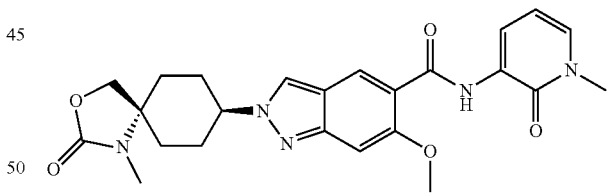

6-Methoxy-N-(1-methyl-2-oxo-1,2-dihydropyridin-3-yl)-2-((5r,8r)-1-methyl-2-oxo-3-oxa-1-azaspiro[4.5]decan-8-yl)-2H-indazole-5-carboxamide was prepared from (5r,8r)-8-(5-bromo-6-methoxy-2H-indazol-2-yl)-3-oxa-1-azaspiro[4.5]decan-2-one analogously to the synthesis of 6-methoxy-N-(1-methyl-2-oxo-1,2-dihydropyridin-3-yl)-2-((5s,8s)-1-methyl-2-oxo-3-oxa-1-azaspiro[4.5]decan-8-yl)-2H-indazole-5-carboxamide (Example 20) described above. Crude 6-methoxy-N-(1-methyl-2-oxo-1,2-dihydropyridin-3-yl)-2-((5r,8r)-1-methyl-2-oxo-3-oxa-1-azaspiro[4.5]decan-8-yl)-2H-indazole-5-carboxamide was purified by prep. HPLC (YMC-Actus Triart C18 5 μm 30×150 mm; elution gradient 20-50% MeCN in water (10 mM NH₄HCO₃+0.1% NH₄OH) over 8 min; 60 mL/min) and then by prep. SFC (DAICEL DCpak® P4VP, 5 μm 30 mm×250 mm; isocratic with 50% IPA (0.5% 2M NH₃-MeOH) in CO₂ (35° C., 100 bar); 60 mL/min) to give 6-methoxy-N-(1-methyl-2-oxo-1, 2-dihydropyridin-3-yl)-2-((5r,8r)-1-methyl-2-oxo-3-oxa-1-azaspiro[4.5]decan-8-yl)-2H-indazole-5-carboxamide (10 mg, 14% yield over 4 steps), Example 21, as a colorless solid. ¹H NMR (300 MHz, DMSO-d₆) δ 11.04 (s, 1H), 8.58 (s, 2H), 8.45 (dd, 1H), 7.43 (dd, 1H), 7.23 (s, 1H), 6.31 (t, 1H), 4.45-4.61 (m, 1H), 4.27 (s, 2H), 4.06 (s, 3H), 3.56 (s, 3H), 2.71 (s, 3H), 2.09-2.23 (m, 2H), 1.91-2.09 (m, 4H), 1.62-1.78 (m, 2H). MS ESI, m/z=466 [M+H]⁺.

6-Methoxy-N-(1-methyl-2-oxo-1,2-dihydropyridin-3-yl)-2-((1r,4r)-4-(2-oxopyridin-1(2H)-yl)cyclohexyl)-2H-indazole-5-carboxamide (Example 22)

tert-Butyl ((1r,4r)-4-(2-oxopyridin-1(2H)-yl)cyclohexyl)carbamate

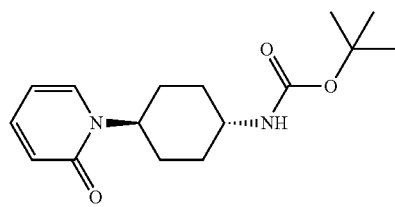 [SMILES: CC(C)(C)OC(=O)N[C@H]1CC[C@H](n2ccccc2=O)CC1]

To a solution of (1s,4s)-4-((tert-butoxycarbonyl)amino) cyclohexyl 4-methylbenzenesulfonate (1.0 g, 2.7 mmol) and Cs₂CO₃ (2.7 g, 8.1 mmol) in THF (30 mL) was added pyridin-2(1H)-one (0.5 g, 5.4 mmol). The reaction mixture was stirred at 90° C. for 24 h and then quenched with water (300 mL) and extracted with EtOAc (300 mL×2). The organic layer was concentrated under reduced pressure. The residue was purified by C18-flash chromatography (eluting with 0-70% MeCN in water (0.1% NH₄OH)) to afford tert-butyl ((1r,4r)-4-(2-oxopyridin-1(2H)-yl)cyclohexyl)carbamate (205 mg, 26%) as a colorless solid. ¹H NMR (300 MHz, DMSO-d₆) δ 7.70 (dd, 1H), 7.34 (ddd, 1H), 6.77 (d, 1H), 6.34 (dd, 1H), 6.21 (td), 4.60 (tt, 1H), 3.23-3.41 (m, 1H), 1.80-1.95 (m, 2H), 1.56-1.78 (m, 4H), 1.37 (s, 11H). MS ESI, m/z=293 [M+H]⁺.

1-((1r,4r)-4-Aminocyclohexyl)pyridin-2(1H)-one

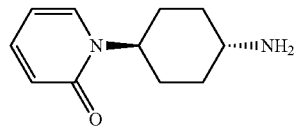

To a solution of tert-butyl ((1r,4r)-4-(2-oxopyridin-1(2H)-yl)cyclohexyl)carbamate (200 mg, 0.7 mmol) in DCM (5 mL) was added 4N HCl in dioxane (1.7 mL, 6.8 mmol). The resulting mixture was stirred at 25° C. for 5 h. The reaction mixture was concentrated under reduced pressure to afford the HCl salt of 1-((1r,4r)-4-aminocyclohexyl)pyridin-2(1H)-one (156 mg, 100%) as a pale yellow solid, which was used without further purification. ¹H NMR (300 MHz, DMSO-d₆) δ 7.68 (dd, 1H), 7.36 (ddd, 1H), 6.36 (dd, 1H), 6.24 (td, 1H), 5.88 (br. s, 2H), 4.64 (p, 8 1H), 2.92-3.14 (m, 1H), 1.99-2.13 (m, 2H), 1.66-1.87 (m, 4H), 1.39-1.63 (m, 2H). MS ESI, m/z=193 [M+H]⁺.

1-((1r,4r)-4-(5-Bromo-6-methoxy-2H-indazol-2-yl) cyclohexyl)pyridin-2(1H)-one

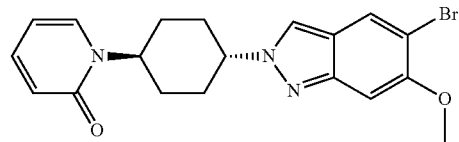 [SMILES: COc1cc2nn([C@H]3CC[C@H](n4ccccc4=O)CC3)cc2cc1Br]

To a solution of the HCl salt of 1-((1r,4r)-4-aminocyclohexyl)pyridin-2(1H)-one (145 mg, 0.6 mmol) and TEA (192 mg, 1.9 mmol) in i-PrOH (5 mL) was added 5-bromo-4-methoxy-2-nitrobenzaldehyde (Int 1) (165 mg, 0.6 mmol) at 25° C. under N₂ atmosphere. The resulting mixture was stirred at 80° C. for 1 h, then cooled to rt and followed by the addition of tri-n-butylphosphine (385 mg, 1.9 mmol). The reaction mixture was stirred at 80° C. for 13 h and then concentrated under reduced pressure. The residue was purified by C18-flash chromatography (eluting with 0-100% MeCN in water (0.1% NH₄OH)) to give a mixture of the desired product and tri-n-butylphosphine. The mixture was then washed with PE (25 mL) to afford 1-((1r,4r)-4-(5-bromo-6-methoxy-2H-indazol-2-yl)cyclohexyl)pyridin-2 (1H)-one (170 mg, 67%) as a pale yellow solid. ¹H NMR (300 MHz, DMSO-d₆) δ 8.35 (s, 1H), 7.98 (s, 1H), 7.77 (dd, 1H), 7.39 (ddd, 1H), 7.12 (s, 1H), 6.40 (dd, 1H), 6.28 (td, 1H), 4.79-4.93 (m, 1H), 4.48-4.62 (m, 1H), 3.87 (s, 3H), 2.19-2.32 (m, 2H), 1.82-2.19 (m, 6H). MS ESI, m/z=402/ 404 [M+H]⁺.

Methyl 6-methoxy-2-((1r,4r)-4-(2-oxopyridin-1 (2H)-yl)cyclohexyl)-2H-indazole-5-carboxylate

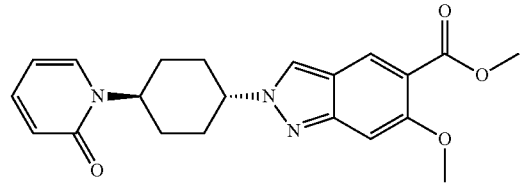 [SMILES: COC(=O)c1cc2cn([C@H]3CC[C@H](n4ccccc4=O)CC3)nc2cc1OC]

The mixture of 1-((1r,4r)-4-(5-bromo-6-methoxy-2H-indazol-2-yl)cyclohexyl)pyridin-2(1H)-one (150 mg, 0.4 mmol), TEA (520 μL, 3.7 mmol) and Pd(dppf)Cl₂—CH₂Cl₂ (46 mg, 0.06 mmol) in MeOH (10 mL) was stirred in a sealed vessel under CO atmosphere at 15 atm, and then heated at 110° C. for 15 h. The reaction mixture was concentrated under reduced pressure. The residue was purified by C18-flash chromatography (eluting with 0-100% MeCN in water (0.1% NH₄OH)) to afford methyl 6-methoxy-2-((1r,4r)-4-(2-oxopyridin-1(2H)-yl)cyclohexyl)-2H-indazole-5-carboxylate (120 mg, 84%) as a colorless solid. ¹H NMR (400 MHz, DMSO-d₆) δ 8.52 (d, 1H), 8.09 (s, 1H), 7.77 (dd, 1H), 7.39 (ddd, 1H), 7.06 (s, 1H), 6.41 (dd, 1H), 6.28 (td, 1H), 4.82-4.92 (m, 1H), 4.52-4.61 (m, 1H), 3.82 (s, 3H), 3.79 (s, 3H), 2.22-2.31 (m, 2H), 2.05-2.18 (m, 2H), 1.84-2.05 (m, 4H). MS ESI, m/z=382 [M+H]⁺.

6-Methoxy-2-((1r,4r)-4-(2-oxopyridin-1(2H)-yl)cyclohexyl)-2H-indazole-5-carboxylic acid

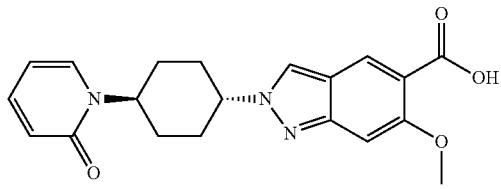 [SMILES: COc1cc2nn([C@H]3CC[C@H](n4ccccc4=O)CC3)cc2cc1C(=O)O]

To a solution of methyl 6-methoxy-2-((1r,4r)-4-(2-oxopyridin-1(2H)-yl)cyclohexyl)-2H-indazole-5-carboxylate (115 mg, 0.3 mmol) in MeOH/water (2:1, 7.5 mL) was added LiOH (22 mg, 0.9 mmol). The resulting mixture were stirred at 25° C. for 12 h. The reaction mixture was acidified to pH 6 with 2N HCl and then purified directly by C18-flash chromatography (eluting with 0-70% MeCN in water (0.1% FA)) to afford 6-methoxy-2-((1r,4r)-4-(2-oxopyridin-1(2H)-yl)cyclohexyl)-2H-indazole-5-carboxylic acid (109 mg, 98%) as a colorless solid. $^1$H NMR (300 MHz, DMSO-$d_6$) δ 8.49 (s, 1H), 8.06 (s, 1H), 7.78 (dd, 1H), 7.39 (ddd, 1H), 7.03 (s, 1H), 6.41 (dd, 1H), 6.28 (td, 1H), 4.80-4.94 (m, 1H), 4.50-4.62 (m, 1H), 3.82 (s, 3H), 2.20-2.33 (m, 2H), 1.82-2.20 (m, 6H). MS ESI, m/z=368 [M+H]$^+$.

6-Methoxy-N-(1-methyl-2-oxo-1,2-dihydropyridin-3-yl)-2-((1r,4r)-4-(2-oxopyridin-1(2H)-yl)cyclohexyl)-2H-indazole-5-carboxamide, Example 22

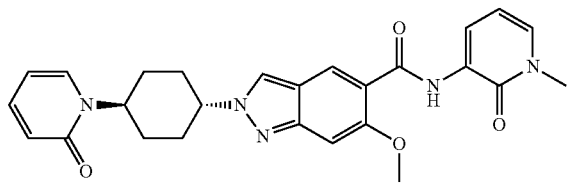 [SMILES: COc1cc2nn([C@H]3CC[C@H](n4ccccc4=O)CC3)cc2cc1C(=O)Nc1cccn(C)c1=O]

To a solution of 6-methoxy-2-((1r,4r)-4-(2-oxopyridin-1(2H)-yl)cyclohexyl)-2H-indazole-5-carboxylic acid (100 mg, 0.3 mmol) and DIPEA (190 µL, 1.1 mmol) in DMF (3 mL) was added HATU (135 mg, 0.4 mmol) at 25° C. under N$_2$ atmosphere. The resulting mixture was stirred at 25° C. for 5 min and followed by the addition of 3-amino-1-methylpyridin-2(1H)-one hydrochloride (87 mg, 0.5 mmol). The reaction mixture was stirred at 25° C. for 12 h. The mixture was purified directly by C18-flash chromatography (eluting with 0-70% MeCN in water (0.1% HCl)) and further by prep. HPLC (Waters Xbridge® BEH OBD C18 5 µm 30×150 mm; elution gradient 15-45% MeCN in water (10 mM NH$_4$HCO$_3$+0.1% NH$_4$OH) over 8 min, then isocratic elution with 45% MeCN in water (10 mM NH$_4$HCO$_3$+0.1% NH$_4$OH); 60 mL/min) to afford 6-methoxy-N-(1-methyl-2-oxo-1,2-dihydropyridin-3-yl)-2-((1r,4r)-4-(2-oxopyridin-1(2H)-yl)cyclohexyl)-2H-indazole-5-carboxamide (93 mg, 72%), Example 22, as a colorless solid. $^1$H NMR (400 MHz, DMSO-$d_6$) δ 11.05 (s, 1H), 8.64 (d, 1H), 8.58 (s, 1H), 8.45 (dd, 1H), 7.78 (dd, 1H), 7.36-7.47 (m, 2H), 7.23 (s, 1H), 6.41 (dd, 1H), 6.26-6.34 (m, 2H), 4.83-4.93 (m, 1H), 4.55-4.65 (m, 1H), 4.07 (s, 3H), 3.56 (s, 3H), 2.23-2.35 (m, 2H), 2.14 (qd, 2H), 1.86-2.07 (m, 4H). MS ESI, m/z=474 [M+H]$^+$.

6-Methoxy-N-(1-methyl-2-oxo-1,2-dihydropyridin-3-yl)-2-(4-(pyridazin-3-yl)cyclohexyl)-2H-indazole-5-carboxamide—Isomer 1 (Example 23) & Isomer 2 (Example 24)

tert-Butyl (4-(pyridazin-3-yl)cyclohex-3-en-1-yl)carbamate

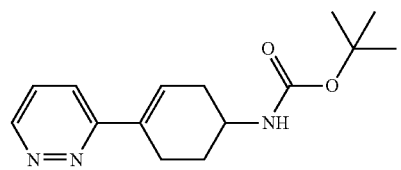 [SMILES: CC(C)(C)OC(=O)NC1CC=C(c2cccnn2)CC1]

A suspension of tert-butyl (4-(4,4,5,5-tetramethyl-1,3,2-dioxaborolan-2-yl)cyclohex-3-en-1-yl)carbamate (2.0 g, 6.2 mmol), 3-chloropyridazine (921 mg, 8.0 mmol), Pd(dppf)Cl$_2$—CH$_2$Cl$_2$ (1.0 g, 1.2 mmol) and K$_2$CO$_3$ (2.6 g, 18.6 mmol) in 1,4-dioxane (30 mL) was heated at 80° C. for 3 h. The reaction mixture was extracted with EtOAc (50 mL×2) and the organic layer was dried over Na$_2$SO$_4$, filtered and concentrated under reduced pressure to give a brown oil. The residue was purified by silica gel chromatography (eluting with 100% EtOAc) to afford tert-butyl (4-(pyridazin-3-yl)cyclohex-3-en-1-yl)carbamate (1.7 g, 97%) as a yellow oil. $^1$H NMR (300 MHz, DMSO-$d_6$) δ 9.07 (dd, 1H), 7.86 (dd, 1H), 7.61 (dd, 1H), 6.89 (d, 1H), 6.63-6.73 (m, 1H), 3.50-3.66 (m, 1H), 2.73-2.88 (m, 1H), 2.42-2.64 (m, 2H), 2.07-2.24 (m, 1H), 1.89-2.03 (m, 1H), 1.50-1.66 (m, 1H), 1.40 (s, 9H). MS ESI, m/z=276 [M+H]$^+$.

tert-Butyl (4-(pyridazin-3-yl)cyclohexyl)carbamate

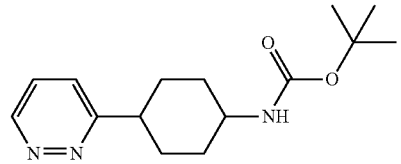 [SMILES: CC(C)(C)OC(=O)NC1CCC(c2cccnn2)CC1]

A suspension of 10 wt. % Palladium on carbon (0.6 g, 0.6 mmol) and tert-butyl (4-(pyridazin-3-yl)cyclohex-3-en-1-yl)carbamate (1.6 g, 5.6 mmol) in EtOAc (30 mL) was stirred at 25° C. under H$_2$ at 1 atm for 2 h. The reaction mixture was filtered through silica gel, and the filtrate was concentrated under reduced pressure to afford tert-butyl (4-(pyridazin-3-yl)cyclohexyl)carbamate (1.6 g, 100%) as a brown oil, which was used without further purification. $^1$H NMR (300 MHz, DMSO-$d_6$) (mixture of stereoisomers) δ 9.02-9.12 (m, 1H), 7.57-7.74 (m, 2H), 6.95/6.80 (d, 1H) (stereoisomers), 3.61-3.78/3.23-3.38 (m, 1H) (stereoisomers), 2.72-3.01 (m, 1H) (stereoisomers), 1.82-1.97 (m, 2H), 1.52-1.77 (m, 4H), 1.22-1.47 (m, 11H). MS ESI, m/z=278 [M+H]$^+$.

4-(Pyridazin-3-yl)cyclohexan-1-amine

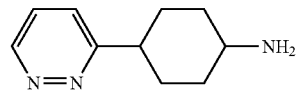 [SMILES: NC1CCC(c2cccnn2)CC1]

A mixture of tert-butyl (4-(pyridazin-3-yl)cyclohexyl)carbamate (500 mg, 1.8 mmol) and 2N HCl in dioxane (9.0 mL, 18.0 mmol) was stirred at 25° C. for 3 h. Then, the reaction mixture was concentrated under reduced pressure to afford the HCl salt of 4-(pyridazin-3-yl)cyclohexan-1-amine (600 mg, quantitative yield, 64 wt. %) as a brown oil, which was used without further purification. $^1$H NMR (300 MHz, DMSO-$d_6$) (mixture of stereoisomers) δ 9.31-9.54 (m, 1H), 8.18-8.35 (m, 2H), 3.39-3.46/3.18-3.32 (m, 1H) (stereoisomers), 2.98-3.14 (m, 1H), 2.08-2.34 (m, 2H), 1.86-2.08 (m, 2H), 1.64-1.86 (m, 3H), 1.45-1.64 (m, 1H). MS ESI, m/z=178 [M+H]$^+$.

5-Bromo-6-methoxy-2-(4-(pyridazin-3-yl)cyclohexyl)-2H-indazole

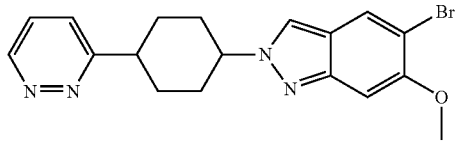 [SMILES: COc1cc2nn(C3CCC(c4cccnn4)CC3)cc2cc1Br]

To a solution of 5-bromo-4-methoxy-2-nitrobenzaldehyde (Int 1) (498 mg, 1.9 mmol) and TEA (1.2 mL, 8.7 mmol) in i-PrOH (20 mL) was added the HCl salt of 4-(pyridazin-3-yl)cyclohexan-1-amine (64 wt. %) (580 mg, 1.7 mmol) under N$_2$ atmosphere. The resulting mixture was stirred at 80° C. for 3 h, then cooled to rt and followed by the addition of tri-n-butylphosphine (1.7 mL, 7.0 mmol). The reaction mixture was stirred at 80° C. for 11 h and then concentrated under reduced pressure. The residue was purified by C18-flash chromatography (eluting with 0-100% MeCN in water (0.1% FA)) to afford 5-bromo-6-methoxy-2-(4-(pyridazin-3-yl)cyclohexyl)-2H-indazole (1.1 g, quantitative yield, 60 wt. %) as a brown oil, which was used without further purification. $^1$H NMR (400 MHz, DMSO-$d_6$) (mixture of stereoisomers) δ 9.10/9.08 (dd, 1H) (stereoisomers), 8.35/8.54 (s, 1H) (stereoisomers), 7.98/7.95 (s, 1H) (stereoisomers), 7.64-7.67/7.60-7.63 (m, 2H) (stereoisomers), 7.14/7.13 (s, 1H) (stereoisomers), 4.63-4.72/4.51-4.63 (m, 1H) (stereoisomers), 3.87/3.85 (s, 3H) (stereoisomers), 3.16-3.26/2.99-3.11 (m, 1H) (stereoisomers), 2.31-2.45 (m, 1H), 2.21-2.30 (m, 1H), 1.98-2.21 (m, 4H), 1.79-1.97 (m, 2H). MS ESI, m/z=387/389 (1:1) [M+H]$^+$.

Methyl 6-methoxy-2-(4-(pyridazin-3-yl)cyclohexyl)-2H-indazole-5-carboxylate

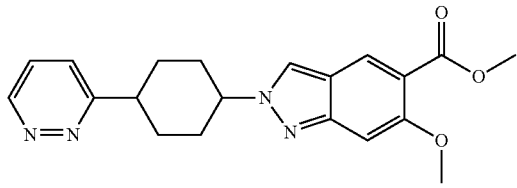 [SMILES: COC(=O)c1cc2cn(C3CCC(c4cccnn4)CC3)nc2cc1OC]

The mixture of 5-bromo-6-methoxy-2-(4-(pyridazin-3-yl)cyclohexyl)-2H-indazole (60 wt. %) (1.1 g, 1.7 mmol), TEA (2.7 g, 27.0 mmol) and Pd(dppf)Cl$_2$—CH$_2$Cl$_2$ (441 mg, 0.5 mmol) in MeOH (25 mL) was stirred in a sealed vessel under CO atmosphere at 15 atm, and then heated at 110° C. for 15 h. The reaction mixture was concentrated under reduced pressure and the residue was purified by C18-flash chromatography (eluting with 0-100% MeCN in water (0.05% FA)) to afford methyl 6-methoxy-2-(4-(pyridazin-3-yl)cyclohexyl)-2H-indazole-5-carboxylate (315 mg, 49%) as a brown solid. $^1$H NMR (300 MHz, DMSO-$d_6$) (mixture of stereoisomers) δ 9.06-9.13 (m, 1H), 8.5-8.55 (m, 1H), 8.09-8.16 (m, 1H), 7.61-7.68 (m, 2H), 7.08 (s, 1H), 4.66-4.75/4.52-4.66 (m, 1H) (stereoisomers), 3.76-3.85 (m, 6H), 3.28-3.13/2.97-3.13 (m, 1H) (stereoisomers), 1.81-2.33 (m, 8H). MS ESI, m/z=367 [M+H]$^+$. 6-Methoxy-2-(4-(pyridazin-3-yl)cyclohexyl)-2H-indazole-5-carboxylic acid

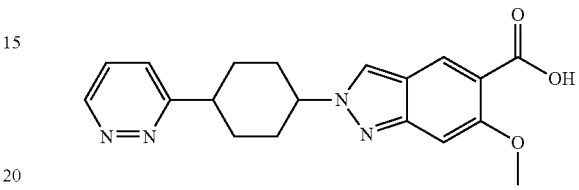

To a solution of methyl 6-methoxy-2-(4-(pyridazin-3-yl)cyclohexyl)-2H-indazole-5-carboxylate (295 mg, 0.8 mmol) in THF/water (1:1, 30 mL) was added LiOH (193 mg, 8.1 mmol). The resulting mixture was stirred at 25° C. for 3 h. Then, the reaction mixture was acidified to pH 6 with 2N HCl and extracted with EtOAc (50 mL×2). The organic layer was dried over Na$_2$SO$_4$, filtered and concentrated under reduced pressure. The residue was purified by C18-flash chromatography (eluting with 0-100% MeCN in water (0.1% FA)) to afford 6-methoxy-2-(4-(pyridazin-3-yl)cyclohexyl)-2H-indazole-5-carboxylic acid (150 mg, 53%) as a yellow solid. $^1$H NMR (400 MHz, DMSO-$d_6$) (1:1 mixture of stereoisomers) δ 9.11/9.08 (dd, 1H) (stereoisomers), 8.43/8.42 (s, 1H) (stereoisomers), 8.38 (br. s, 1H), 7.92/7.90 (s, 1H) (stereoisomers), 7.58-7.70 (m, 2H), 6.99 (s, 1H), 4.63-4.73/4.51-4.62 (m, 1H) (stereoisomers), 3.80/3.78 (s, 3H) (stereoisomers), 3.17-3.26/3.01-3.11 (m, 1H) (stereoisomers), 2.35-2.46 (m, 1H), 2.22-2.32 (m, 1H), 2.00-2.20 (m, 4H), 1.82-1.97 (m, 2H). MS ESI, m/z=353 [M+H]$^+$.

6-Methoxy-N-(1-methyl-2-oxo-1,2-dihydropyridin-3-yl)-2-(4-(pyridazin-3-yl)cyclohexyl)-2H-indazole-5-carboxamide—Isomer 1, Example 23 & Isomer 2, Example 24

ISOMER 1

ISOMER 2

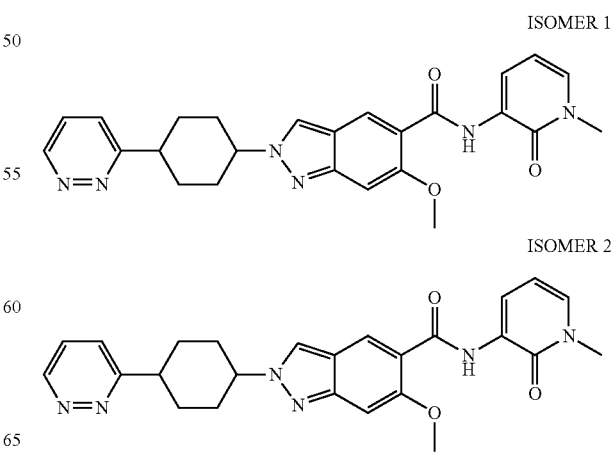

To a solution of 6-methoxy-2-(4-(pyridazin-3-yl)cyclohexyl)-2H-indazole-5-carboxylic acid (130 mg, 0.4 mmol), DIPEA (322 µL, 1.8 mmol) and 3-amino-1-methylpyridin-2(1H)-one hydrochloride (59 mg, 0.4 mmol) in DMF (10 mL) was added HATU (421 mg, 1.1 mmol) at 25° C. under $N_2$ atmosphere. The reaction mixture was stirred at 25° C. for 15 h. The mixture was purified directly by C18-flash chromatography (eluting with 0-100% MeCN in water (0.1% FA)) and further separated by chiral prep. HPLC (Chiralpak® IF, 5 µm 20 mm×250 mm; isocratic with 50% MTBE (0.5% 2M $NH_3$-MeOH solution) in MeOH for 26 min; 20.0 mL/min) to afford 6-methoxy-N-(1-methyl-2-oxo-1,2-dihydropyridin-3-yl)-2-(4-(pyridazin-3-yl)cyclohexyl)-2H-indazole-5-carboxamide—Isomer 1 (10.6 mg, 6%) and 6-methoxy-N-(1-methyl-2-oxo-1,2-dihydropyridin-3-yl)-2-(4-(pyridazin-3-yl)cyclohexyl)-2H-indazole-5-carboxamide—Isomer 2 (15.1 mg, 9%), both as colorless solids. Isomer 1, Example 23: 1H NMR (400 MHz, DMSO-$d_6$) δ 11.04 (s, 1H), 9.09 (dd, 1H), 8.65 (s, 1H), 8.58 (s, 1H), 8.45 (dd, 1H), 7.70-7.58 (m, 2H), 7.43 (dd, 1H), 7.25 (s, 1H), 6.31 (d, 1H), 4.70-4.80 (m, 1H), 4.06 (s, 3H), 3.56 (s, 3H), 3.18-3.28 (m, 1H), 2.35-2.47 (m, 2H), 2.23-2.03 (m, 4H), 1.88-2.00 (m, 2H). MS ESI, m/z=459 [M+H]$^+$. Isomer 2, Example 24: $^1$H NMR (400 MHz, DMSO-$d_6$) δ 11.05 (s, 1H), 9.11 (dd, 1H), 8.63 (s, 1H), 8.59 (s, 1H), 8.46 (dd, 1H), 7.63-7.73 (m, 2H), 7.44 (dd, 1H), 7.24 (s, 1H), 6.31 (t, 1H), 4.58-4.68 (m, 1H), 4.08 (s, 3H), 3.56 (s, 3H), 3.02-3.12 (m, 1H), 2.26-2.35 (m, 2H), 2.06-2.21 (m, 4H), 1.84-1.98 (m, 2H). MS ESI, m/z=459 [M+H]$^+$.

2-((1r,4r)-4-(1,3,4-Oxadiazol-2-yl)cyclohexyl)-6-methoxy-N-(1-methyl-2-oxo-1,2-dihydropyridin-3-yl)-2H-indazole-5-carboxamide (Example 25)

Benzyl ((1r,4r)-4-(hydrazinecarbonyl)cyclohexyl)carbamate

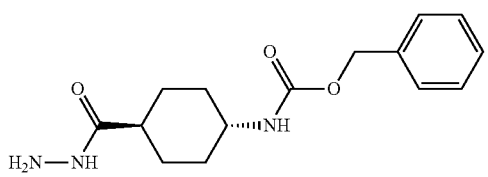

To a solution of (1r,4r)-4-(((benzyloxy)carbonyl)amino)cyclohexane-1-carboxylic acid (3.0 g, 10.8 mmol) in THF (100 mL) was added CDI (2.2 g, 13.5 mmol) in one portion. The resulting solution was stirred at 25° C. for 15 h. Subsequently, hydrazine monohydrate (2.2 g, 43.3 mmol) was added into the above solution. The resulting mixture was stirred at 25° C. for 1 h. The precipitate was collected by filtration, washed with EtOAc/PE (1:2, 150 mL) and then dried under reduced pressure to afford benzyl ((1r,4r)-4-(hydrazinecarbonyl)cyclohexyl)carbamate (2.3 g, 73%) as a colorless solid, which was used without further purification. $^1$H NMR (300 MHz, DMSO-$d_6$) δ 8.91 (s, 1H), 7.26-7.44 (m, 5H), 7.16-7.24 (m, 1H), 5.00 (s, 2H), 3.11-3.31 (m, 1H), 1.89-2.04 (m, 1H), 1.67-1.89 (m, 4H), 1.38-1.67 (m, 2H), 1.00-1.38 (m, 2H). MS ESI, m/z=292 [M+H]$^+$.

Benzyl ((1r,4r)-4-(1,3,4-oxadiazol-2-yl)cyclohexyl) carbamate

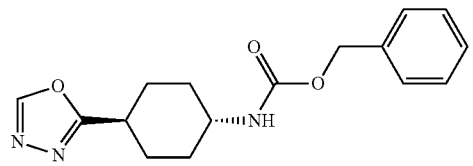 [SMILES: O=C(N[C@H]1CC[C@H](c2nnco2)CC1)OCc1ccccc1]

To a mixture of benzyl ((1r,4r)-4-(hydrazinecarbonyl)cyclohexyl)carbamate (2.1 g, 7.2 mmol) and trimethoxymethane (19.1 g, 180.2 mmol) was added 4-methylbenzenesulfonic acid (248 mg, 1.4 mmol). The resulting mixture was stirred at 90° C. for 2 h. The reaction mixture was purified directly by C18 flash chromatography (eluting with 5-80% MeCN in water (0.05% FA)) to afford benzyl ((1r,4r)-4-(1,3,4-oxadiazol-2-yl)cyclohexyl)carbamate (1.5 g, 70%) as a colorless solid. $^1$H NMR (400 MHz, DMSO-$d_6$) δ 9.13 (s, 1H), 7.26-7.43 (m, 6H), 5.02 (s, 2H), 3.25-3.80 (m, 1H), 2.90 (tt, 1H), 2.00-2.15 (m, 2H), 1.80-2.00 (m, 2H), 1.45-1.63 (m, 2H), 1.20-1.45 (m, 2H). MS ESI, m/z=302 [M+H]$^+$.

(1r,4r)-4-(1,3,4-Oxadiazol-2-yl)cyclohexan-1-amine

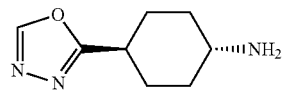 [SMILES: N[C@H]1CC[C@H](c2nnco2)CC1]

A suspension of 10 wt. % Palladium on carbon (470 mg, 0.4 mmol) and benzyl ((1r,4r)-4-(1,3,4-oxadiazol-2-yl)cyclohexyl)carbamate (1.3 g, 4.4 mmol) in MeOH (60 mL) was stirred at 50° C. under hydrogen at 1 atm for 2 h. The reaction mixture was then filtered through celite. The filtrate was concentrated under reduced pressure to afford (1r,4r)-4-(1,3,4-oxadiazol-2-yl)cyclohexan-1-amine (680 mg, 92%) as a colorless solid. $^1$H NMR (400 MHz, DMSO-$d_6$) δ 9.10 (s, 1H), 2.80-2.95 (m, 1H), 2.51-2.61 (m, 1H), 1.06-2.18 (m, 8H)). MS ESI, m/z=168 [M+H]$^+$.

2-((1r,4r)-4-(5-Bromo-6-methoxy-2H-indazol-2-yl)cyclohexyl)-1,3,4-oxadiazole

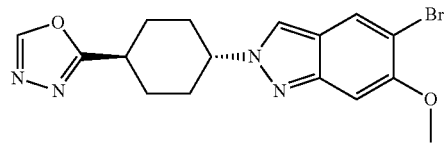 [SMILES: COc1cc2nn([C@H]3CC[C@H](c4nnco4)CC3)cc2cc1Br]

To a solution of (1r,4r)-4-(1,3,4-oxadiazol-2-yl)cyclohexan-1-amine (640 mg, 3.8 mmol) in i-PrOH (100 mL) was added 5-bromo-4-methoxy-2-nitrobenzaldehyde (Int 1) (1.1 g, 4.2 mmol) under $N_2$ atmosphere. The resulting mixture was stirred at 80° C. for 3 h, then cooled to rt, followed by the addition of tri-n-butylphosphine (3.8 mL, 15.3 mmol). The reaction mixture was stirred at 80° C. for 11 h and then concentrated under reduced pressure. The residue was purified by C18 flash chromatography (eluting with 0-100%

MeCN in water (0.1% NH₄OH)) and further by crystallization from PE (50 mL) to afford 2-((1r,4r)-4-(5-bromo-6-methoxy-2H-indazol-2-yl)cyclohexyl)-1,3,4-oxadiazole (640 mg, 44%) as a brown solid. ¹H NMR (400 MHz, DMSO-d₆) δ 9.18 (s, 1H), 8.30 (d, 1H), 7.98 (s, 1H), 7.11 (s, 1H), 4.55 (tt, 1H), 3.86 (s, 3H), 3.08-3.17 (m, 1H), 2.17-2.28 (m, 4H), 2.07 (qd, 2H), 1.77 (qd, 2H). MS ESI, m/z=377/379 (1:1) [M+H]⁺.

Methyl 2-((1r,4r)-4-(1,3,4-oxadiazol-2-yl)cyclohexyl)-6-methoxy-2H-indazole-5-carboxylate

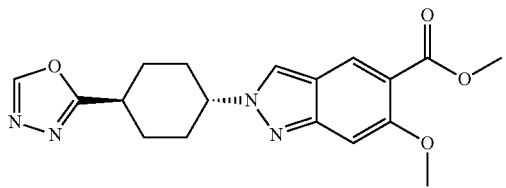 [SMILES: COC(=O)c1cc2cn([C@H]3CC[C@H](c4nnco4)CC3)nc2cc1OC]

A mixture of 2-((1r,4r)-4-(5-bromo-6-methoxy-2H-indazol-2-yl)cyclohexyl)-1,3,4-oxadiazole (300 mg, 0.8 mmol), Pd(dppf)Cl₂—CH₂CO₂ (130 mg, 0.2 mmol) and DIPEA (694 µL, 4.0 mmol) in MeOH (10 mL) was stirred in a sealed vessel under CO atmosphere at 15 atm, and then heated at 110° C. for 12 h. The reaction mixture was purified directly by C18 flash chromatography (eluting with 0-100% MeCN in water (0.1% NH₄OH)) to afford methyl 2-((1r,4r)-4-(1,3,4-oxadiazol-2-yl)cyclohexyl)-6-methoxy-2H-indazole-5-carboxylate (240 mg, 85%) as a light-yellow solid. ¹H NMR (300 MHz, DMSO-d₆) δ 9.18 (s, 1H), 8.47 (s, 1H), 8.11 (s, 1H), 7.07 (s, 1H), 4.50-4.64 (m, 1H), 3.83 (s, 3H), 3.79 (s, 3H), 3.07-3.21 (m, 1H), 2.18-2.35 (m, 4H), 1.99-2.18 (m, 2H), 1.70-1.88 (m, 2H). MS ESI, m/z=357 [M+H]⁺.

2-((1r,4r)-4-(1,3,4-Oxadiazol-2-yl)cyclohexyl)-6-methoxy-2H-indazole-5-carboxylic acid

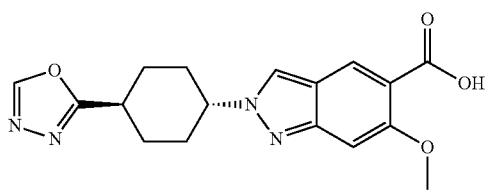 [SMILES: COc1cc2nn([C@H]3CC[C@H](c4nnco4)CC3)cc2cc1C(=O)O]

To a solution of methyl 2-((1r,4r)-4-(1,3,4-oxadiazol-2-yl)cyclohexyl)-6-methoxy-2H-indazole-5-carboxylate (235 mg, 0.7 mmol) in MeOH/water (2:1, 7.5 mL) was added LiOH (40 mg, 1.7 mmol). The resulting solution was stirred at 25° C. for 5 h. Then the pH of the reaction mixture was adjusted to pH 3-4 with 0.1N HCl. The resulting precipitate was collected by filtration and dried under reduced pressure to afford 2-((1r,4r)-4-(1,3,4-oxadiazol-2-yl)cyclohexyl)-6-methoxy-2H-indazole-5-carboxylic acid (155 mg, 69%) as a pale-yellow solid, which was used without further purification. ¹H NMR (400 MHz, DMSO-d₆) δ 12.24 (br. s, 1H), 9.17 (s, 1H), 8.44 (s, 1H), 8.08 (s, 1H), 7.03 (s, 1H), 4.56 (tt, 1H), 3.82 (s, 3H), 3.06-3.16 (m, 1H), 2.16-2.3 (m, 4H), 2.01-2.16 (m, 2H), 1.71-1.84 (m, 2H). MS ESI, m/z=343 [M+H]⁺.

2-((1r,4r)-4-(1,3,4-Oxadiazol-2-yl)cyclohexyl)-6-methoxy-N-(1-methyl-2-oxo-1,2-dihydropyridin-3-yl)-2H-indazole-5-carboxamide, Example 25

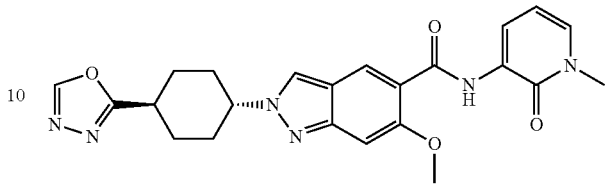

To a solution of 2-((1r,4r)-4-(1,3,4-oxadiazol-2-yl)cyclohexyl)-6-methoxy-2H-indazole-5-carboxylic acid (135 mg, 0.4 mmol), HATU (225 mg, 0.6 mmol) and DIPEA (207 µL, 1.2 mmol) in DMF (5 mL) was added 3-amino-1-methylpyridin-2(1H)-one hydrochloride (127 mg, 0.8 mmol). The reaction mixture was stirred at 25° C. under N₂ atmosphere for 10 h. The mixture was purified directly by prep. HPLC (Xbridge® BEH OBD C18 5 µm 30×150 mm; elution gradient 19-39% MeCN in water (10 mM NH₄HCO₃+0.1% NH₄OH) over 8 min; 60 mL/min) to afford 2-((1r,4r)-4-(1,3,4-oxadiazol-2-yl)cyclohexyl)-6-methoxy-N-(1-methyl-2-oxo-1,2-dihydropyridin-3-yl)-2H-indazole-5-carboxamide (105 mg, 59%), Example 25, as a colorless solid. ¹H NMR (400 MHz, DMSO-d₆) δ 11.05 (s, 1H), 9.18 (s, 1H), 8.59 (s, 2H), 8.45 (dd, 1H), 7.43 (dd, 1H), 7.23 (s, 1H), 6.31 (t, 1H), 4.55-4.66 (m, 1H), 4.07 (s, 3H), 3.56 (s, 3H), 3.09-3.20 (m, 1H), 2.20-2.31 (m, 4H), 2.03-2.18 (m, 2H), 1.73-1.87 (m, 2H). MS ESI, m/z=449 [M+H]⁺.

2-((1r,4r)-4-(1H-1,2,4-Triazol-1-yl)cyclohexyl)-6-methoxy-N-(1-methyl-2-oxo-1,2-dihydropyridin-3-yl)-2H-indazole-5-carboxamide (Example 26)

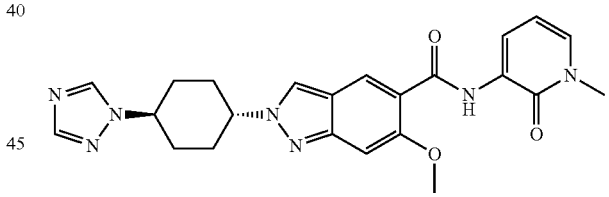

To a solution of (1s,4s)-4-(6-methoxy-5-((1-methyl-2-oxo-1,2-dihydropyridin-3-yl)carbamoyl)-2H-indazol-2-yl)cyclohexyl methanesulfonate (Int 8) (400 mg, 0.8 mmol) and 4H-1,2,4-triazole (1.2 g, 16.9 mmol) in toluene (5 mL) was added Cs₂CO₃ (824 mg, 2.5 mmol). The resulting mixture was stirred at 90° C. for 15 h and then concentrated under reduced pressure. The residue was purified by C18-flash chromatography (eluting with 0-100% MeCN in water (0.1% NH₄OH)) and further by prep. HPLC (Xbridge® BEH OBD C18 5 µm 30×150 mm; elution gradient 15-35% MeCN in water (10 mM NH₄HCO₃+0.1% NH₄OH) over 8 min, then isocratic elution at 35% MeCN in water (10 mM NH₄HCO₃+0.1% NH₄OH); 60 mL/min) to afford 2-((1r,4r)-4-(1H-1,2,4-triazol-1-yl)cyclohexyl)-6-methoxy-N-(1-methyl-2-oxo-1,2-dihydropyridin-3-yl)-2H-indazole-5-carboxamide (34 mg, 9%), Example 26, as a colorless solid. ¹H NMR (400 MHz, DMSO-d₆) δ 11.05 (s, 1H), 8.56-8.63 (m, 3H), 8.45 (dd, 1H), 8.00 (s, 1H), 7.43 (dd, 1H), 7.23 (s, 1H), 6.31 (t, 1H), 4.57-4.72 (m, 1H), 4.42-4.56 (m, 1H), 4.07 (s, 3H), 3.56 (s, 3H), 2.21-2.31 (m, 4H), 2.09-2.20 (m, 2H), 1.96-2.09 (m, 2H). MS ESI, m/z=448 [M+H]⁺.

2-((1r,4r)-4-(1H-1,2,3-Triazol-1-yl)cyclohexyl)-6-methoxy-N-(1-methyl-2-oxo-1,2-dihydropyridin-3-yl)-2H-indazole-5-carboxamide (Example 27)

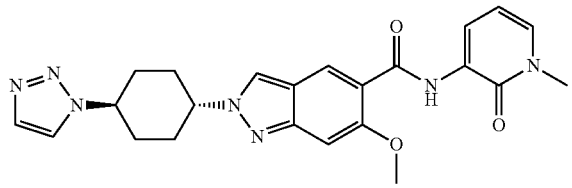 [SMILES: COc1cc2nn([C@H]3CC[C@H](n4ccnn4)CC3)cc2cc1C(=O)Nc1cccn(C)c1=O]

To a suspension of (1s,4s)-4-(6-methoxy-5-((1-methyl-2-oxo-1,2-dihydropyridin-3-yl)carbamoyl)-2H-indazol-2-yl)cyclohexyl methanesulfonate (Int 8) (74 wt. %) (500 mg, 0.8 mmol) and Cs₂CO₃ (914 mg, 2.8 mmol) in DMF (5 mL) was added 1H-1,2,3-triazole (1.0 g, 14.8 mmol). The resulting mixture was stirred at 90° C. for 2 h. The reaction mixture was purified directly by C18-flash chromatography (eluting with 0-100% MeCN in water (0.1% FA)) and further by prep. HPLC (Xbridge® BEH OBD C18 5 μm 30×150 mm; elution gradient 20-35% MeCN in water (10 mM NH₄HCO₃+0.1% NH₄OH) over 8 min; 60 mL/min) to afford 2-((1r,4r)-4-(1H-1,2,3-triazol-1-yl)cyclohexyl)-6-methoxy-N-(1-methyl-2-oxo-1,2-dihydropyridin-3-yl)-2H-indazole-5-carboxamide (20 mg, 44%), Example 27, as a colorless solid. ¹H NMR (400 MHz, DMSO-d₆) δ 11.05 (s, 1H), 8.62 (s, 1H), 8.59 (s, 1H), 8.45 (dd, 1H), 8.24 (d, 1H), 7.76 (d, 1H), 7.44 (dd, 1H), 7.24 (s, 1H), 6.31 (t, 1H), 4.60-4.77 (m, 2H), 4.07 (s, 3H), 3.56 (s, 3H), 2.04-2.34 (m, 8H). MS ESI, m/z=448 [M+H]⁺.

2-((1r,4r)-4-(2-(1-hydroxyethyl)-1H-imidazol-1-yl)cyclohexyl)-6-methoxy-N-(1-methyl-2-oxo-1,2-dihydropyridin-3-yl)-2H-indazole-5-carboxamide—Isomer 1 (Example 28) & Isomer 2 (Example 29)

2-((1r,4r)-4-(2-Acetyl-1H-imidazol-1-yl)cyclohexyl)-6-methoxy-N-(1-methyl-2-oxo-1,2-dihydropyridin-3-yl)-2H-indazole-5-carboxamide

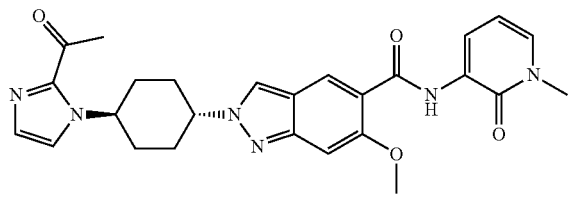 [SMILES: COc1cc2nn([C@H]3CC[C@H](n4ccnc4C(C)=O)CC3)cc2cc1C(=O)Nc1cccn(C)c1=O]

To a solution of (1s,4s)-4-(6-methoxy-5-((1-methyl-2-oxo-1,2-dihydropyridin-3-yl)carbamoyl)-2H-indazol-2-yl)cyclohexyl methanesulfonate (Int 8) (500 mg, 1.1 mmol) and 1-(1H-imidazol-2-yl)ethan-1-one (2.3 g, 21.1 mmol) in xylenes (10 mL) was added Cs₂CO₃ (1.0 g, 3.2 mmol) under N₂ atmosphere. The resulting mixture was stirred at 120° C. for 4 h. Then the reaction mixture was concentrated under reduced pressure. The residue was purified by C18-flash chromatography (eluting with 0-100% MeCN in water (0.1% NH₄OH)) to afford 2-((1r,4r)-4-(2-acetyl-1H-imidazol-1-yl)cyclohexyl)-6-methoxy-N-(1-methyl-2-oxo-1,2-dihydropyridin-3-yl)-2H-indazole-5-carboxamide (60 mg, 12%) as a brown solid. ¹H NMR (300 MHz, DMSO-d₆) δ 11.05 (s, 1H), 8.64 (d, 1H), 8.58 (s, 1H), 8.45 (dd, 1H), 7.78 (d, 1H), 7.43 (dd, 1H), 7.23 (s, 1H), 7.18 (d, 1H), 6.31 (t, 1H), 5.11-5.32 (m, 1H), 4.51-4.70 (m, 1H), 4.07 (s, 3H), 3.56 (s, 3H), 2.58 (s, 3H), 2.21-2.39 (m, 2H), 1.90-2.21 (m, 6H). MS ESI, m/z=489 [M+H]⁺.

2-((1r,4r)-4-(2-(1-hydroxyethyl)-1H-imidazol-1-yl)cyclohexyl)-6-methoxy-N-(1-methyl-2-oxo-1,2-dihydropyridin-3-yl)-2H-indazole-5-carboxamide—Isomer 1, Example 28 & Isomer 2, Example 29

ISOMER 1

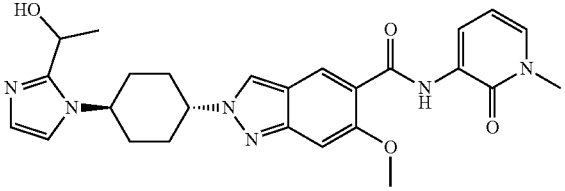

ISOMER 2

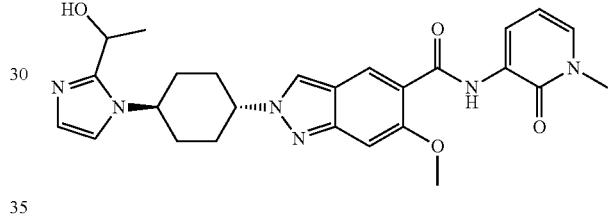

To a solution of 2-((1r,4r)-4-(2-acetyl-1H-imidazol-1-yl)cyclohexyl)-6-methoxy-N-(1-methyl-2-oxo-1,2-dihydropyridin-3-yl)-2H-indazole-5-carboxamide (55 mg, 0.1 mmol) in MeOH (5 mL) under N₂ atmosphere at rt was added NaBH₄ (9 mg, 0.2 mmol). The resulting mixture was stirred at rt for 1 h, and then concentrated under reduced pressure. The residue was purified by C18-flash chromatography (eluting with 0-100% MeCN in water (0.1% NH₄OH)) and then separated by prep. chiral-HPLC (YMC CHIRAL ART Cellulose-SC 5 μm 20 mm×250 mm; isocratic with 20% hexane/DCM (1/1) (0.5% 2M NH₃-MeOH) in IPA; 20 mL/min) to yield 2-((1r,4r)-4-(2-(1-hydroxyethyl)-1H-imidazol-1-yl)cyclohexyl)-6-methoxy-N-(1-methyl-2-oxo-1,2-dihydropyridin-3-yl)-2H-indazole-5-carboxamide-Isomer 1 (15 mg, 27%; 100% ee) and 2-((1r,4r)-4-(2-(1-hydroxyethyl)-1H-imidazol-1-yl)cyclohexyl)-6-methoxy-N-(1-methyl-2-oxo-1,2-dihydropyridin-3-yl)-2H-indazole-5-carboxamide—Isomer 2 (14 mg, 25%; 98.3% ee), both as colorless solids.

Isomer 1, Example 28: ¹H NMR (400 MHz, DMSO-d₆) δ 11.04 (s, 1H), 8.61 (s, 1H), 8.59 (s, 1H), 8.45 (dd, 1H), 7.43 (dd, 1H), 7.28 (d, 1H), 7.22 (s, 1H), 6.81 (d, 1H), 6.31 (t, 1H), 5.31 (d, 1H), 4.89 (p, 1H), 4.48-4.66 (m, 2H), 4.08 (s, 3H), 3.56 (s, 3H), 2.21-2.32 (m, 2H), 1.90-2.21 (m, 6H), 1.50 (d, 3H). MS ESI, m/z=491 [M+H]⁺.

Isomer 2, Example 29: ¹H NMR (400 MHz, DMSO-d₆) δ 11.04 (s, 1H), 8.62 (s, 1H), 8.59 (s, 1H), 8.45 (dd, 1H), 7.43 (dd, 1H), 7.28 (d, 1H), 7.22 (s, 1H), 6.81 (d, 1H), 6.31 (t, 1H), 5.31 (d, 1H), 4.89 (p, 1H), 4.47-4.67 (m, 2H), 4.08 (s, 3H), 3.56 (s, 3H), 2.20-2.32 (m, 2H), 1.92-2.20 (m, 6H), 1.50 (d, 3H). MS ESI, m/z=491 [M+H]⁺.

2-((1r,4r)-4-(4-(2-Hydroxypropan-2-yl)-1H-1,2,3-triazol-1-yl)cyclohexyl)-6-methoxy-N-(1-methyl-2-oxo-1,2-dihydropyridin-3-yl)-2H-indazole-5-carboxamide (Example 30)

2-((1r,4r)-4-Azidocyclohexyl)-6-methoxy-N-(1-methyl-2-oxo-1,2-dihydropyridin-3-yl)-2H-indazole-5-carboxamide

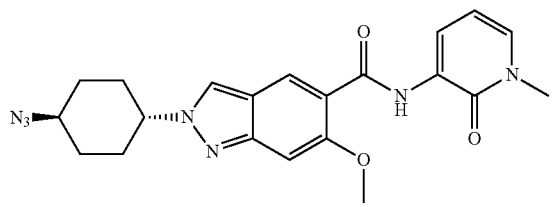 [SMILES: COc1cc2nn([C@H]3CC[C@H](N=[N+]=[N-])CC3)cc2cc1C(=O)Nc1cccn(C)c1=O]

To a solution of (1s,4s)-4-(6-methoxy-5-((1-methyl-2-oxo-1,2-dihydropyridin-3-yl)carbamoyl)-2H-indazol-2-yl)cyclohexyl methanesulfonate (Int 8) (70 wt. %) (500 mg, 0.7 mmol) in DMF (0.5 mL) under N$_2$ atmosphere was added sodium azide (121 mg, 1.9 mmol). The resulting mixture was stirred at 90° C. for 5 h, then diluted with water (150 mL) and extracted with DCM (250 mL). The organic layer was concentrated under reduced pressure. The residue was purified by C18-flash chromatography (eluting with 30-80% MeCN in water (0.1% NH$_4$OH)) to afford 2-((1r,4r)-4-azidocyclohexyl)-6-methoxy-N-(1-methyl-2-oxo-1,2-dihydropyridin-3-yl)-2H-indazole-5-carboxamide (250 mg, 80%) as a colorless solid. $^1$H NMR (300 MHz, DMSO-d$_6$) δ 11.04 (s, 1H), 8.57 (s, 1H), 8.55 (br. s, 1H), 8.44 (dd, 1H), 7.43 (dd, 1H), 7.21 (s, 1H), 6.31 (t, 1H), 4.45-4.61 (m, 1H), 4.06 (s, 3H), 3.52-3.68 (m, 1H), 3.56 (s, 3H), 1.93-2.25 (m, 6H), 1.47-1.67 (m, 2H). MS ESI, m/z=422 [M+H]$^+$.

2-((1r,4r)-4-(4-(2-Hydroxypropan-2-yl)-1H-1,2,3-triazol-1-yl)cyclohexyl)-6-methoxy-N-(1-methyl-2-oxo-1,2-dihydropyridin-3-yl)-2H-indazole-5-carboxamide, Example 30

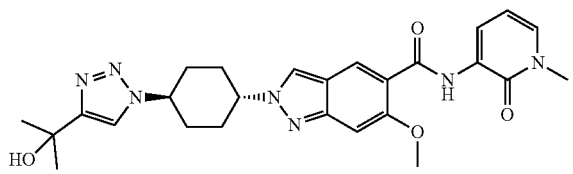 [SMILES: COc1cc2nn([C@H]3CC[C@H](n4cc(C(C)(C)O)nn4)CC3)cc2cc1C(=O)Nc1cccn(C)c1=O]

To a solution of 2-((1r,4r)-4-azidocyclohexyl)-6-methoxy-N-(1-methyl-2-oxo-1,2-dihydropyridin-3-yl)-2H-indazole-5-carboxamide (250 mg, 0.6 mmol) in DMF (5 mL) under N$_2$ atmosphere was added 2-methylbut-3-yn-2-ol (1.5 g, 17.8 mmol). The resulting mixture was stirred at 100° C. for 15 h. The reaction mixture was purified directly by C18-flash chromatography (eluting with 0-100% MeCN in water (0.1% NH$_4$OH)) and further by prep. HPLC (Waters XSelect CSH Fluoro-Phenyl OBD, 5 μm 30×150 mm; elution gradient 30-40% MeCN in water (0.1% FA) over 8 min; 60 mL/min; to afford 2-((1r,4r)-4-(4-(2-hydroxypropan-2-yl)-1H-1,2,3-triazol-1-yl)cyclohexyl)-6-methoxy-N-(1-methyl-2-oxo-1,2-dihydropyridin-3-yl)-2H-indazole-5-carboxamide (145 mg, 48%), Example 30, as a colorless solid. $^1$H NMR (400 MHz, DMSO-d$_6$) δ 11.05 (s, 1H), 8.61 (s, 1H), 8.59 (s, 1H), 8.45 (dd, 1H), 7.98 (s, 1H), 7.44 (dd, 1H), 7.23 (s, 1H), 6.31 (t, 1H), 5.11 (s, 1H), 4.58-4.70 (m, 2H), 4.07 (s, 3H), 3.56 (s, 3H), 2.01-2.35 (m, 8H), 1.47 (s, 6H). MS ESI, m/z=506 [M+H]$^+$.

Potency of IRAK4 Inhibitor Compounds in IRAK4 Enzyme Assay

The inhibitory activity of compounds against IRAK4 were determined in an enzymatic assay using mass spectrometry readout. Ten point half-log compound concentration response curves, with a top concentration of 1 μM or 10 μM, were generated from 10 mM stocks of compound solubilized in DMSO using an Echo 655 (Labcyte Inc) and added to 384 well assay plates (Greiner #781280). To the assay plates, 10 μL of human recombinant IRAK4 protein (Life Technologies #PV4002) diluted to a final concentration of 0.2 nM in assay buffer (50 mM Tris-HCl pH 7.4, 10 mM MgCl, 5 mM glutathione, 0.01% BSA, 3 mM ATP) was added. The enzyme was incubated with the compounds at room temperature for 15 minutes before a peptide substrate (KKARFSRFAGSSPSQSSMVAR, Innovagen custom synthesis, 10 mM in DMSO) was added to each well to a final concentration of 10 μM using an Echo 655 (Labcyte Inc). After two hours at room temperature, the reaction was stopped with 65 μL of 0.4% formic acid (Merck #33015). The unphosphorylated and phosphorylated peptide were measured by LC-MS/MS on a Waters TQ-S mass spectrometer. Peaks were integrated using the TargetLynx software and the ratios between phosphorylated and unphosphorylated peptides were calculated. Curves were fitted and compound potencies determined in Genedata Screener 19 (Genedata AG). IC$_{50}$ values are the geometric mean of at least 2 experiments.

IRAK4 Phosphorylation Cell Assay

The activation of IRAK4 by TLR or IL-1R ligands leads to IRAK4 auto-phosphorylation, which can be prevented by IRAK4 kinase inhibitors. The effect of IRAK4 inhibitor compounds on IRAK4 auto-phosphorylation was assessed in IL-1β-stimulated Karpas-299 cells as a measurement of cellular potency. Karpas-299 cells were cultured in RPMI 1640 (Gibco 61870-010) containing 10% FBS (Gibco #10270). Cells were plated at 2×10$^4$ cells per well in poly-D-lysine coated 384 well plates (Corning #356663) to which compounds had been added at various concentrations (10 point half log dose response with a final top concentration of 30 μM) using an Echo 655 (Labcyte Inc). Cells were centrifuged (250 g, 4 mins), incubated at 37° C. for 1 h, then stimulated with 22.7 ng/mL recombinant IL-1β (R&D Systems, #201-LB-025) at 37° C. for 10 mins, followed by fixation in 4% paraformaldehyde for 20 mins and permeabilization in ice-cold 70% MeOH in PBS for 30 mins. Cells were washed twice with phosphate-buffered saline (PBS) on a BlueWasher (BlueCatBio) then blocked with PBS containing 10% FBS for 20 mins. Blocking solution was removed with a BlueWasher and cells were stained with anti-pIRAK4 (Thr345/Ser346) (CST, #11927, 1:400) in blocking buffer with 0.05% Tween-20 for 1 h, then washed twice with PBS containing 0.05% Tween-20 on a BlueWasher, followed by staining with a Alexa 647-conjugated secondary anti-rabbit IgG antibody (CST, #4414, 1:2,000) and Hoechst 33342 (Sigma, 1:2,000) in blocking buffer with 0.05% Tween-20 for 30 mins. Finally, the cells were washed twice with PBS containing 0.05% Tween-20 and imaged on an ImageXpress Micro (Molecular Devices) with a 10× air objective using the appropriate filters. Images were analysed in Columbus (PerkinElmer) and the fluorescence intensity per cell from the secondary antibody was quantified. The quantified data were analysed in Genedata Screener 19 (Genedata AG). Results obtained in this assay are presented in Table 1 and demonstrate the ability of the compounds of the present specification to inhibit IRAK4 in cells. $IC_{50}$ values are the geometric mean of at least 2 experiments.

TABLE 1

Activity of Compounds in IRAK4 enzyme inhibition assay and IRAK4 phosphorylation cell assay

| Example | IRAK4 Enzyme $IC_{50}$ (nM) | IRAK4 Cell $IC_{50}$ (nM) |
|---|---|---|
| 1 | 1.1 | 30 |
| 2 | 10.7 | 238 |
| 3 | 0.7 | 21 |
| 4 | 3.9 | 67 |
| 5 | 0.8 | 24 |
| 6 | 199.3 | 2876 |
| 7 | 458.7 | 4502 |
| 8 | 0.8 | 29 |
| 9 | 0.4 | 15 |
| 10 | 1.4 | 37 |
| 11 | 0.9 | 23 |
| 12 | 0.6 | 24 |
| 13 | 0.7 | 30 |
| 14 | 0.3 | 15 |
| 15 | 0.9 | 35 |
| 16 | 1.0 | 33 |
| 17 | 1.1 | 34 |
| 18 | 1.0 | 32 |
| 19 | 0.9 | 34 |
| 20 | 5.6 | 128 |
| 21 | 0.4 | 20 |
| 22 | 0.5 | 26 |
| 23 | 5.0 | 185 |
| 24 | 1.2 | 17 |
| 25 | 1.7 | 45 |
| 26 | 2.2 | 38 |
| 27 | 1.5 | 39 |
| 28 | 0.5 | 31 |
| 29 | 0.6 | 19 |
| 30 | 1.0 | 22 |

Potency of IRAK4 Inhibitor Compounds in cKit Enzyme Assay

Evaluation of the effects of the IRAK4 inhibitor compounds on the activity of the human cKit kinase quantified by measuring the phosphorylation of the substrate Ulight-TK peptide using a human recombinant enzyme and the LANCE® detection method at Eurofins CEREP, catalog item 3070, SOP no 1C768: The test compound, reference compound or water (control) are mixed with the enzyme (0.38 ng) in a buffer containing 40 mM Hepes/Tris (pH 7.4), 0.8 mM EGTA/Tris, 8 mM $MgCl_2$, 1.6 mM DTT and 0.008% Tween 20. Thereafter, the reaction is initiated by adding 100 nM of the substrate Ulight-TK peptide and 50 µM ATP, and the mixture is incubated for 30 min at room temperature. For control basal measurements, the enzyme is omitted from the reaction mixture. Following incubation, the reaction is stopped by adding 13 mM EDTA. After 5 min, the anti-phopho-PT66 antibody labeled with europium chelate is added. After 60 more min, the fluorescence transfer is measured at lex=337 nm, lem=620 nm and lem=665 nm using a microplate reader (Envision, Perkin Elmer). The enzyme activity is determined by dividing the signal measured at 665 nm by that measured at 620 nm (ratio). The results are expressed as a percent inhibition of the control enzyme activity. The standard inhibitory reference compound is staurosporine, which is tested in each experiment at several concentrations to obtain an inhibition curve from which its $IC_{50}$ value is calculated.

Data presented are the geometric mean of at least n=2, or as denoted by an * are obtained from a single experiment. As can be appreciated from comparison of the data in Tables 1 and 2 the compounds of the present specification selectively inhibit IRAK4 versus cKit. Further screening not shown here revealed that the compounds of the present specification are selective for IRAK4 relative to a broad panel of kinases. Kinase selectivity can be a key determinant of clinical utility as off target toxicity can be reduced or eliminated.

TABLE 2

Activity of Compounds in cKit enzyme assay

| Example | cKit Enzyme $IC_{50}$ (µM) |
|---|---|
| 1 | 13.0 |
| 2 | — |
| 3 | 13.7 |
| 4 | 18.3* |
| 5 | >40 |
| 6 | — |
| 7 | — |
| 8 | 7.0 |
| 9 | 3.3* |
| 10 | 2.5* |
| 11 | 36.3 |
| 12 | 58.2 |
| 13 | >50 |
| 14 | — |
| 15 | 2.7 |
| 16 | 1.4 |
| 17 | >100 |
| 18 | 2.4* |
| 19 | 10.6* |
| 20 | — |
| 21 | — |
| 22 | 26.2 |
| 23 | — |
| 24 | 88.1 |
| 25 | >100* |
| 26 | >100 |
| 27 | >100 |
| 28 | 10.6* |
| 29 | 8.4* |
| 30 | 6.9* |

Plasma protein binding may have important implications on the pharmacokinetic behaviour of drugs. This is especially true for highly bound drugs, where the fraction unbound (fu) drug in plasma is an important parameter in the interpretation of in-vivo experiments. Traditionally, there are several different techniques used to determine the extent of drug binding to plasma proteins and equilibrium dialysis is probably the most common.

This method describes our current automated equilibrium dialysis assay in human plasma using the RED (Rapid Equilibrium Dialysis) Device and Hamilton sample handling system, described in WernevikJ et al. (2020) "A Fully Integrated Assay Panel for Early Drug Metabolism and Pharmacokinetics Profiling" Assay. Drug. Dev. Technol 18:157-179; DOI 10.1089/adt.2020.970.

The assay generally runs over three days including delivery of results. The pooled compounds are diluted in plasma to 5 µM and added to the inner chamber of the RED device and a phosphate buffer (pH 7.4) to the surrounding chamber to allow equilibrium dialysis over a semipermeable membrane with a molecular weight cut off at 8 kDa. The 5 µM solutions are also used to establish compound stability in plasma and recovery (mass balance) in the RED devices, with sampling performed at both the 0 and 18 h timepoints. Low recovery indicates binding to the dialysis equipment or solubility issues.

After dialysis for 18 hours, plasma and buffer samples are prepared for analysis by liquid chromatography and mass spectrometry (LC/MSMS). A seven-point calibration curve in plasma, ranging from 1.4 nM to 7 μM, is used to quantify the samples. All samples including the calibration curve, also contain an internal standard (IS) to allow for normalization between variations in injection volume in the UPLC-MS/MS instrumentation.

Three quality controls (QCs) are used in each run. Warfarin with low fu (fu mean ~1%) is used as a control in each pool. Propranolol (~30%) and Metoprolol (~90%) are placed randomly in each run. The controls are monitored in the "Manhattan tool" (Winiwarter et al. (2015) *"Time dependent analysis of assay comparability: a novel approach to understand intra-and inter-site variability over time"* J. Comput. Aided Mol. Des. 29:795-807; DOI10.1007/s10822-015-9836-5), that defines the acceptance criteria for the QCs as 2.58×standard deviation.

As can be seen from the data in Table 3 concentrations of the compounds according to the specification are unbound in plasma indicating that free compound will be available to bind to, and inhibit, IRAK4 in vivo.

TABLE 3

Data for human plasma protein binding generated for selected examples (the data may be a result from a single experiment or an average of two or more experiments)

| Example | Hu PPB (% free) |
|---|---|
| 1 | 16 |
| 3 | 16 |
| 5 | 18 |
| 8 | 23 |
| 10 | 40 |
| 11 | 17 |
| 12 | 17 |
| 14 | 22 |
| 15 | 13 |
| 16 | 5 |
| 17 | 11 |
| 18 | 17 |
| 20 | 14 |
| 22 | 13 |
| 24 | 8 |
| 27 | 14 |
| 28 | 26 |
| 29 | 15 |
| 30 | 10 |

The invention claimed is:

1. A compound which is N-(1-Cyclopropyl-2-oxo-1,2-dihydropyridin-3-yl)-2-((1 S,4r)-4-((S)-2-hydroxy-N-methylpropanamido)cyclohexyl)-6-methoxy-2H-indazole-5-carboxamide:

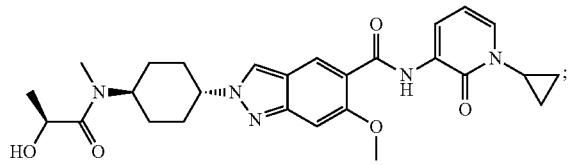 [SMILES: COc1cc2nn([C@H]3CC[C@H](N(C)C(=O)[C@H](C)O)CC3)cc2cc1C(=O)Nc1cccn(C2CC2)c1=O]

or a pharmaceutically acceptable salt thereof.

2. The compound according to claim 1, which is N-(1-Cyclopropyl-2-oxo-1,2-dihydropyridin-3-yl)-2-((1S,4r)-4-((S)-2-hydroxy-N-methylpropanamido)cyclohexyl)-6-methoxy-2H-indazole-5-carboxamide:

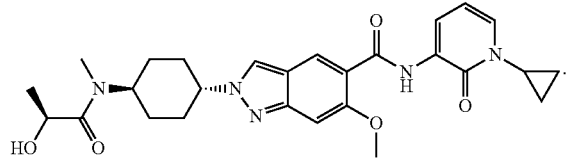 [SMILES: COc1cc2nn([C@H]3CC[C@H](N(C)C(=O)[C@H](C)O)CC3)cc2cc1C(=O)Nc1cccn(C2CC2)c1=O]

3. The pharmaceutically acceptable salt according to claim 1, which is a pharmaceutically acceptable salt of the compound N-(1-Cyclopropyl-2-oxo-1,2-dihydropyridin-3-yl)-2-((1S,4r)-4-((S)-2-hydroxy-N-methylpropanamido)cyclohexyl)-6-methoxy-2H-indazole-5-carboxamide:

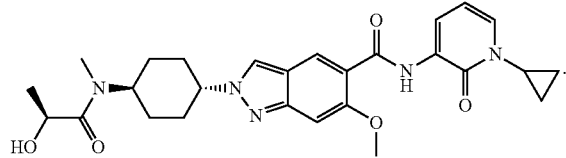 [SMILES: COc1cc2nn([C@H]3CC[C@H](N(C)C(=O)[C@H](C)O)CC3)cc2cc1C(=O)Nc1cccn(C2CC2)c1=O]

4. A pharmaceutical composition comprising the compound or pharmaceutically acceptable salt thereof according to claim 1.

* * * * *